US011813264B2

(12) United States Patent
Scarisbrick et al.

(10) Patent No.: US 11,813,264 B2
(45) Date of Patent: Nov. 14, 2023

(54) PAR1 MODULATION TO ALTER MYELINATION

(71) Applicant: Mayo Foundation for Medical Education and Research, Rochester, MN (US)

(72) Inventors: Isobel A Scarisbrick, Rochester, MN (US); Hye-Sook Yoon, Rochester, MN (US); Kristen L. Drucker, Oronoco, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 17/528,103

(22) Filed: Nov. 16, 2021

(65) Prior Publication Data

US 2022/0241282 A1 Aug. 4, 2022

Related U.S. Application Data

(63) Continuation of application No. 16/776,215, filed on Jan. 29, 2020, now abandoned, which is a continuation of application No. 15/815,274, filed on Nov. 16, 2017, now abandoned, which is a continuation of application No. 14/793,244, filed on Jul. 7, 2015, now abandoned.

(60) Provisional application No. 62/021,566, filed on Jul. 7, 2014.

(51) Int. Cl.
*A61K 31/519* (2006.01)
*A61K 35/30* (2015.01)
*A61K 31/7105* (2006.01)
*A61K 48/00* (2006.01)
*C12N 15/00* (2006.01)
*C12N 15/63* (2006.01)
*C12N 15/85* (2006.01)
*A61K 35/12* (2015.01)

(52) U.S. Cl.
CPC ........ *A61K 31/519* (2013.01); *A61K 31/7105* (2013.01); *A61K 35/30* (2013.01); *A61K 48/00* (2013.01); *A61K 48/0058* (2013.01); *A61K 48/0066* (2013.01); *C12N 15/00* (2013.01); *C12N 15/63* (2013.01); *C12N 15/85* (2013.01); *A61K 35/12* (2013.01); *C12N 2506/03* (2013.01); *C12N 2506/08* (2013.01)

(58) Field of Classification Search
CPC .. A61K 31/519; A61K 31/7105; A61K 35/30; A61K 48/00; A61K 48/0058; A61K 48/0066; C12N 15/00; C12N 15/63; C12N 15/85

See application file for complete search history.

(56) References Cited

U.S. PATENT DOCUMENTS

| | | | |
|---|---|---|---|
| 3,687,808 A | 8/1972 | Merigan, Jr. et al. | |
| 4,469,863 A | 9/1984 | Ts'o et al. | |
| 4,816,567 A | 3/1989 | Cabilly et al. | |
| 5,214,136 A | 5/1993 | Lin et al. | |
| 5,218,105 A | 6/1993 | Cook et al. | |
| 5,235,033 A | 8/1993 | Summerton et al. | |
| 5,482,856 A | 1/1996 | Fell, Jr. et al. | |
| 5,565,332 A | 10/1996 | Hoogenboom et al. | |
| 5,596,086 A | 1/1997 | Matteucci et al. | |
| 5,750,666 A | 5/1998 | Caruthers et al. | |
| 6,054,297 A | 4/2000 | Carter et al. | |
| 6,077,990 A | 6/2000 | Leung et al. | |
| 6,808,901 B1 | 10/2004 | Neuberger et al. | |
| 6,933,146 B2 | 8/2005 | Helliwell et al. | |
| 8,530,427 B2 | 9/2013 | Scarisbrick | |
| 9,376,499 B2 | 6/2016 | Kuliopulos et al. | |
| 9,732,128 B2 | 8/2017 | West et al. | |
| 2004/0096443 A1* | 5/2004 | Traynelis ................ A61P 31/00 424/143.1 |
| 2006/0216290 A1 | 9/2006 | Golz et al. | |
| 2007/0053911 A1 | 3/2007 | Golz et al. | |
| 2011/0065676 A1 | 3/2011 | Perelman et al. | |
| 2012/0129262 A1 | 5/2012 | West et al. | |
| 2013/0315926 A1 | 11/2013 | Scarisbrick | |
| 2016/0000791 A1 | 1/2016 | Scarisbrick | |
| 2017/0137492 A1 | 5/2017 | Looby | |
| 2018/0147209 A1 | 5/2018 | Scarisbrick | |
| 2018/0170982 A1 | 6/2018 | West et al. | |
| 2019/0201454 A1 | 7/2019 | Yoon et al. | |
| 2020/0397788 A1 | 12/2020 | Scarisbrick et al. | |
| 2023/0000928 A1 | 1/2023 | Yoon et al. | |
| 2023/0061116 A1 | 3/2023 | Scarisbrick et al. | |

FOREIGN PATENT DOCUMENTS

| | | |
|---|---|---|
| WO | WO 2005/078117 | 8/2005 |
| WO | WO 2009/117481 | 9/2009 |
| WO | WO 2012/033518 | 3/2012 |

(Continued)

OTHER PUBLICATIONS

Baumer et al. "Proteinase-Activated Receptor 1 (PAR1) Regulates Leukemic Stem Cell Functions", PLoS One. Apr. 16, 2014;9(4):e94993 (Year: 2014).*

Ben-Hur et al. "Cell-Based Reparative Therapies for Multiple Sclerosis", Curr Neurol Neurosci Rep. Nov. 2013;13(11):397. (Year: 2013).*

Kassel et al., "Protease-Activated Receptor 1 and Hematopoietic Cell Tissue Factor are Required for Hepatic Steatosis in Mice Fed a Western Diet," Am. J. Pathol., 179(5):2278-2289, Nov. 2011.

Lee et al., "Expression of Protease-Activated Receptor-2 in SZ95 Sebocytes and its Role in Sebaceous Lipogenesis, Inflammation, and Innate Immunity," J. Invest. Dermatol., 135(9):2219-2227, Sep. 2015.

(Continued)

*Primary Examiner* — Amy E Juedes
*Assistant Examiner* — Peter Johansen
(74) *Attorney, Agent, or Firm* — Fish & Richardson P.C.

(57) ABSTRACT

Materials and methods for modulating protease activated receptor 1 (PAR1) activity to alter myelination are provided.

13 Claims, 29 Drawing Sheets

Specification includes a Sequence Listing.

(56) References Cited

FOREIGN PATENT DOCUMENTS

WO    WO 2019/172969    9/2019

OTHER PUBLICATIONS

Ramachandran et al., "Targeting proteinase-activated receptors: therapeutic potential and challenges," Nat. Rev. Drug Discov., 11(1):69-86, Jan. 2012.
Saher et al., "Cholesterol in myelin biogenesis and hypomyelinating disorders," Biochim. Biophys. Acta., 1851(8):1083-1094, Aug. 2015.
Yao et al., "Activation of sterol regulatory element-binding proteins (SREBPs) is critical in IL-8-induced angiogenesis," J. Leukocyte Biol., 80(3):608-620, Sep. 2006.
U.S. Appl. No. 17/792,591, filed Jul. 13, 2022, Isobel A. Scarisbrick, Pending.
U.S. Appl. No. 17/944,699, filed Sep. 14, 2022, Hye-Sook Yoon, Pending.
Hamilton et al., "Challenges and Opportunities in Protease-Activated Receptor Drug Development," Annu. Rev. Pharmacol. Toxicol., Jan. 2017, 57:349-373, 28 pages.
Lim et al., "Diet-induced obesity, adipose inflammation, and metabolic dysfunction correlating with PAR2 expression are attenuated by PAR2 antagonism," The FASEB Journal, Aug. 2013, 27(12):4757-4767.
Rana et al., "PAR2 controls cholesterol homeostasis and lipid metabolism in nonalcoholic fatty liver disease," Molecular Metabolism, Nov. 2019, 29:99-113.
Achilleos et al. Cell Res., 22:288-304, 2012.
Adams et al., "Structure, function and pathophysiology of protease activated receptors," Pharmacol Ther., 130(3):248-282, Epub Jan. 26, 2011.
Aguirre et al., "Reduced EGFR signaling in progenitor cells of the adult subventricular zone attenuates oligodendrogenesis after demyelination," Neuron Glia Biology, 3(3):209-220, Aug. 2007.
Angelo et al., "Substrate specificity of human kallikrein 6: salt and glycosaminoglycan activation effects," J Biol Chem., 281(6):3116-3126, Epub Dec. 1, 2005.
Arai et al., "Thrombin and prothrombin are expressed by neurons and glial cells and accumulate in neurofibrillary tangles in Alzheimer disease brain," J Neuropathol Exp Neurol., 65(1):19-25, Jan. 2006.
Arif et al., "Vorapaxar for reduction of thrombotic cardiovascular events in myocardial infarction and peripheral artery disease," Am. J. Health Syst. Pharmacy, 72(19):1615-1622, Oct. 2015.
Azim et al., "Intraventricular injection of FGF-2 promotes generation of oligodendrocyte-lineage cells in the postnatal and adult forebrain," Glia, 60(12):1977-1990, Dec. 2012.
Back et al., "Maturation-dependent vulnerability of oligodendrocytes to oxidative stress-induced death caused by glutathione depletion," J Neurosci., 18(16):6241-6253, Aug. 15, 1998.
Bernett et al., "Crystal structure and biochemical characterization of human kallikrein 6 reveals that a trypsin-like kallikrein is expressed in the central nervous system," J Biol Chem., 277(27):24562-24570, Epub Apr. 30, 2002.
Bjartmar et al., "Axonal loss in the pathology of MS: consequences for understanding the progressive phase of the disease," J. Neurol. Science, 206(2):165-171, Feb. 15, 2003.
Blaber et al., "Enzymatic properties of rat myelencephalon-specific protease," Biochemistry., 41(4):1165-1173, Jan. 29, 2002.
Blaber et al., "Targeting kallikrein 6 proteolysis attenuates CNS inflammatory disease," FASEB J., 18(7):920-922, Epub Mar. 19, 2004.
Blakemore et al., "Remyelinating the demyelinated CNS," Novartis Found. Symposium, 231:289-301, 2000.
Borgono et al., "Human tissue kallikreins: physiologic roles and applications in cancer," Mol Cancer Res., 2(5):257-280, May 2004.
Boven et al., "Up-regulation of proteinase-activated receptor 1 expression in astrocytes during HIV encephalitis," J Immunol., 170(5):2638-2646, Mar. 1, 2003.
Brousse et al., "Region and dynamic specificities of adult neural stem cells and oligodendrocyte precursors in myelin regeneration in the mouse brain," Biol. Open, 4(8):980-992, Jul. 3, 2015.
Burda et al., "Critical role for PAR1 in kallikrein 6-mediated oligodendrogliopathy," Glia., 61(9):1456-1470, Epub Jul. 8, 2013.
Burda et al., "Hormone-like activity of kallikrein 6 regulates oligodendrocyte differentiation and white matter degeneration," [presentation abstract] 42nd Annual Society for Neuroscience meeting, New Orleans, LA, 2 pages, 2012.
Bushell, J. Physiol. 2007; 581.1:7-16. D01:10.1113/physiol.2007.129577.
Cahoy et al., "A transcriptome database for astrocytes, neurons, and oligodendrocytes: a new resource for understanding brain development and function," J Neurosci., 28(1):264-278, Jan. 2, 2008.
Cai et al., "Intranasal administration of insulin-like growth factor-1 protects against lipopolysaccharide-induced injury in the developing rat brain," Neuroscience, 194:195-207, Oct. 27, 2011.
Camerer et al. Dev. Cell, 2010; 18:25-38.
Chang et al., "Premyelinating oligodendrocytes in chronic lesions of multiple sclerosis," N Engl J Med., 346(3):165-173, Jan. 17, 2002.
Chen et al., "Thrombin activity associated with neuronal damage during acute focal ischemia," J Neurosci., 32(22):7622-7631, May 30, 2012.
Choi et al., "The Thrombin Receptor Restricts Subventricular Zone Neural Stem Cell Expansion and Differentiation" Scientific Reports, 8(1):9360, Jun. 2018.
Chow et al., "Kallikreins is microRNA targets: an in silico and experimental-based analysis," Biological Chem., 389:731-738, Jun. 2008.
Chrast et al., "Lipid metabolism in myelinating glial cells: lessons from human inherited disorders and mouse models," J. Lipid Research, 52(3):419-434, Mar. 2011.
Christophi et al., "Distinct promoters regulate tissue-specific and differential expression of kallikrein 6 in CNS demyelinating disease," J Neurochem., 91(6):1439-1449, Dec. 2004.
Citron et al., "Upregulation of neurotoxic serine proteases, prothrombin, and protease-activated receptor 1 early after spinal cord injury," J Neurotrauma., 17(12):1191-1203, Dec. 2000.
Cogoni and Masino, "Gene silencing in Neurospora crassa requires a protein homologous to RNA-dependent RNA polymerase," Nature., 399(6732):166-169, May 13, 1999.
Cogoni et al., "Transgene silencing of the al-1 gene in vegetative cells of Neurospora is mediated by a cytoplasmic effector and does not depend on DNA-DNA interactions or DNA methylation," EMBO J., 15(12):3153-3163, Jun. 17, 1996.
Cole et al., "Monoclonal Antibodies and Cancer Therapy," Alan R. Liss Inc., 1983, pp. 77-96.
Copp et al. Dev. Cell, 2010; 18:1-2.
Crawford et al., "Remyelination: the true regeneration of the central nervous system," J Comp Pathol., 149(2-3):242-254, Epub Jul. 5, 2013.
Cristiano et al., "Molecular conjugates: a targeted gene delivery vector for molecular medicine," J Mol Med (Berl)., 73(10):479-486, Oct. 1995.
Czopka et al., "Regulatory mechanisms that mediate tenascin C-dependent inhibition of oligodendrocyte precursor differentiation," J Neurosci., 30(37):12310-12322, Sep. 15, 2010.
Das et al. J. Stem Cells, 2013; 8: 1-16.
Debela et al., "Structures and specificity of the human kallikrein-related peptidases KLK 4, 5, 6, and 7," Biol. Chem. 389:623-632, Jun 2008.
Dell'Albani et al., "Oligodendroglial survival factors, PDGF-AA and CNTF, activate similar JAK/STAT signaling pathways," J Neurosci Res., 54(2):191-205, Oct. 15, 1998.
Denic et al., "Brainstem 1H nuclear magnetic resonance (NMR) spectroscopy: marker of demyelination and repair in spinal cord," Ann Neurol., 66(4):559-564, Oct. 2009.
Deshmukh et al., "A regenerative approach to the treatment of multiple sclerosis," Nature, 502(7471):327-332, Oct. 9, 2013.
Di Serio et al., "Protease-activated receptor 1-selective antagonist SCH79797 inhibits cell proliferation and induces apoptosis by a protease-activated receptor 1—independent mechanism," Basic Clin Pharmacol Toxicol., 101(1):63-69, Jul. 2007.

(56) References Cited

OTHER PUBLICATIONS

Diamandis et al., "Human kallikrein 6 (zyme/protease M/neurosin): a new serum biomarker of ovarian carcinoma," Clin. Biochem., 2000, 33:579-583.
Doetsch et al., "Subventricular zone astrocytes are neural stem cells in the adult mammalian brain," Cell, 97(6):703-716, Jun. 11, 1999.
Drucker et al., "Clinical significance and novel mechanism of action of kallikrein 6 in glioblastoma," Neuro Oncol., 15(3):305-318, Epub Jan. 10, 2013.
Drucker et al., "Prognostic significance of multiple kallikreins in high-grade astrocytoma," BMC Cancer, 15:565, Aug. 1, 2015, 9 pages.
Dubois-Dalcq et al., "Enhancing central nervous system remyelination in multiple sclerosis," Neuron, 48(1):9-12, Oct. 6, 2005.
Duncan et al., "Extensive remyelination of the CNS leads to functional recovery," Proc. Natl. Acad. Sci. USA, 106(16):6832-6836, Apr. 21, 2009.
Eischen et al., "Comparison of Apoptosis in Wild-Type and Fas-Resistant Cells: Chemotherapy-Induced Apoptosis is not dependent on Fas/Fas Ligand Interactions," Blood, 1997, 90:935-943.
Fancy et al., "Myelin regeneration: a recapitulation of development?" Annu Rev Neurosci., 34:21-43, 2011.
Fern et al., "Rapid ischemic cell death in immature oligodendrocytes: a fatal glutamate release feedback loop," J Neurosci., 20(1):34-42, Jan. 1, 2000.
Fire et al., "Potent and specific genetic interference by double-stranded RNA in Caenorhabditis elegans," Nature, 391(6669):806-811, Feb. 19, 1998.
Franklin et al., "Remyelination in the CNS: from biology to therapy," Nat. Rev. Neuroscience, 9(11):839-855, Nov. 2008.
Franklin, "Why does remyelination fail in multiple sclerosis?" Nat Rev Neurosci., 3(9):705-714, Sep. 2002.
Friedmann et al., "T cell-mediated neuroprotection involves antithrombin activity," J Neuroimmunol., 121(1-2):12-21, Dec. 3, 2001.
Fulmer et al., "Astrocyte-derived BDNF supports myelin protein synthesis after cuprizone-induced demyelination," J. Neuroscience, 34(24):8186-8196, Jun. 11, 2014.
Funfschilling et al., "Glycolytic oligodendrocytes maintain myelin and long-term axonal integrity," Nature, 485(7399):517-521, Apr. 29, 2012.
Fyffe-Maricich et al., "Signaling through ERK1/2 controls myelin thickness during myelin repair in the adult central nervous system," J Neurosci., 33(47):18402-18408, Nov. 20, 2013.
Fyffe-Maricich et al., "The ERK2 mitogen-activated protein kinase regulates the timing of oligodendrocyte differentiation," J Neurosci., 31(3):843-850, Jan. 19, 2011.
Gao et al., "Nicotine modulates neurogenesis in the central canal during experimental autoimmune encephalomyelitis," Neuroscience, 297:11-21, Mar. 23, 2015.
GenBank Accession No. AF013988, "*Homo sapiens* serine protease mRNA, complete cds," May 20, 2008, 2 pages, accessed Mar. 14, 2013.
GenBank Accession No. AF016239, "Rhodotorula mucilaginosa protein synthesis elongation factor 1-alpha (tef1) gene, partial cds," Sep. 1999, 2 pages, accessed Mar. 14, 2013.
GenBank Accession No. AF149289, "*Homo sapiens* kallikrein-like serine protease gene, complete cds," Jun. 2000, 4 pages, accessed Mar. 14, 2013.
GenBank Accession No. D78203, "*Homo sapiens* mRNA for neurosin, complete cds," Feb. 1999, 2 pages, accessed Mar. 14, 2013.
GenBank Accession No. NM_002257, "*Homo sapiens* kallikrein 1 (KLK1), mRNA," Apr. 17, 2013, 4 pages.
GenBank Accession No. NM_019175.1, "Rattus norvegicus kallikrein related-peptidase 6 (Klk6), mRNA," Feb. 21, 2013, accessed Mar. 14, 2013.
GenBank, Accession No. NM_002774, "*Homo sapiens* kallikrein-related peptidase 6 (KLK6), transcript variant A, mRNA," Nov. 4, 2012, 5 pages.
Gessler et al. Neuroscience, 2010; 165:1312-1322.

Gingrich et al., "Serine proteases and brain damage—is there a link?" Trends Neurosci., 23(9):399-407, Sep. 2000.
Gonzalez-Perez et al., "Oligodendrogenesis in the subventricular zone and the role of epidermal growth factor," Brain Res. Reviews, 67(1-2):147-156, Jun. 24, 2011.
Gu et al., Exp. Physiol. 2012; 97.4:534-543. D01:10.1113/expphysiol. 2011.060764.
Guardiola-Diaz et al., "Erk1/2 MAPK and mTOR signaling sequentially regulates progression through distinct stages of oligodendrocyte differentiation," Glia., 60(3):476-486, Epub Dec. 5, 2011.
Guo et al., J. Neurosci. 2013; 33:6181-6190.
Haider et al., "The topograpy of demyelination and neurodegeneration in the multiple sclerosis brain," Brain, 139(Pt 3):807-815, Feb. 8, 2016.
Hamill et al., "Protease-activated receptor 1-dependent neuronal damage involves NMDA receptor function," Exp Neurol., 217(1):136-146, Epub Feb. 10, 2009.
Han et al., "Activation of protease activated receptor 1 increases the excitability of the dentate granule neurons of hippocampus," Mol Brain., 4:32, Aug. 10, 2011.
Han et al., "Proteomic analysis of active multiple sclerosis lesions reveals therapeutic targets," Nature, 451(7182):1076-1081, Epub Feb. 17, 2008.
Hannun, "Apoptosis and the dilemma of cancer chemotherapy," Blood, 89(6):1845-1853, Mar. 15, 1997.
Harrington et al., "Oligodendrocyte PTEN is required for myelin and axonal integrity, not remyelination," Ann Neurol., 68(5):703-716, Nov. 2010.
Henkaus et al., "Kallikrein 6 is a mediator of K-RAS-dependent migration of colon carcinoma cells," Biological Chem., 2008, 389:757-764.
Hibbits et al., "Astrogliosis during acute and chronic cuprizone demyelination and implications for remyelination," ASN Neuro, 4(6):393-408, Oct. 30, 2012.
Hogberg et al., "Toward a 3D model of human brain development for studying gene/environment interactions," Stem Cell Res. Therapy, 4(Suppl 1):S4, Dec. 20, 2013, 7 pages.
Huang et al., "Retinoid X receptor gamma signaling accelerates CNS remyelination," Nat Neurosci., 14(1):45-53, Epub Dec. 5, 2010.
Huang et al., "The role of growth factors as a therapeutic approach to demyelinating disease," Exp. Neurology, 283(Pt B):531-540, Sep. 2016.
Hyrup et al., "Peptide nucleic acids (PNA): synthesis, properties and potential applications," Bioorg Med Chem., 4(1):5-23, Jan. 1996.
Irvine et al., "Remyelination protects axons from demyelination-associated axon degeneration," Brain, 131(Pt 6):1464-1477, Jun. 2008.
Ishii et al., "ERK1/ERK2 MAPK signaling is required to increase myelin thickness independent of oligodendrocyte differentiation and initiation of myelination," J Neurosci., 32(26):8855-8864, Jun. 27, 2012.
Ishii et al., "Sustained activation of ERK1/2 MAPK in oligodendrocytes and schwann cells enhances myelin growth and stimulates oligodendrocyte progenitor expansion," J Neurosci., 33(1):175-186, Jan. 2, 2013.
Jablonska et al., "Chordininduced lineage plasticity of adult SVZ neuroblasts after demyelination," Nat. Neuroscience, 13(5):541-550, May 2010.
Juliet et al., "Toxic effect of blood components on perinatal rat subventricular zone cells and oligodendrocyte precursor cell proliferation, differentiation and migration in culture," J Neurochem., 109(5):1285-1299, Epub Mar. 25, 2009.
Jung et al., "Lines of murine oligodendroglial precursor cells immortalized by an activated neu tyrosine kinase show distinct degrees of interaction with axons in vitro and in vivo," Eur J Neurosci., 7(6):1245-1265, Jun. 1, 1995.
Junge et al., "Protease-activated receptor-1 in human brain: localization and functional expression in astrocytes," Exp Neurol., 188(1):94-103, Jul. 2004.
Kang et al., "Degeneration and impaired regeneration of gray matter oligodendrocytes in amyotrophic lateral sclerosis," Nat. Neuroscience, 16(5):571-579, Mar. 31, 2013.

(56) References Cited

OTHER PUBLICATIONS

Kang et al., "NG2+ CNS glial progenitors remain committed to the oligodendrocyte lineage in postnatal life and following neurodegeneration," Neuron, 68(4):668-681, Nov. 18, 2010.
Keirstead et al., "Identification of post-mitotic oligodendrocytes incapable of remyelination within the demyelinated adult spinal cord," J Neuropathol Exp Neurol., 56(11):1191-1201, Nov. 1997.
Kennerdell and Carthew, "Use of dsRNA-mediated genetic interference to demonstrate that frizzled and frizzled 2 act in the wingless pathway," Cell., 95(7):1017-1026, Dec. 23, 1998.
Kipp et al., "Endogeneous remyelination: findings in human studies," CNS Neurol. Disord. Drug Targets, 11(5):598-609, Aug. 2012.
Klucky et al., "Kallikrein 6 induces e-cadherin shedding and promotes cell proliferation, migration, and invasion," Cancer Res., 67:8198-8206, Sep. 2007.
Kotter et al., "Myelin impairs CNS remyelination by inhibiting oligodendrocyte precursor cell differentiation," J. Neuroscience, 26(1):328-332, Jan. 4, 2006.
Kremer et al., "Pushing Forward: Remyelination as the New Frontier in CNS Diseases," Trends Neuroscience, 39(4):246-263, Mar. 7, 2016.
Kremer et al., "The complex world of oligodendroglial differentiation inhibitors," Ann Neurol., 69(4):602-618, Apr. 2011.
Kuhlmann et al., "Differentiation block of oligodendroglial progenitor cells as a cause for remyelination failure in chronic multiple sclerosis," Brain, 131(Pt 7):1749-1758, Epub May 30, 2008.
Kutzelnigg et al., "Cortical demyelination and diffuse white matter injury in multiple sclerosis," Brain, 128(Pt 11):2705-2712, Nov. 2005.
Lacroix et al., "Central canal ependymal cells proliferate extensively in response to traumatic spinal cord injury but not demyelinating lesions," PLoS One, 9(1):e85916, Jan. 27, 2014, 11 pages.
Laxmikanthan et al., "1.70 Å X-Ray Structure of Human apo Kallikrein 1: Structural Changes Upon Peptide Inhibitor/Substrate Binding," Proteins, 2005, 58:802-814.
Lee at al., "Protease and Protease-Activated Receptor-2 Signaling in the Pathogenesis of Atopic Dermatitis," Yonsei. Med. J., 51(6): 808-822, Nov. 2010.
Li et al., "Females remyelinate more efficiently than males following demyelination in the aged but not young adult CNS," Exp. Neurology, 202(1):250-254, Nov. 2006.
Ligon et al., "Olig gene function in CNS development and disease," Glia., 54(1):1-10, Jul. 2006.
Lohman et al., "Antagonism of Protease-Activated Receptor 2 Protects Against Experimental Colitis," Pharmacol. Exp. Ther., 340(2):256-265, Oct. 2011.
Lohman et al., "An Antagonist of Human Protease Activate Receptor—2 Attenuates PAR2 Signaling, Macrophage Activation, Mast Cell Degranulation, and Collage-Induced Arthritis in Rats," FASEB J., 26(7):2877-2887, Mar. 2012.
Lou et al., "Correlation between KLK6 expression and the clinicopathological features of glioma," Contemp. Oncol., 18(4):246-251, Aug. 2014.
Lubetzki et al., "Demyelination in multiple sclerosis," Handb. Clin. Neurology, 122:89-99, Feb. 5, 2014.
Lucchinetti et al., "Inflammatory cortical demyelination in early multiple sclerosis," N. Engl. J. Medicine, 365(23):2188-2197, Dec. 8, 2011.
Lundwall et al., "A comprehensive nomenclature for serine proteases with homology to tissue kallikreins," Biol Chem., 387(6):637-641, Jun. 2006.
Luo et al., "Protease-activated receptors in the brain: receptor expression, activation, and functions in neurodegeneration and neuroprotection," Brain Res Rev., 56(2):331-345, Epub Aug. 29, 2007.
Lyden et al., "Direct thrombin inhibitor argatroban reduces stroke damage in 2 different models," Stroke, 45(3):896-899, Mar. 2014.
Machida, Ed., Viral Vectors for Gene Therapy: Methods and Protocols, Humana Press, 2003, 6 pages (Table of Contents Only).
Mandal et al. "Tissue Factor Trafficking in Fibroblasts: involvement of Protease-Activated Receptor-Mediated Cell Signaling," Blood, 110(1):161-170, Jul. 2007.
Marks et al. "Clarifying Stem-Cell Therapy's Benefits and Risks", N Engl J Med. Mar. 16, 2017;376(11):1007-1009 (Year: 2017).
Mason et al., "Insulin-like growth factor (IGF) signaling through type 1 IGF receptor plays an important role in remyelination," J. Neuroscience, 23(20):7710-7718, Aug. 20, 2003.
Matsushima et al., "The neurotoxicant, cuprizone, as a model to study demyelination and remyelination in the central nervous system," Brain Pathology, 11(1):107-116, Jan. 2001.
Matute et al., "P2X(7) receptor blockade prevents ATP excitotoxicity in oligodendrocytes and ameliorates experimental autoimmune encephalomyelitis," J Neurosci., 27(35):9525-9533, Aug. 29, 2007.
McCarthy and de Vellis, "Preparation of separate astroglial and oligodendroglial cell cultures from rat cerebral tissue," J Cell Biol., 85(3):890-902, Jun. 1980.
McMorris et al., "Regulation of oligodendrocyte development by insulin-like growth factors and cyclic nucleotides," Ann. NY Acad. Sciences, 605:101-109, 1990.
Menn et al., "Origin of oligodendrocytes in the subventricular zone of the adult brain," J. Neuroscience, 26(30):7907-7918, Jul. 26, 2006.
Mi et al., "LINGO-1 antagonist promotes spinal cord remyelination and axonal integrity in MOG-induced experimental autoimmune encephalomyelitis," Nat. Medicine, 13(10):1228-1233, Oct. 2007.
Mi et al., "LINGO-1 negatively regulates myelination by oligodendrocytes," Nat. Neuroscience, 8(6):745-751, Jun. 2005.
Mi et al., "Promotion of central nervous system remyelination by induced differentiation of oligodendrocyte precursor cells," Ann. Neurology, 65(3):304-315, Mar. 2009.
Mifsud et al., "Oligodendrocyte pathophysiology and treatment strategies in cerebral ischemia," CNS Neurosci Ther., 20(7):603-612, Epub Apr. 7, 2014.
Misquitta and Paterson, "Targeted disruption of gene function in Drosophila by RNA interference (RNA-i): a role for nautilus in embryonic somatic muscle formation," Proc Natl Acad Sci U S A., 96(4):1451-1456, Feb. 16, 1999.
Miyamoto et al., "Astrocytes Promote Oligodendrogenesis after White Matter Damage via Brain-Derived Neurotrophic Factor," J. Neuroscience, 35(41):14002-14008, Oct. 14, 2015.
Morgan, Ed., Gene Therapy Protocols (Methods in Molecular Medicine), Humana Press, 2002, 3 pages (Table of Contents Only).
Mothe et al., "Isolation of Neural Stem/Progenitor Cells from the Periventricular Region of the Adult Rat and Human Spinal Cord," J. Vis. Experiments, 99:e52732, May 14, 2015.
Murtie et al., "PDGF and FGF2 pathways regulate distinct oligodendrocyte lineage responses in experimental demyelination with spontaneous remyelination," Neurobiol. Disease, 19(1-2):171-182, Jun./Jul. 2005.
Nait-Oumesmar et al., "Activation of the subventricular zone in multiple sclerosis: evidence for early glial progenitors," Proc. Natl. Acad. Sci. USA, 104(11):4694-4699, Mar. 13, 2007.
Nait-Oumesmar et al., "Progenitor cells of the adult mouse subventricular zone proliferate, migrate and differentiate into oligodendrocytes after demyelination," Eur. J. Neuroscience, 11(12):4357-4366, Dec. 1999.
Nasri et al. Am J. Physiol. Gastrointest. Liver Physiol., 2016; 311:G221-G236. doi:10.1152/ajpgi.00328.2015.
NCI Drug Dictionary, National Cancer Institute, arsenic trioxide [online], [retrieved Dec. 11, 2012] Retrieved from the internet <URL:http://www.cancer.gov/drugdictionary?CdrID=43067>, 1 page.
Nicole et al., "Activation of protease-activated receptor-1 triggers astrogliosis after brain injury," J Neurosci., 25(17):4319-4329, Apr. 27, 2005.
Nobuta et al., "STAT3-mediated astrogliosis protects myelin development in neonatal brain injury," Ann Neurol., 72(5):750-765, Epub Aug. 31, 2012.
Noorbakhsh et al., "Proteinase-Activated Receptor 2 Modulates Neuroinflammation in Experimental Autoimmune Encephalomyelitis and Multiple Sclerosis," The Journal of Experimental Medicine, 203(2):425-35, Feb. 2006.

(56) References Cited

OTHER PUBLICATIONS

Oikonomopoulou et al., "Kallikrein-mediated cell signalling: targeting proteinase-activated receptors (PARs)," Biol. Chemistry, 387(6):817-824, Jun. 2006.
Oikonomopoulou et al., "Proteinase-activated receptors, targets for kallikrein signaling," J Biol Chem., 281(43):32095-32112, Epub Aug. 2, 2006.
Oikonomopoulou et al., "Proteinase-mediated cell signalling: targeting proteinase-activated receptors (PARs) by kallikreins and more," Biol Chem., 387(6):677-685, Jun. 2006.
Oldstone et al., "Virus-induced alterations in homeostasis: alterations in differentiated functions of infected cells in vivo," Science, 218(4577):1125-1127, Dec. 10, 1982.
Olson et al., "PAR-1 deficiency protects against neuronal damage and neurologic deficits after unilateral cerebral hypoxia/ischemia," J Cereb Blood Flow Metab., 24(9):964-971, Sep. 2004.
Pampalakis et al., "Tissue kallikrein proteolytic cascade pathways in normal physiology and cancer," Biochem. Biophys. Acta, 1776:22-31, 2007.
Pang et al., "IGF-1 protects oligodendrocyte progenitors against TNFalpha-induced damage by activation of PI3K/Akt and interruption of the mitochondrial apoptotic pathway," Glia, 55(11):1099-1107, Aug. 15, 2007.
Panos et al., "Differential expression of multiple kallikreins in a viral model of multiple sclerosis points to unique roles in the innate and adaptive immune response," Biol. Chemistry, 395(9):1063-1073, Sep. 2014.
Papenfuss et al., "Sex differences in experimental autoimmune encephalomyelitis in multiple murine strains," J. Neuroimmunology, 150(1-2):59-69, May 2004.
Patrikios et al., "Remyelination is extensive in a subset of multiple sclerosis patients," Brain, 129(Pt 12):3165-3172, Dec. 2006.
Peterson et al., "Transected neurites, apoptotic neurons, and reduced inflammation in cortical multiple sclerosis lesions," Ann. Neurology, 50(3):389-400, Sep. 2001.
Picard-Riera et al., "Experimental autoimmune encephalomyelitis mobilizes neural progenitors from the subventricular zone to undergo oligodendrogenesis in adult mice," Proc. Natl. Acad. Sci. USA, 99(20):13211-13216, Oct. 1, 2002.
Praet et al., "Cellular and molecular neuropathology of the cuprizone mouse model: clinical relevance for multiple sclerosis," Neurosci. Biobehav. Reviews, 47:485-505, Nov. 2014.
Radulovic et al., "Targeting the thrombin receptor modulates inflammation and astrogliosis to improve recovery after spinal cord injury," Neurobiol. Disease, 93:226-242, May 1, 2016.
Radulovic et al., "Genetic targeting of protease activated receptor 2 reduces inflammatory astrogliosis and improves recovery of function after spinal cord injury," Neurobiol Dis., 83:75-89, Nov. 2015.
Raible et al., "Induction of oligodendrocyte differentiation by activators of adenylate cyclase," J. Neurosci. Research, 27(1):43-46, Sep. 1990.
Rajput et al., "Protease activated receptor-1 mediates cytotoxicity during ischemia using in vivo and in vitro models," Neuroscience, 281:229-240, Dec. 5, 2014.
Rasmussen et al., PLoS One, 2012; 7:e46087. doi:10.1371/journal.pone.0046087.
Riek-Burchardt et al., "Increase of prothrombin-mRNA after global cerebral ischemia in rats, with constant expression of protease nexin-1 and protease-activated receptors," Neurosci Lett., 329(2):181-184, Aug. 30, 2002.
Romano and Masino, "Quelling: transient inactivation of gene expression in Neurospora crassa by transformation with homologous sequences," Mol Microbiol., 6(22):3343-3353, Nov. 1992.
Saher et al., "Cholesterol: a novel regulatory role in myelin formation," Neuroscientist, 17(1):79-93, Feb. 2011.
Scarisbrick et al., "Activity of a newly identified serine protease in CNS demyelination," Brain, 125(Pt 6):1283-1296, Jun. 2002.
Scarisbrick et al., "Differential Expression of Brain-Derived Neurotrophic Factor, Neurotrophin-3, and Neurotrophin-4/5 in the Adult Rat Spinal Cord: Regulation by the Glutamate Receptor Agonist Kainic Acid," J. Neuroscience, 19(18):7757-7769, Sep. 15, 1999.
Scarisbrick et al., "Dynamic role of kallikrein 6 in traumatic spinal cord injury," Eur J Neurosci., 24(5):1457-1469, Sep. 2006.
Scarisbrick et al., "Functional role of kallikrein 6 in regulating immune cell survival," PLoS One., 6(3):e18376, Mar. 28, 2011.
Scarisbrick et al., "Kallikrein 6 is a novel molecular trigger of reactive astrogliosis," Biol Chem., 393(5):355-367, Apr. 2012.
Scarisbrick et al., "Kallikrein 6 regulates early CNS demyelination in a viral model of multiple sclerosis," Brain Pathol., 22(5):709-722, Epub Mar. 21, 2012.
Scarisbrick et al., "Kallikreins are associated with secondary progressive multiple sclerosis and promote neurodegeneration," Biol Chem., 389(6):739-745, Jun. 2008.
Scarisbrick et al., "MSP, a trypsin-like serine protease, is abundantly expressed in the human nervous system," J Comp Neurol., 431(3):347-361, Mar. 12, 2001.
Scarisbrick et al., "Nervous system-specific expression of a novel serine protease: regulation in the adult rat spinal cord by excitotoxic injury," J Neurosci., 17(21):8156-8168, Nov. 1, 1997.
Scarisbrick et al., "Neurotrophin-4/5 promotes proliferation of oligodendrocyte-type-2 astrocytes (O-2A)," Brain Res. Dev. Brain Research, 123(1):87-90, Sep. 30, 2000.
Scarisbrick et al., "Potential scope of action of tissue kallikreins in CNS immune-mediated disease," J Neuroimmunol., 178(1-2):167-176, Epub Jul. 7, 2006.
Scarisbrick et al., "Preferential expression of myelencephalon-specific protease by oligodendrocytes of the adult rat spinal cord white matter," Glia., 30(3):219-230, May 2000.
Scarisbrick, "The multiple sclerosis degradome: enzymatic cascades in development and progression of central nervous system inflammatory disease," Curr. Top. Microbiol. Immunology, 318:133-175, 2008.
Scolding et al., "Oligodendrocyte progenitors are present in the normal adult human CNS and in the lesions of multiple sclerosis," Brain, 121(Pt 12):2221-2228, Dec. 1998.
Sevigny et al., "Interdicting Protease-Activated Receptor-2-Driven Inflammation with Cell-Penetrating Pepducins," Proc. Natl. Acad. Sci, USA., 108(2):8491-8496, May 2011.
Sloane et al., "Hyaluronan blocks oligodendrocyte progenitor maturation and remyelination through TLR2," Proc. Natl. Acad. Sci. USA, 107(25):11555-11560, Jun. 22, 2010.
Smith et al., "Central remyelination restores secure conduction," Nature, 280(5721):395-396, Aug. 2, 1979.
Sotiropoulou et al., Abstract 4916: "Molecular basis for the concentration-dependent tumor suppressing effects of KLK6 in breast cancer," Canc. Res., 72(8), Supp. 1, Abstract No. 4916, Apr. 2012.
Striggow et al., "The protease thrombin is an endogenous mediator of hippocampal neuroprotection against ischemia at low concentrations but causes degeneration at high concentrations," Proc Natl Acad Sci U S A., 97(5):2264-2269, Feb. 29, 2000.
Su et al., "Inhibitory effect of KLK7 siRNA on gastric cancer AGS cell lines," Chinese J. Canc., Biother. 20(2):207-211, 2013 (Chinese with English abstract).
Substantive correspondence to and from the USPTO in U.S. Appl. No. 16/312,411, filed Jan. 14, 2021 to Dec. 9, 2021, 78 pages.
Suen et al., "Pathway-Selective Antagonism of Proteinase Activated Receptor 2," Brit. J. Pharmacol., 171(17):4112-4124, Apr. 2014.
Summerton and Weller, "Morpholino antisense oligomers: design, preparation, and properties," Antisense Nucleic Acid Drug Dev., 7(3):187-195, Jun. 1997.
Suo et al., "Participation of protease-activated receptor-1 in thrombin-induced microglial activation," J Neurochem., 80(4):655-666, Feb. 2002.
The factsheet of PAR2 KO mice: 004993—B6.Cg-F2rl1<tnn1Ms1b>/J from the Jackson laboratory website: www.jax.org/strain/004993 retrieved on Aug. 4, 2021.
Tripathi et al., "Prominent oligodendrocyte genesis along the border of spinal contusion lesions," Glia., 55(7):698-711, May 2007.

(56) References Cited

OTHER PUBLICATIONS

Tsiperson et al., "Brain-derived neurotrophic factor deficiency restricts proliferation of oligodendrocyte progenitors following cuprizone-induced demyelination," ASN Neuro, 7(1):1759091414566878, Jan. 13, 2015, 11 pages.

Tung et al. J. Biol. Chem. 2012; 287:22497-22508.

Vandell et al., "Protease-activated receptor dependent and independent signaling by kallikreins 1 and 6 in CNS neuron and astroglial cell lines," J Neurochem., 107(3):855-870, Epub Sep. 6, 2008.

Volpe et al., "The developing oligodendrocyte: key cellular target in brain injury in the premature infant," Int J Dev Neurosci., 29(4):423-440, Epub Mar. 5, 2011.

Vondran et al., "BDNF+/− mice exhibit deficits in oligodendrocyte lineage cells of the basal forebrain," Glia, 58(7):848-856, May 2010.

Vu et al., "Domains specifying thrombin-receptor interaction," Nature, 353(6345):674-677, Oct. 17, 1991.

Wang et al. The Use of Stem Cells in Neural Regeneration: A Review of Current Opinion, Curr Stem Cell Res Ther. 2018;13(7):608-617 (Year: 2018).

Wang et al., "Expression of protease-activated receptors (PARs) in OLN-93 oligodendroglial cells and mechanism of PAR-1-induced calcium signaling," Neuroscience., 126(1):69-82, 2004.

Wang et al., "Four subtypes of protease-activated receptors, co-expressed in rat astrocytes, evoke different physiological signaling," Glia., 37(1):53-63, Jan. 2002.

Wang et al., "P2X7 receptor inhibition improves recovery after spinal cord injury," Nat Med., 10(8):821-827, Epub Jul. 18, 2004.

Wang et al., "Direct gene delivery of human tissue kallikrein reduces blood pressure in spontaneously hypertensive rats," J. Clin. Invest. 95:1710-1716, Apr. 1995.

Weiss et al., "Multipotent CNS stem cells are present in the adult mammalian spinal cord and ventricular neuroaxis," J. Neuroscience, 16(23):7599-7609, Dec. 1, 1996.

Wilkins et al., "Oligodendrocytes promote neuronal survival and axonal length by distinct intracellular mechanisms: a novel role for oligodendrocyte-derived glial cell line-derived neurotrophic factor," Journal of Neuroscience, 23(12):4967-74, Jun. 2003.

Wilson and Brophy, "Role for the oligodendrocyte cytoskeleton in myelination," J Neurosci Res., 22(4):439-448, Apr. 1989.

Wolswijk et al., "Chronic stage multiple sclerosis lesions contain a relatively quiescent population of oligodendrocyte precursor cells," J Neurosci., 18(2):601-609, Jan. 15, 1998.

Wrathall et al., "Myelin gene expression after experimental contusive spinal cord injury," J Neurosci., 18(21):8780-8793, Nov. 1, 1998.

Xia et al., "Kallikrein protects against ischemic stroke by inhibiting apoptosis and inflammation and promoting angiogenesis and neurogenesis," Human Gene Ther. 17:206-219, Feb. 2006.

Xing et al., "Adult neural precursor cells from the subventricular zone contribute significantly to oligodendrocyte regeneration and remyelination," J. Neuroscience, 34(42):14128-14146, Oct. 15, 2014.

Xu et al., "Repurposing Registered Drugs as Antagonists for Protease-Activated Receptor 2," J. Chem. Inf. Model., 55(10):2079-2084, Oct. 2015.

Yamamoto et al., Transgenic Res. 2012; 21 :743-755. doi 10.1007/s11248-011-9564-0.

Yang et al., "G protein-coupled receptor 37 is a negative regulator of oligodendrocyte differentiation and myelination," Nat. Communications, 7:10884, Mar. 10, 2016.

Yau et al. J. Med. Chem. 2013; 56:7477-7497. dx.doi.org/10.1021/0400638v.

Yau et al., "Potent Small Agonists of Protease Activated Receptor 2," ACS Med. Chem. Letters, 7(1):105-110, Nov. 30, 2015.

Ye et al., "Insulin-like growth factor-I ameliorates demyelination induced by tumor necrosis factor-alpha in transgenic mice," J. Neurosci. Research, 85(4):712-722, Mar. 2007.

Yoon et al. Glia, 2017; 65:2070-2086.

Yoon et al., "Interplay between exercise and dietary fat modulates myelinogenesis in the central nervous system," Biochim. Biophys. Acta, 1862(4):545-555, Jan. 26, 2016.

Yoon et al., "Kallikrein 6 signals through PAR1 and PAR2 to promote neuron injury and exacerbate glutamate neurotoxicity," J Neurochem., 127(2):283-298, Epub May 27, 2013.

Yoon et al., "The thrombin receptor is a critical extracellular switch controlling myelination," Glia, 63(5):846-859, Epub Jan. 27, 2015.

Yousef and Diamandis, "The new human tissue kallikrein gene family: structure, function, and association to disease," Endocr Rev., 22(2):184-204, Apr. 2001.

Zarghooni et al., "Decreased concentration of human kallikrein 6 in brain extracts of Alzheimer's disease patients," Clin Biochem., 35(3):225-231, May 2002.

Zeger et al., "Insulin-like growth factor type 1 receptor signaling in the cells of oligodendrocyte lineage is required for normal in vivo oligodendrocyte development and myelination," Glia, 55(4):400-411, Mar. 2007.

Zeng et al., Mediators of Inflammation, 2013; 140812. dx.doi.org/10.1155/2013/140812.

U.S. Appl. No. 16/312,411, filed Dec. 21, 2018, Hye-Sook Yoon, Published as U.S. 2019/0201454.

Barry et al., "Novel agonists and antagonists for human protease activated receptor 2," J. Med. Chem., Sep. 2010, 53(20):7428-7440.

D'Andrea et al., "Characterization of protease-activated receptor-2 immunoreactivity in normal human tissues," J. Histochem. Cytochem., Feb. 1998, 46(2):157-164.

Furusho et al., "Fibroblast growth factor receptor signaling in oligodendrocytes regulates myelin sheath thickness," J. Neurosci., May 2012, 32(19):6631-6641.

Hebb et al., "Human kallikrein 6 cerebrospinal levels are elevated in multiple sclerosis," Curr. Drug Discov. Technol., Jun. 2010, 7(2):137-140.

Ji et al., "Cyclic AMP controls BDNF-induced TrkB phosphorylation and dendritic spine formation in mature hippocampal neurons," Nat. Neurosci., Feb. 2005, 8(2):164-172.

Joshi et al., "Development and characterization of a novel, graded model of clip compressive spinal cord injury in the mouse: Part 1. Clip design, behavioral outcomes, and histopathology," J. Neurotrauma., Feb. 2002, 19(2):175-190, 28 pages.

Lavi et al., "Experimental models of multiple sclerosis," New York, NY: Springer, 2005, 6 pages (Table of Contents Only).

Radulovic et al., "Kallikrein cascades in traumatic spinal cord injury: in vitro evidence for roles in axonopathy and neuron degeneration," J. Neuropathol. Exp. Neurol., Nov. 2013, 72(11):1072-1089.

Schutzer et al., "Gray matter is targeted in first-attack multiple sclerosis," PLoS One, Sep. 2013, 8(9):e66117, 7 pages.

Simon et al., "The Orphan G Protein-coupled Receptor GPR17 Negatively Regulates Oligodendrocyte Differentiation via Gαi/o and Its Downstream Effector Molecules," J. Biol. Chem., Jan. 2016, 291(2):705-718.

Singh et al., "Gray matter-related proteins are associated with childhood-onset multiple sclerosis," Neurol. Neuroimmunol. Neuroinflamm., Oct. 2015, 2(5):e155, 12 pages.

Sriwai et al., "Distinctive G Protein-Dependent Signaling by Protease-Activated Receptor 2 (PAR2) in Smooth Muscle: Feedback Inhibition of RhoA by cAMP-Independent PKA," PLoS One, Jun. 2013, 8(6):e66743, 12 pages.

Wang et al., "Hematopoietic Tissue Factor—Protease-Activated Receptor 2 Signaling Promotes Hepatic Inflammation and Contributes to Pathways of Gluconeogenesis and Steatosis in Obese Mice," Am. J. Pathol., Feb. 2015, 185(2):524-535.

Yu et al., "Fas/FasL-mediated apoptosis and inflammation are key features of acute human spinal cord injury: implications for translational, clinical application," Acta Neuropathol., Dec. 2011, 122(6):747-761.

\* cited by examiner

Primary Oligodendrocytes

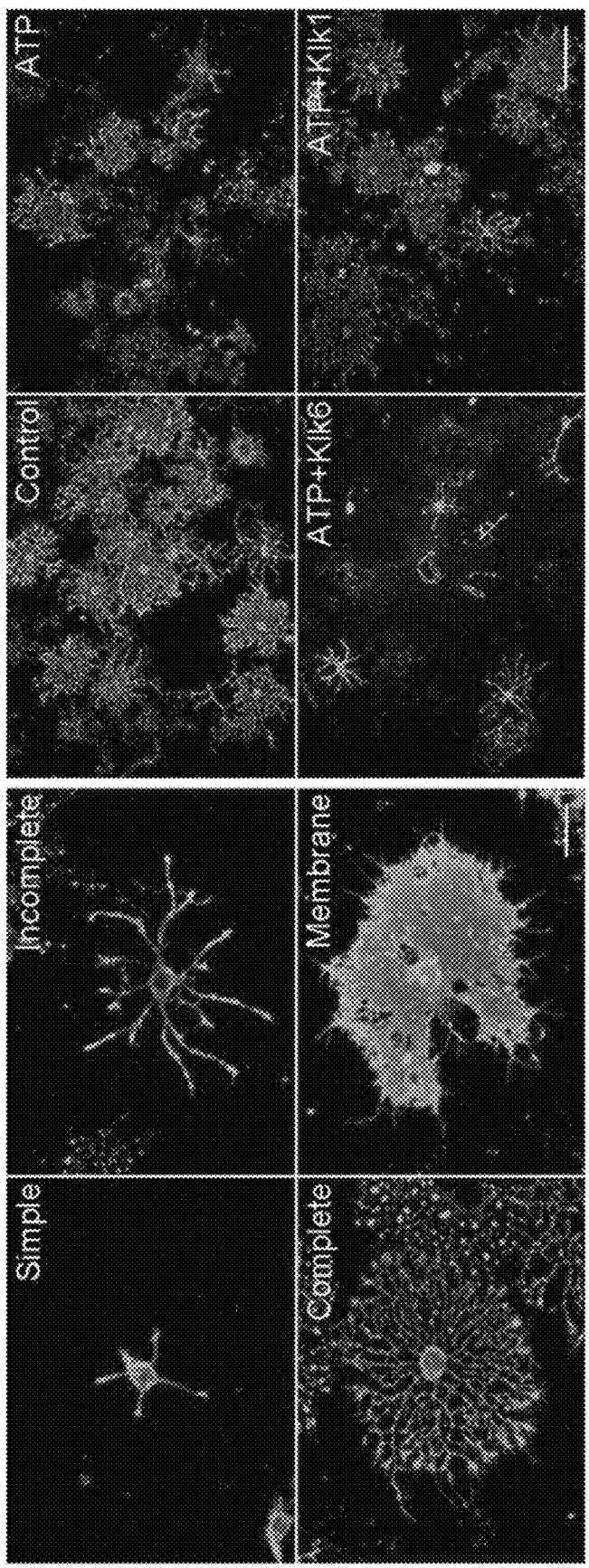

FIG. 4A
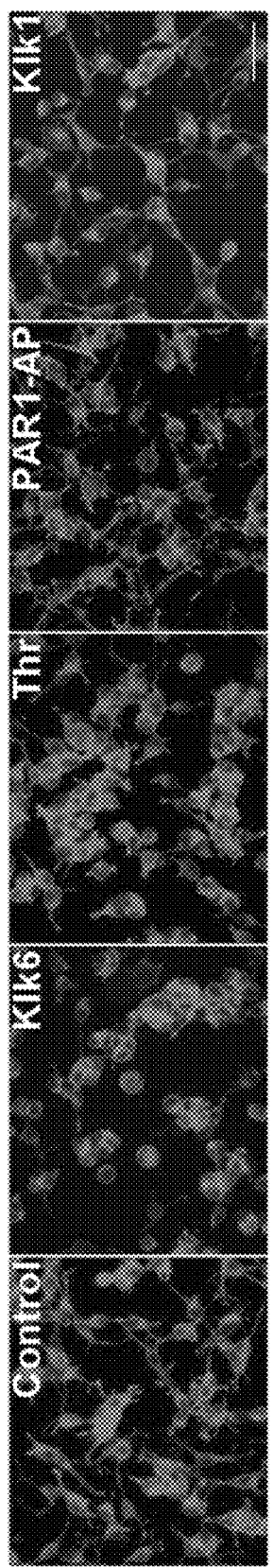
Oli-neu Oligodendrocytes
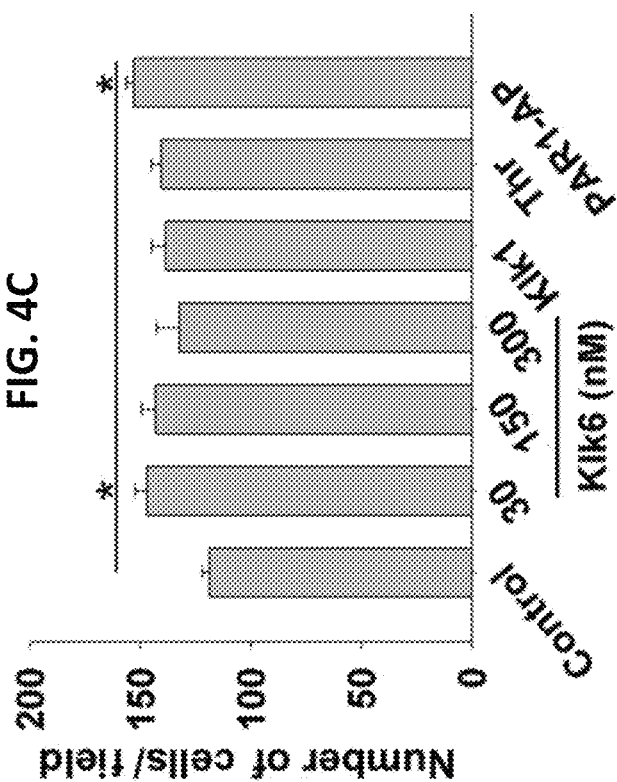
FIG. 4C
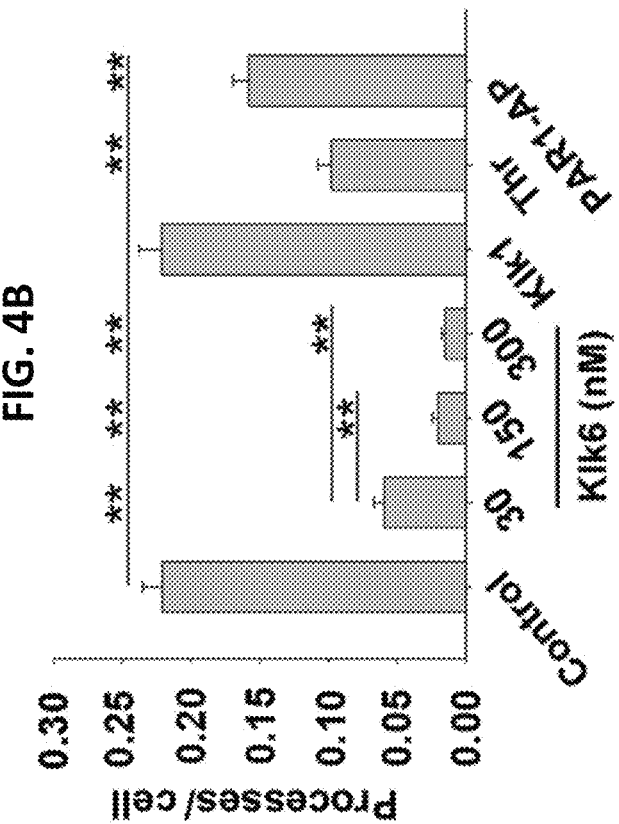
FIG. 4B

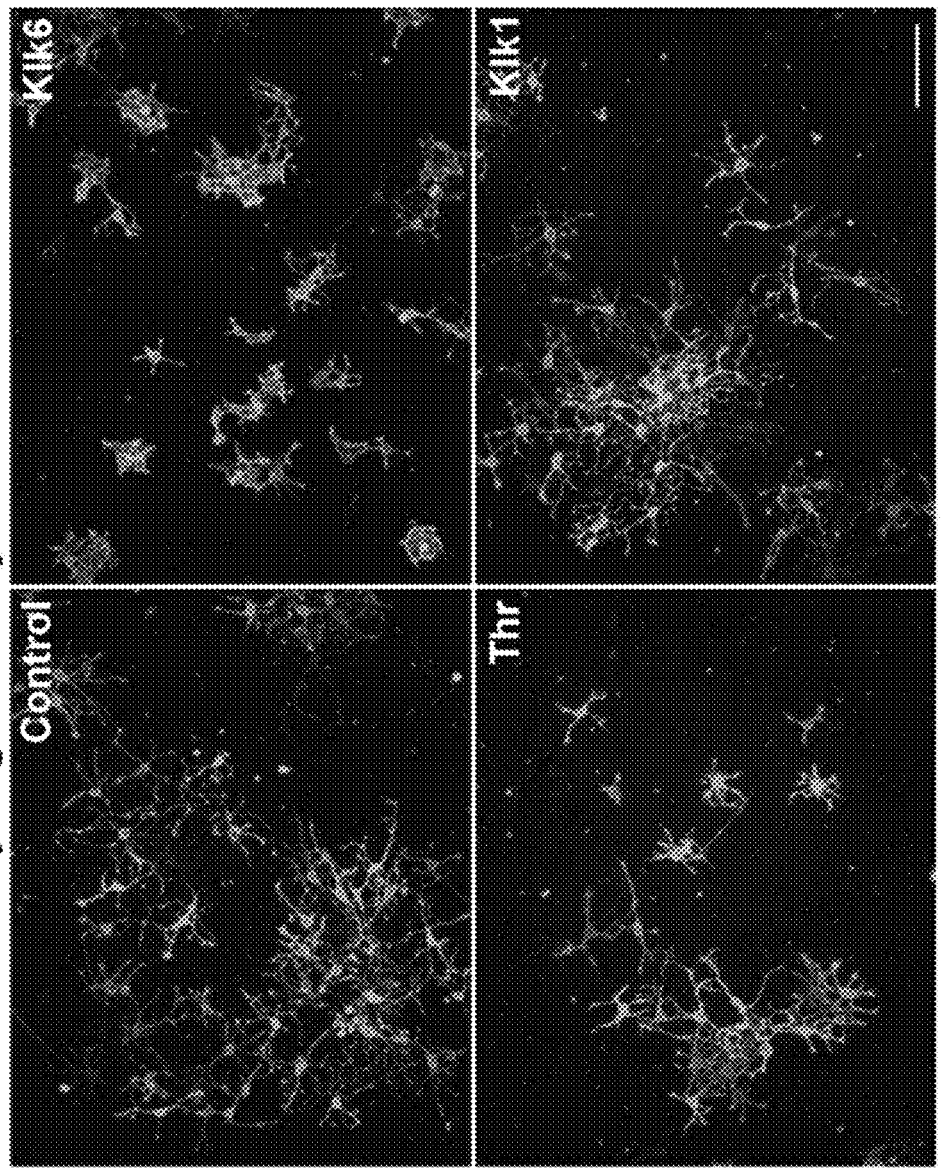
FIG. 5A
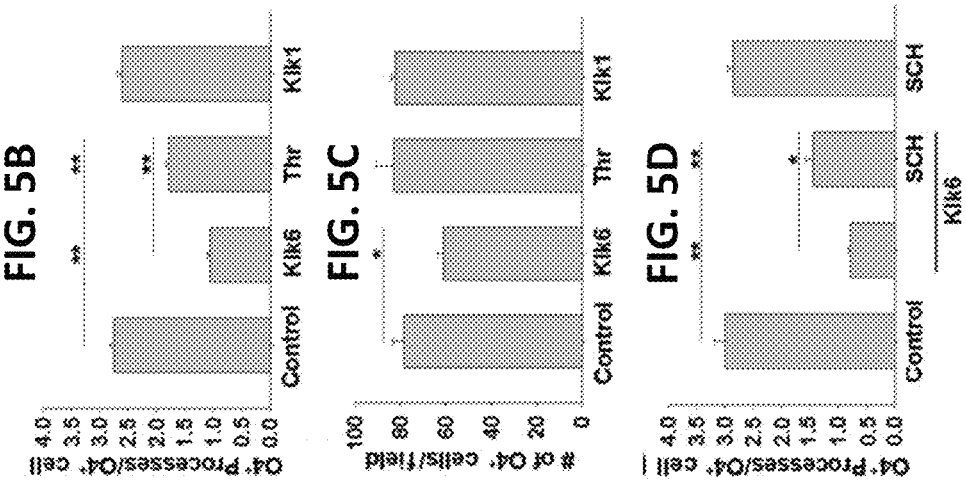

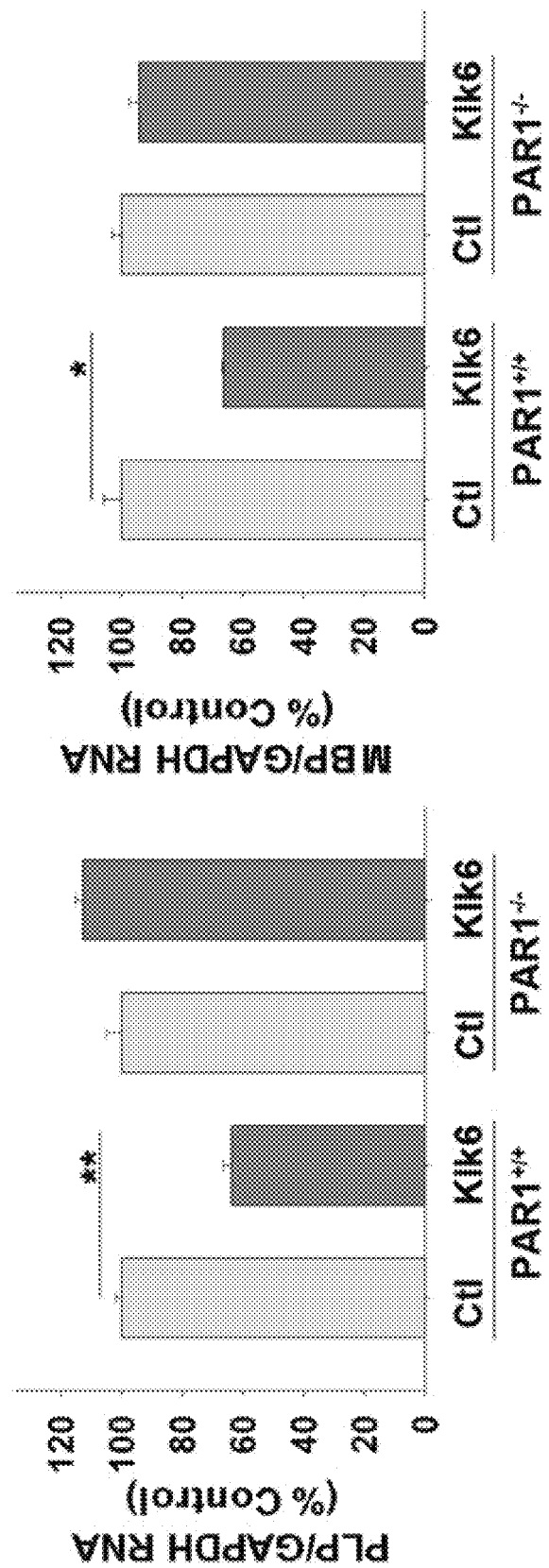

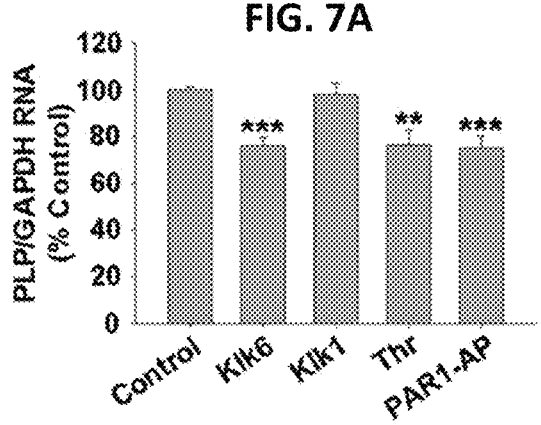
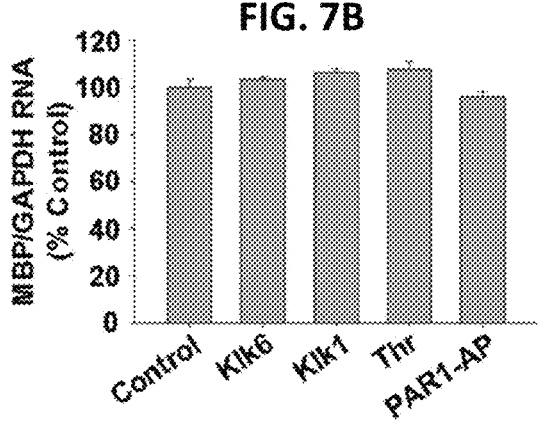
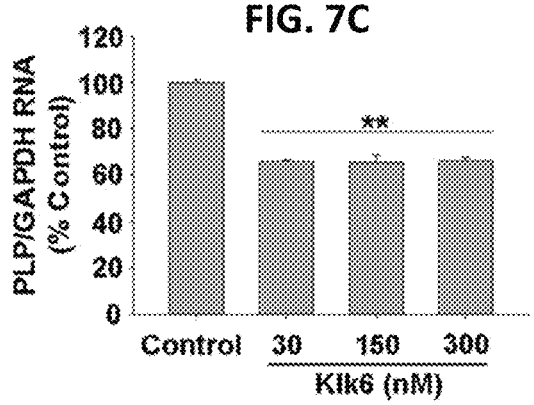
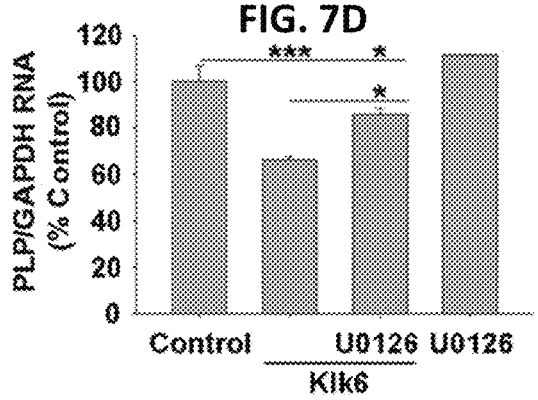
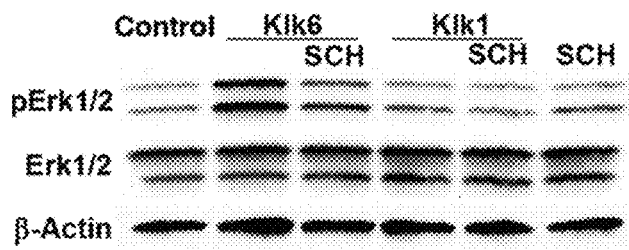
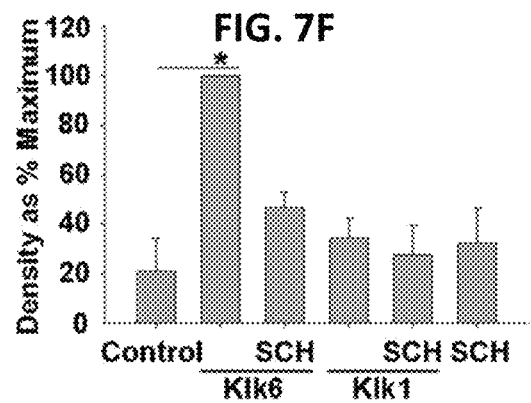

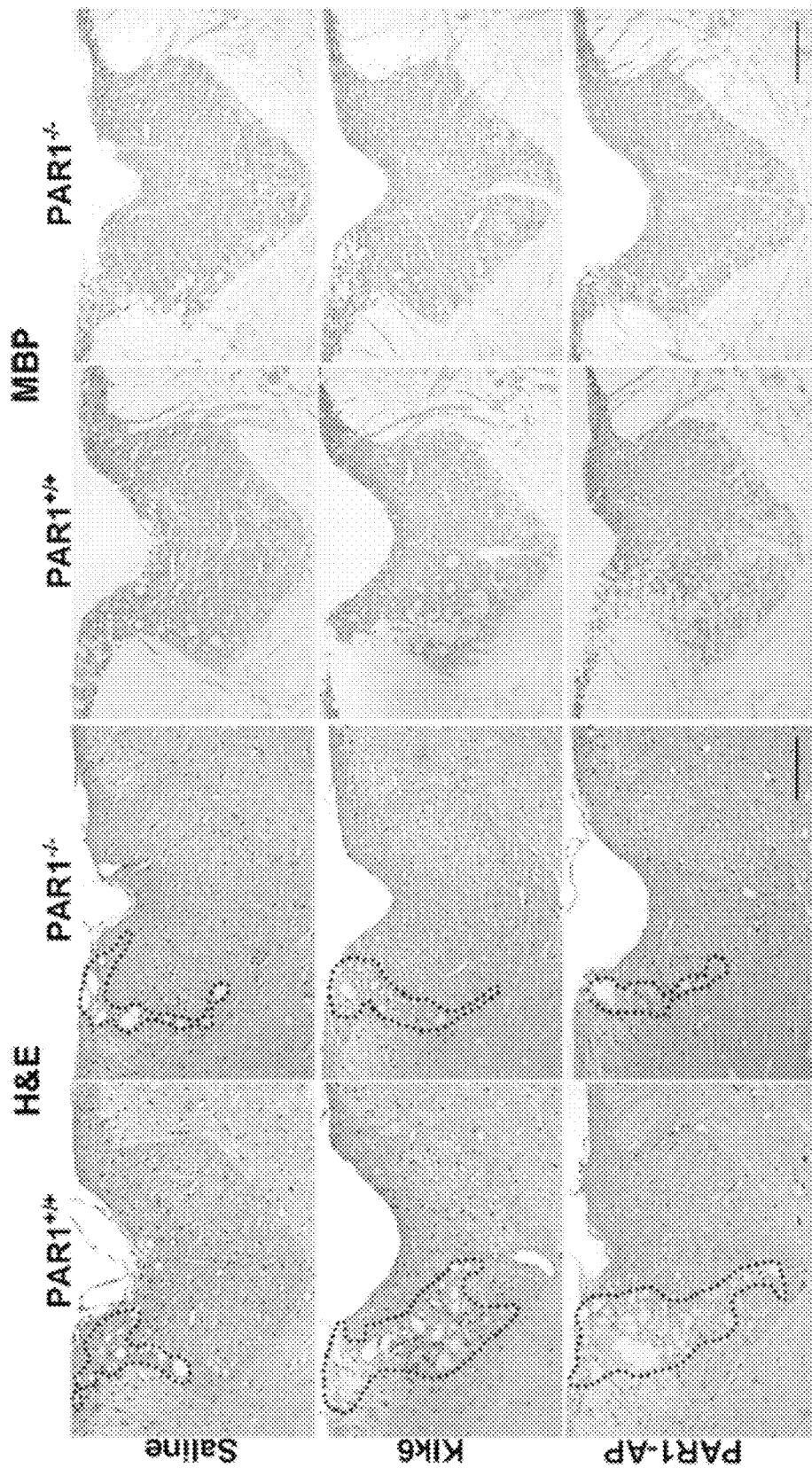

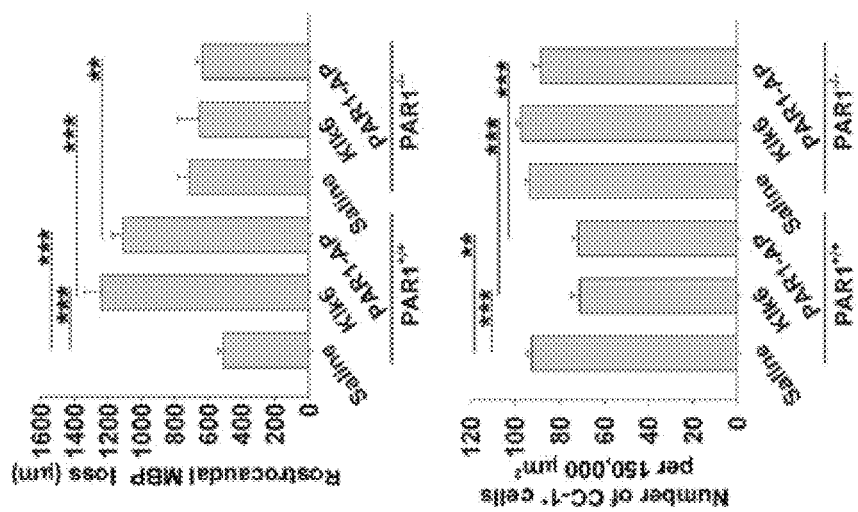
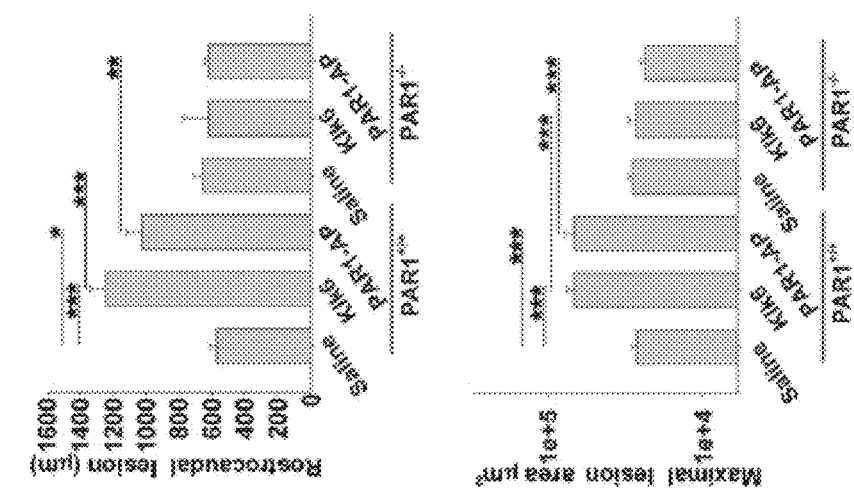
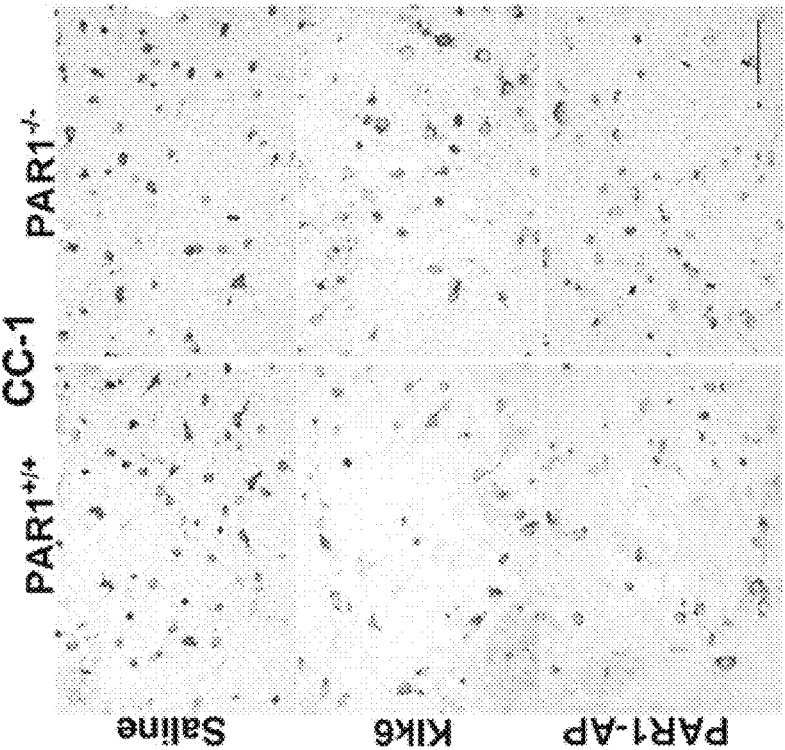
FIG. 8C, FIG. 8D, FIG. 8E, FIG. 8F, FIG. 8G

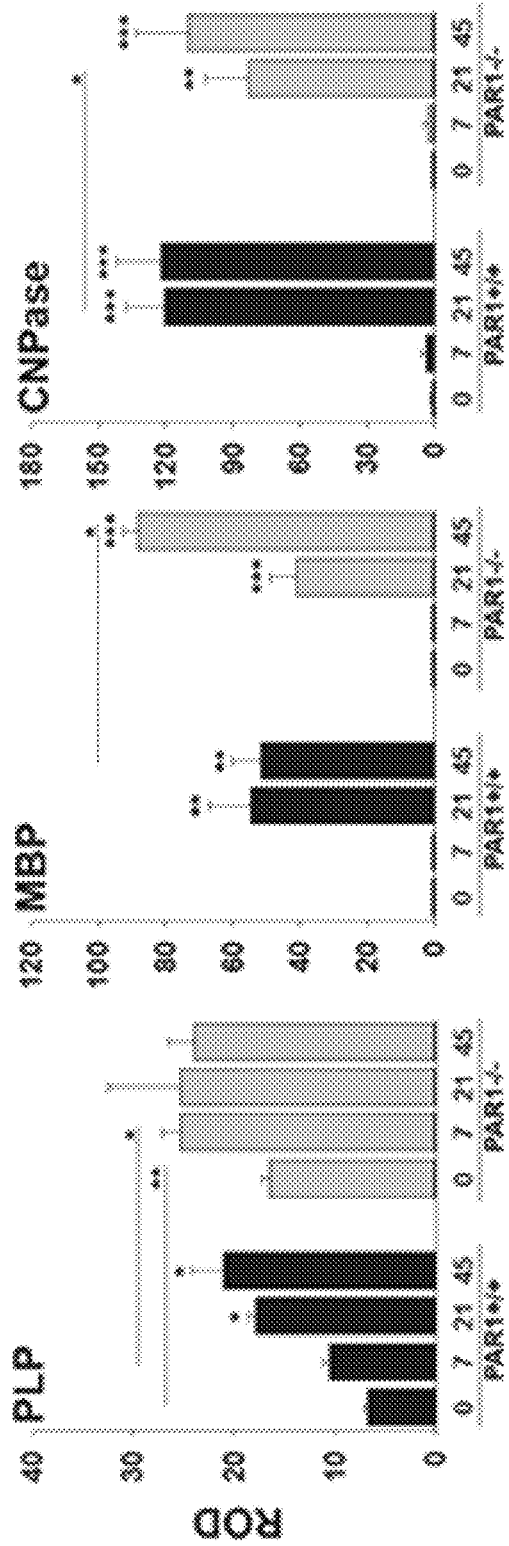
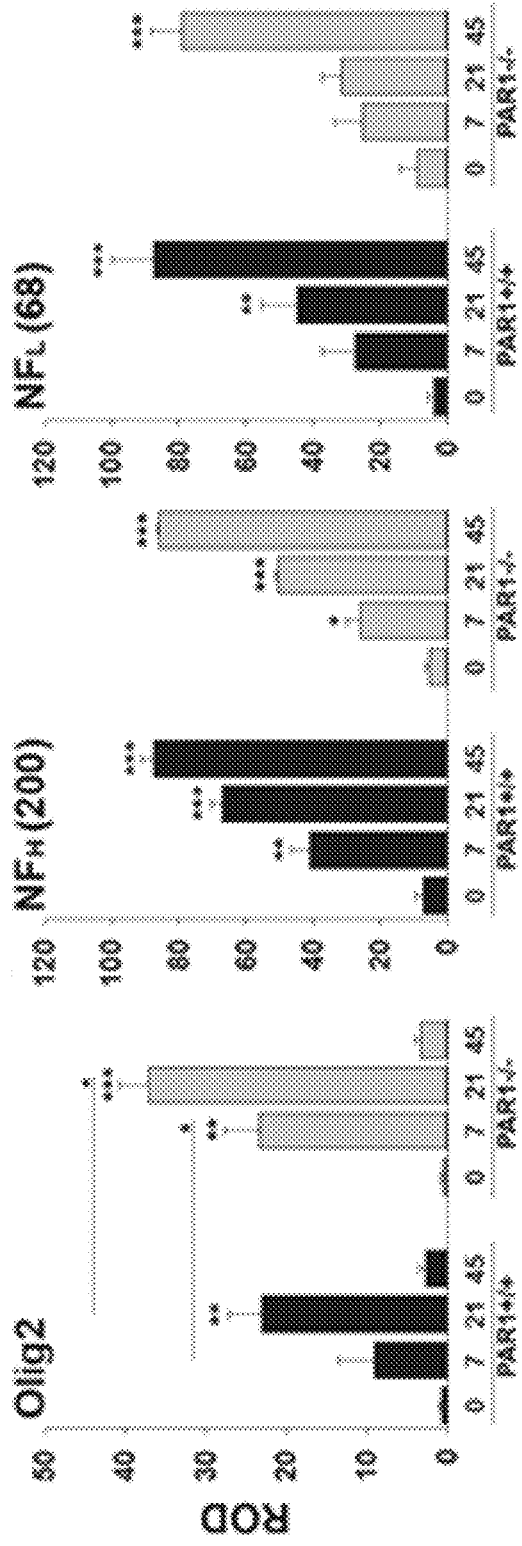

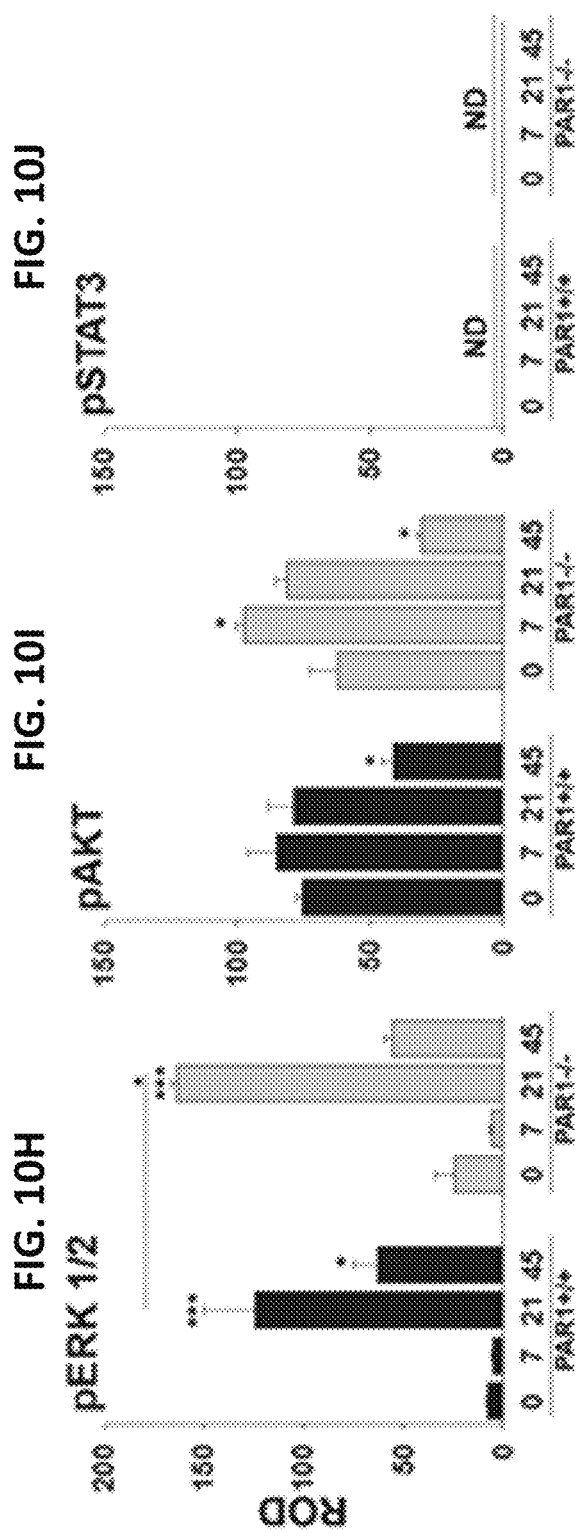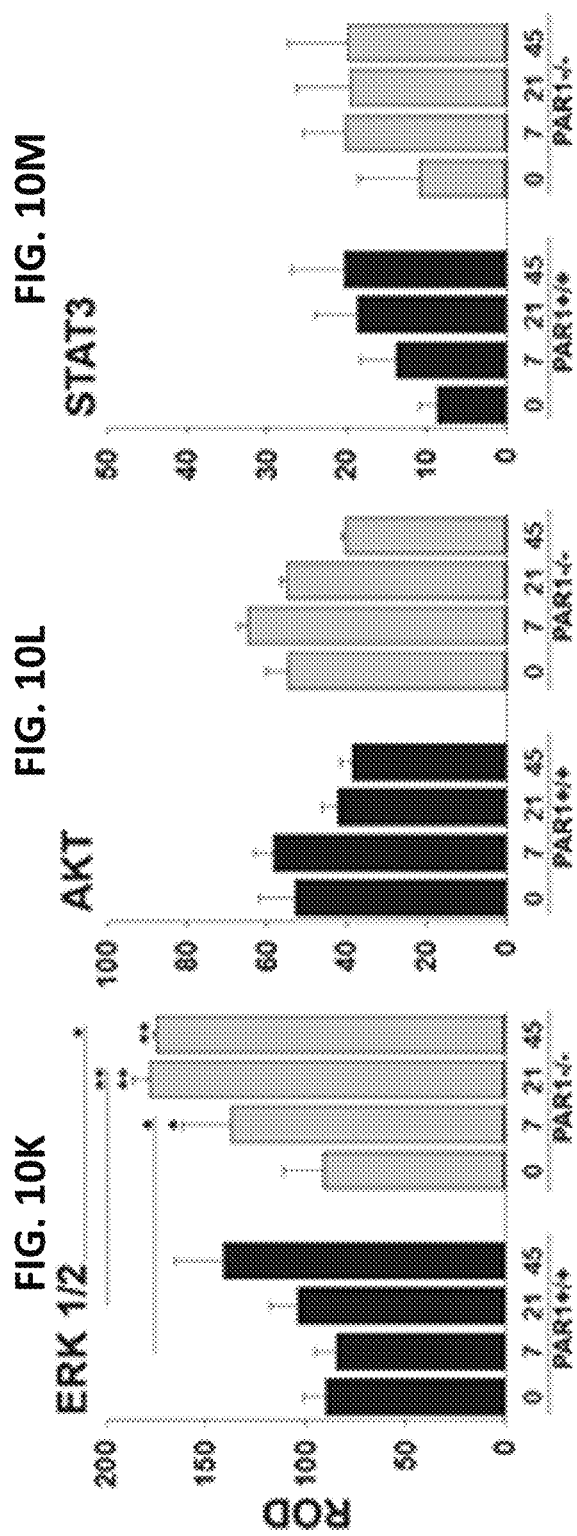

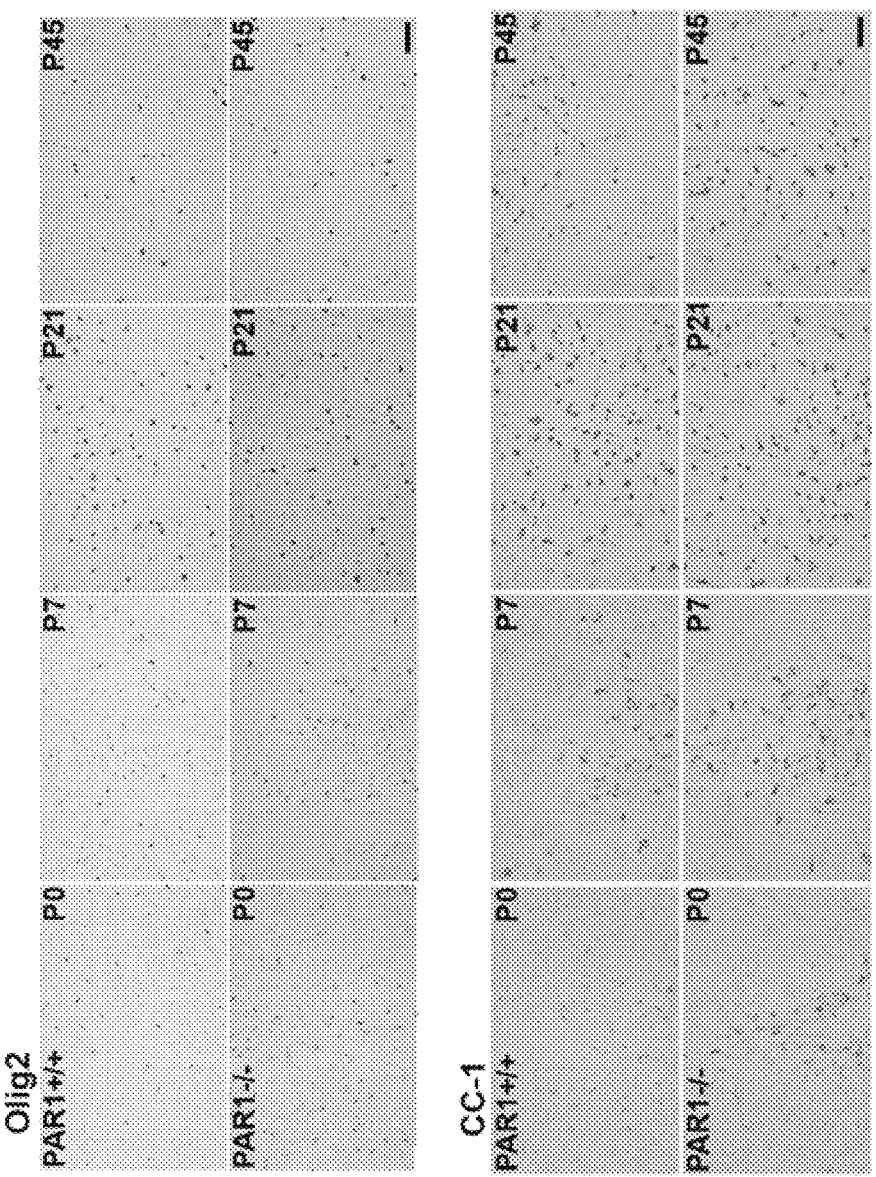
FIG. 11B
FIG. 11D
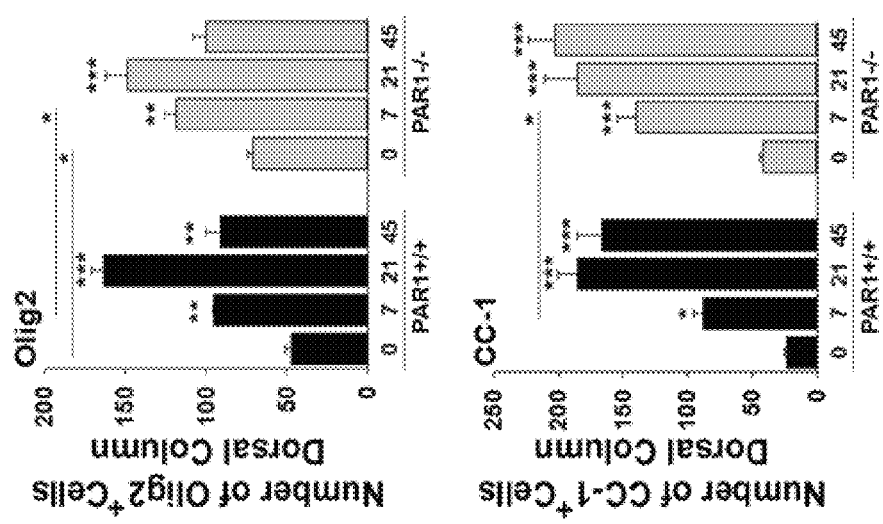
FIG. 11A
FIG. 11C

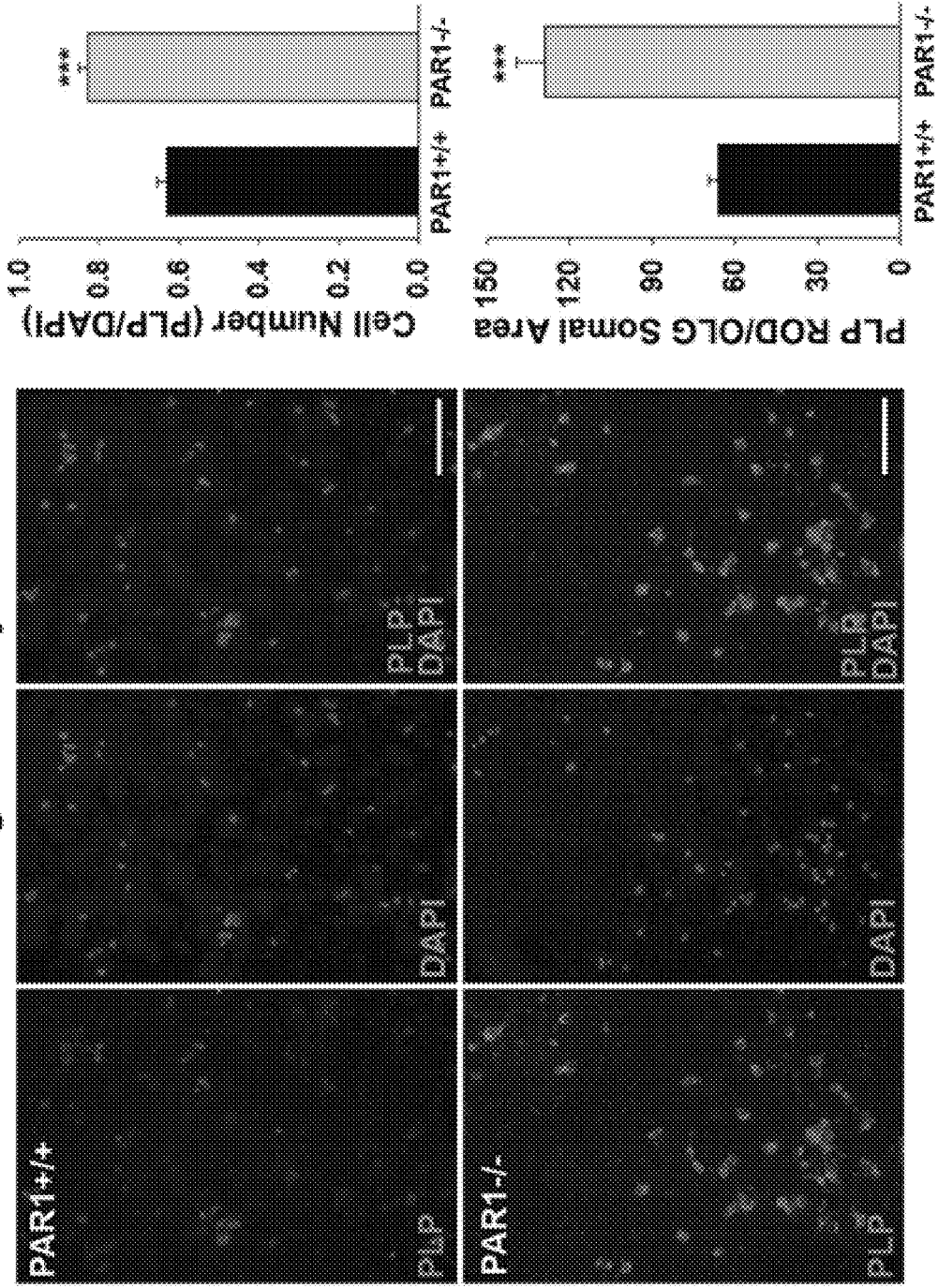

Number of Myelinated Nerve Fibers

Myelin Ultrastructure

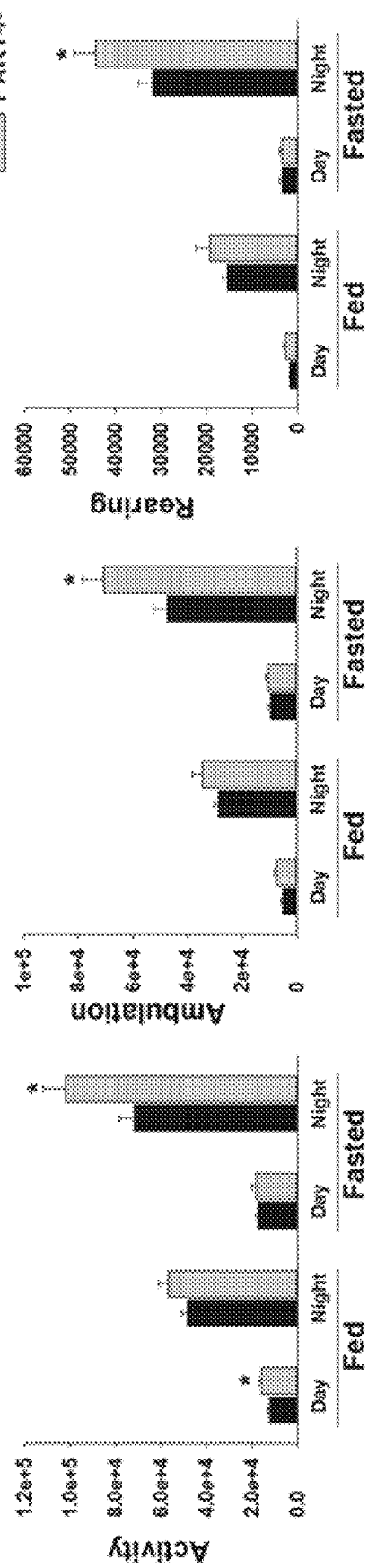

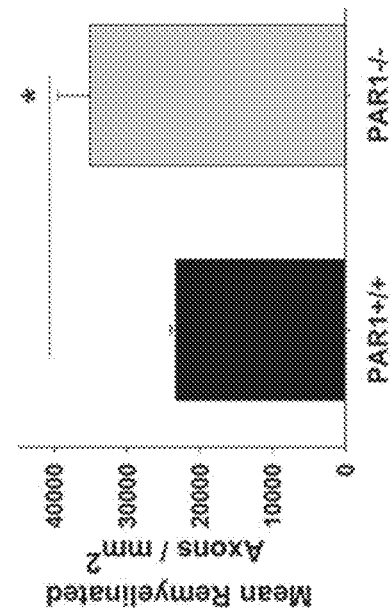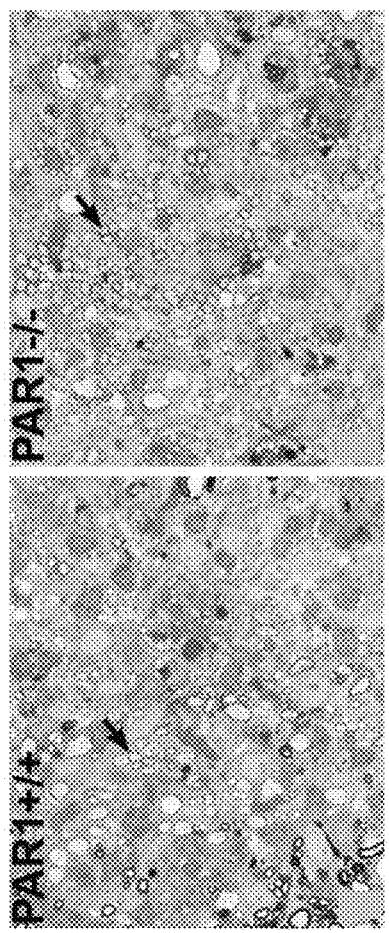

SEQUENCE LISTING

<160> NUMBER OF SEQ ID NOS: 21

<210> SEQ ID NO 1
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 1
accaccatgg agaaggc                                                    17

<210> SEQ ID NO 2
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 2
ggcatggact gtggtcatga                                                 20

<210> SEQ ID NO 3
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 3
cctaccctgg caagatcac                                                  19

<210> SEQ ID NO 4
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 4
ggatccatct gatatgagtg c                                               21

<210> SEQ ID NO 5
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 5
cttgctgatc gtcgccc                                                    17

<210> SEQ ID NO 6
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 6
ttcaccgtag catctgtcct                                                 20

<210> SEQ ID NO 7
<211> LENGTH: 17
<212> TYPE: DNA
<213> ORGANISM: Artificial Sequence

```
<220> FEATURE:
<223> OTHER INFORMATION: synthetically generated oligonucleotide

<400> SEQUENCE: 7
ccggaccgag aaccttg                                                  17

<210> SEQ ID NO 8
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 8
cggaagaaag acagtggtca g                                             21

<210> SEQ ID NO 9
<211> LENGTH: 26
<212> TYPE: DNA
<213> ORGANISM: Artificial Sequence
<220> FEATURE:
<223> OTHER INFORMATION: synthetically generated oligonucleotide

<400> SEQUENCE: 9
ccagtagtcc atttcttcaa gaacat                                        26

<210> SEQ ID NO 10
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 10
gccgatttat agtcggaagc tc                                            22

<210> SEQ ID NO 11
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 11
tctttggcga ctacaagacc ac                                            22

<210> SEQ ID NO 12
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 12
cacaaacttg tcgggatgtc cta                                           23

<210> SEQ ID NO 13
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 13
caaattctgt gactacggg                                                19
```

<210> SEQ ID NO 14
<211> LENGTH: 15
<212> TYPE: DNA
<213> ORGANISM: Artificial Sequence
<220> FEATURE:
<223> OTHER INFORMATION: synthetically generated oligonucleotide

<400> SEQUENCE: 14
ggccttgcca tacga                                                      15

<210> SEQ ID NO 15
<211> LENGTH: 26
<212> TYPE: DNA
<213> ORGANISM: Artificial Sequence
<220> FEATURE:
<223> OTHER INFORMATION: synthetically generated oligonucleotide

<400> SEQUENCE: 15
ccagtagtcc atttcttcaa gaacat                                          26

<210> SEQ ID NO 16
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 16
gccgatttat agtcggaagc tc                                              22

<210> SEQ ID NO 17
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 17
cttgctgatc gtcgccc                                                    17

<210> SEQ ID NO 18
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 18
ttcaccgtag catctgtcct                                                 20

<210> SEQ ID NO 19
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 19
tctttggcga ctacaagacc ac                                              22

<210> SEQ ID NO 20
<211> LENGTH: 23
<212> TYPE: DNA
<213> ORGANISM: Artificial Sequence
<220> FEATURE:
<223> OTHER INFORMATION: synthetically generated oligonucleotide

```
<400> SEQUENCE: 20
cacaaacttg tcgggatgtc cta                                              23

<210> SEQ ID NO 21
<211> LENGTH: 5
<212> TYPE: PRT
<213> ORGANISM: Artificial Sequence
<220> FEATURE:
<223> OTHER INFORMATION: synthetic

<400> SEQUENCE: 21

Thr Phe Leu Leu Arg
1               5
```

PAR1 MODULATION TO ALTER MYELINATION

CROSS-REFERENCE TO RELATED APPLICATIONS

This application is a continuation application of U.S. Ser. No. 16/776,215, filed Jan. 29, 2020 (abandoned), which is a continuation application of U.S. Ser. No. 15/815,274, filed Nov. 16, 2017 (abandoned), which is a continuation application of U.S. Ser. No. 14/793,244, filed Jul. 7, 2015 (abandoned), which claims benefit of priority from U.S. Provisional Application No. 62/021,566, filed on Jul. 7, 2014. The disclosures of the prior applications are considered part of (and are incorporated by reference in) the disclosure of this application.

STATEMENT AS TO FEDERALLY SPONSORED RESEARCH

This invention was made with government support under NS052741 awarded by the National Institutes of Health. The government has certain rights in the invention.

SEQUENCE LISTING

This application contains a Sequence Listing that has been submitted electronically as an ASCII text file named 07039-1376004.txt. The ASCII text file, created on Oct. 28, 2022, is 4,559 bytes in size. The material in the ASCII text file is hereby incorporated by reference in its entirety.

TECHNICAL FIELD

This document relates to materials and methods for modulating protease activated receptor 1 (PAR1) activity to alter myelination.

BACKGROUND

Myelination in the central nervous system is achieved through a delicate balance of extrinsic and intrinsic signaling mechanisms. Myelin not only enhances axonal conduction velocity, but also provides protection and trophic support (Wilkins et al., 2003). Normal myelination requires a series of well-orchestrated events, including the generation of oligodendrocyte progenitors (OPCs), migration of the OPCs to specific regions of the brain or spinal cord, and differentiation of the OCPs into oligodendrocytes that elaborate multilamellar sheaths of plasma membrane to myelinate axons in precise relation to their diameter. Aberrations in this process during the perinatal period can result in white matter injury and profound sensorimotor and cognitive disabilities. Multiple factors can disrupt the key developmental mileposts, including hemorrhagic-ischemic injuries (Mifsud et al., *CNS Neurosci Ther* 20:603-612, 2014; Crawford et al., *J Comp Pathol* 149:242-254, 2013; and Volpe et al., *Int J Devel Neurosci* 29:423-440, 2011).

SUMMARY

This document is based in part on elucidation of the role of PAR1 in regulating myelin gene expression, and the development of methods for targeting PAR1 to improve myelination and locomotor activity in vivo. As demonstrated by the data presented herein, PAR1 is a therapeutic target for improving myelination in the developing central nervous system. The methods disclosed herein can be used to prevent perinatal white matter injuries, and provide opportunities to improve both short and long term neurological functional outcomes.

In one aspect, this document features a method for modulating myelination in a mammal. The method can include (a) identifying the mammal as being in need of increased myelination, and (b) administering to the mammal an agent that reduces the activity of protease activated receptor 1 (PAR1). The agent can be an siRNA, an antisense nucleic acid molecule, an antibody against PAR1, or a small molecule inhibitor of PAR1. The mammal can be a human (e.g., a preterm infant, a child, an adolescent, or an adult). The mammal can be identified as having a central nervous system (CNS) demyelinating disease, CNS neuroinflammatory disease, or stroke, or a CNS injury.

In another aspect, this document features a method for treating a CNS demyelinating disorder in a mammal. The method can include administering to the mammal a composition comprising an agent that reduces the activity of PAR1, wherein the composition is administered in an amount effective to reduce or prevent demyelination, or to enhance remyelination. The agent can be an siRNA, an antisense nucleic acid molecule, an antibody against PAR1, or a small molecule inhibitor of PAR1. The mammal can be a human (e.g., a preterm infant, a child, an adolescent, or an adult). The CNS demyelinating disorder can be a CNS demyelinating disease, CNS neuroinflammatory disease, or stroke, or a CNS injury.

In another aspect, this document features a method for modulating myelination in a subject. The method can include delivering to the subject a plurality of modified stem cells that have reduced PAR expression as compared to corresponding wild type stem cells. The subject can be a human (e.g., an adult, adolescent, or child with a demyelinating disorder), or a preterm infant. The stem cells can be neural stem cells modified to have reduced PAR expression as compared to corresponding wild type neural stem cells. The modified neural stem cells can have a mutation in the PAR1 gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 3A and 3B are a series of photomicrographs and FIGS. 3C to 3F are a series of graphs showing that Klk6 reduces the maintenance of mature oligodendrocyte morphologies and exacerbates ATP-mediated toxicity. The photomicrographs in FIG. 3A show four morphological phenotypes that characterize the differentiation state of primary oligodendroglia (FIGS. 3C and 3D). The photomicrographs in FIG. 3B show loss of morphologic complexity following ATP treatment (50 μM), which was exacerbated by Klk6 (150 nM) (FIGS. 3D-3F) and to a lesser extent by Klk1 (150 nM) (FIG. 3D). Treatment of 3 DIV oligodendrocyte cultures with Klk6 (150 nM) for 24 hours resulted in a significant increase in immature phenotypes (simple, SNK, P=0.007 or incomplete, SNK, P=4.7×10$^{-4}$), while those with a mature phenotype (complete, SNK, P=3.1×10$^{-4}$ or membrane, SNK, P=0.038) were significantly reduced (FIG. 3C). Correspondingly, Klk6 treatment resulted in fewer O4$^+$ processes per cell (FIG. 3E). Treatment with Klk1 alone did not significantly affect oligodendrocyte morphology (FIG. 3C) or process number (FIG. 3E). Treatment with ATP (50 μM) also decreased the number of oligodendroglia with complete morphologies (SNK, P=0.002), increased the number with simple morphology (SNK, P=0.028) and reduced the overall number of O4$^+$ processes per cell (FIGS. 3D and 3E, SNK, P=2.4×10$^{-4}$). Co-application of Klk6 and ATP further increased the loss of mature oligodendrocyte morphologies, increasing the percentage of cells with an immature phenotype, including simple (SNK, P=0.039) and incomplete (SNK, P=0.004), while eliminating cells with mature complete (SNK, P=2.0×10$^{-4}$) and membrane morphologies (SNK, P=0.001) (FIG. 3D). The effects of Klk6 and ATP were additive with regard to loss of O4$^+$ process (FIG. 3E). Klk1 also exacerbated the effects of ATP, reducing the number of oligodendrocytes with a membrane morphology (SNK, P=0.022). ATP promoted a significant loss of O4$^+$ cells (SNK, P=0.006), and this was exacerbated by the addition of Klk6 (SNK, P=0.046), but not Klk1 (FIG. 3F). *P<0.05, P<0.005, *P≤0.001, SNK. (Scale bar=25 μm (FIG. 3A) or 100 μm (FIG. 3B)).

FIG. 4A is a series of photomicrographs, and FIGS. 4B and 4C are a pair of graphs, showing that Klk6, thrombin, and PAR1-AP promote process retraction in Oli-neu oligodendrocytes. The photomicrographs in FIG. 4A show retraction of Oli-neu oligodendrocyte processes 24 hours after treatment with Klk6, thrombin, or PAR1-AP, but not Klk1. FIG. 4B includes histograms showing counts of Cy3-Phalloidin stained Oli-neu processes per cell after 24 hours of treatment with Klk6 (30, 150, and 300 nM), thrombin (270 nM), PAR1-AP (100 μM), or Klk1 (300 nM). Klk6 caused a dose-dependent retraction of Oli-neu processes, relative to control (SNK, P=1.5×10$^{-4}$). Thrombin (SNK, P=1.1×10$^{-4}$) and PAR1-AP (SNK, P=2.7×10$^{-4}$), but not Klk1, also promoted significant process retraction. FIG. 4C includes histograms showing counts of Oli-neu cells per field in each treatment condition, presented as mean number of Phalloidin) processes/DAPI$^+$ nuclei. 30 nM Klk6 and PAR1-AP treatment resulted in a small but significant increase in Oli-neu cell number (SNK, P=0.03 and P=0.003, respectively). Error bars indicate SEM. *P<0.05; **P<0.001, SNK. Scale bar=100 μm.

FIG. 5A is a series of photomicrographs, and FIGS. 5B-5D are a series of graphs, showing that Klk6 impedes oligodendrocyte progenitor process outgrowth in a PAR1-dependent fashion. Purified O4$^+$ oligodendrocyte progenitor cell (OPC) cultures from PAR1$^{+/+}$ mice were differentiated for 24 hours in the presence of Klk6 (150 nM), thrombin (135 nM), or Klk1 (150 nM) (FIG. 5A). Quantification of OPC process number per O4$^+$ cell demonstrated a significant inhibition of OPC process outgrowth in the case of Klk6 and thrombin treatment, but not in response to Klk1 (SNK, P=2.3×10$^{-4}$, P=2.0×10$^{-4}$) (FIG. 5B). Klk6 treated cells also developed significantly fewer processes than thrombin treated cultures (SNK, P=2.3×10$^{-4}$). Klk6 also promoted a significant decrease in cell number (SNK, P=0.032) (FIG. 5C). Klk6-mediated inhibition of process outgrowth was diminished in the presence of the PAR1 inhibitor, SCH79797 (50 nM) (SNK, P=0.006, Klk6 vs. Klk6+SCH), albeit without returning process outgrowth to control levels (SNK, P=2.4×10$^{-4}$) (FIG. 5D). Error bars indicate SEM. *P<0.05; **P<0.001, SNK. Scale bar=100 μm.

FIGS. 6A and 6B are a pair of graphs showing that Klk6 down regulates myelin gene expression in a PAR1-dependent manner in primary oligodendrocytes. Histograms show proteolipid protein (PLP) (FIG. 6A) and myelin basic protein (MBP) (FIG. 6B) RNA expression in PAR1$^{+/+}$ or PAR1$^{-/-}$ primary mouse oligodendrocytes (3 DIV) following a 24 hour treatment with Klk6 (300 nM) or vehicle alone. A significant Klk6-driven down regulation of PLP (Student's t-test, P=5.9×10$^{-4}$) and MBP (Student's t-test, P=0.029) RNA was observed in PAR1$^{+/+}$, but not PAR1$^{-/-}$ oligodendrocytes. Expression data were normalized to GAPDH and shown as percent of control. Error bars indicate SEM. *P<0.05, **P<0.001, Student's t-test.

FIGS. 7A-7F are a series of graphs showing that Klk6-PAR1 signals through Erk1/2 to suppress myelin gene expression. Quantitative PCR was used to determine the level of PLP (FIG. 7A) or MBP (FIG. 7B) RNA in Oli-neu oligodendrocytes following 24 hours of treatment with Klk6 (300 nM), thrombin (270 nM), PAR1-AP (100 μM), or Klk1 (300 nM). A significant down regulation of PLP, but not MBP, RNA was observed after treatment with Klk6 (SNK, P=8.0×10$^{-4}$), thrombin (SNK, P=0.003), or PAR1-AP (SNK, P=7.4×10$^{-4}$). Down regulation of PLP was observed following 24 hours of treatment with as little as 30 nM Klk6 (SNK, P=0.002) (FIG. 7C). Klk6-induced down regulation of PLP RNA was abolished in the presence of the MEK1/2 inhibitor, U0126 (10 μM) (SNK, P=0.009, Klk6 vs. Klk6+U0126) (FIG. 7D). Western blotting showed Erk1/2 phosphorylation in Oli-neu oligodendrocytes treated with Klk6 or Klk1 for 10 min, with or without the PAR1 inhibitor, SCH79797 (50 nM) (FIG. 7E). The histogram in FIG. 7F shows densitometric quantification of bands, revealing a significant increase in Erk1/2 phosphorylation in response to Klk6 (SNK, P=0.012), which was abolished by SCH79797. Band optical density measurements are expressed as percent of maximal response observed. β-actin levels were measured as a loading control. Error bars indicate SEM. *P<0.05, P<0.005, *P≤0.001, SNK.

FIGS. 8A-8C are a series of pictures, and FIGS. 8D-8G are a series of graphs, showing that PAR1 plays a critical role in Klk6-driven myelinopathy in vivo. The photomicrographs in FIGS. 8A and 8B illustrate the extent of white matter pathology observed 72 hours after unilateral microinjection of 2 µL of physiologic saline, Klk6 (0.01 µg/µL), or PAR1-AP (0.1 µg/µL) into the dorsal column of PAR1$^{+/+}$ or PAR1$^{-/-}$ mice (FIG. 8A shows H&E staining; FIG. 8B shows MBP). Dashed lines in H&E stained sections demarcate the site of maximal lesion in each case. As depicted in FIGS. 8C and 8G), microinjection of either Klk6 or PAR1-AP resulted in a significant reduction in the number of CC-1$^{+}$ oligodendrocytes counted per $1\times10^5$ µm$^2$ (the approximate size of the dorsal column in a given section of spinal cord; Klk6, SNK, P=0.001; PAR1-AP, SNK, P=0.002), in PAR$^{+/+}$ but not in PAR$^{-/-}$ mice. Microinjection of Klk6 or PAR1-AP resulted in enhanced rostrocaudal white matter injury (FIG. 8D, Klk6, SNK, P=$6.9\times10^{-4}$; PAR1-AP, SNK, P=0.01), rostrocaudal MBP loss (FIG. 8E; Klk6, SNK, P=$4.1\times10^{-4}$; PAR1-AP, SNK, P=0.001), and maximal lesion area (FIG. 8F; Klk6, SNK, P=$3.3\times10^{-4}$; PAR1-AP, SNK, P=$3.2\times10^{-4}$), relative to saline alone, in PAR$^{+/+}$ but not in PAR1$^{-/-}$ mice. Error bars indicate SEM. *P<0.05, P<0.005, *P≤0.001, SNK. (Scale bar=100 µm, FIGS. 8A and 8B; 75 µm, FIG. 8C.)

FIG. 9A is a graph plotting levels of PAR1 RNA detected in the spinal cord of wild type mice, which were reduced precipitously during the first postnatal week (*P<0.001, Newman Keuls). FIG. 9B is a series of photomicrographs. A combination of immunohistochemistry for PAR1 and immunofluorescence for CC-1 was used to demonstrate co-localization of the receptor to spinal cord white matter oligodendrocytes at all stages of development examined (P7 shown). Arrows indicate a selection of PAR1/CC-1 co-labeled oligodendroglia. Scale bar=20 µm.

FIGS. 10A-10M include a picture of a Western blot and a series of graphs showing that genetic deletion of PAR1 differentially increases PLP and MBP protein levels and is associated with enhanced ERK1/2 signaling in developing and adult spinal cord. The Western blots and associated histograms illustrate that PAR1$^{-/-}$ genetic deletion results in significant changes in the expression of oligodendrocyte-related proteins (FIGS. 10B to 10E), in addition to ERK1/2 (FIGS. 10H and 10K), in homogenates of whole spinal cord. Genetic deletion of PAR1 resulted in higher levels of PLP protein (FIG. 10B) at birth (P0) and P7, higher levels of MBP protein (FIG. 10C) at P45, and higher levels of Olig2 protein (FIG. 10E) at P7 and P21 compared to levels detected in age matched PAR1$^{+/+}$ littermates. Levels of CNPase (FIG. 10D) were reduced in PAR1$^{-/-}$ mice at P21, while no significant differences in NFH (FIG. 10F) or NFL (FIG. 10G) were observed over the same period. PAR1$^{-/-}$ genetic deletion was associated with elevated levels of activated ERK1/2 at P21 (FIG. 10H) and elevated levels of total ERK1/2 from P7 through adulthood (FIG. 10K). Levels of activated AKT were also elevated over those seen at birth in PAR1$^{-/-}$ by P7 (FIG. 10I). No significant differences were observed in either total AKT (FIG. 10L) or in STAT3 (FIGS. 10J and 10M). ROD readings for Westerns were normalized to Actin to control for loading. (*P<0.05,  P≤0.01, *P≤0.001 Newman Keuls; ND, not detected).

FIGS. 11A-11D include a pair of graphs and a series of photomicrographs showing that PAR1 genetic deletion results in increased numbers of spinal cord oligodendroglia. Counts of Olig2-immunopositive cells within the dorsal columns of the spinal cord revealed higher numbers at P0 (1.5-fold, P=0.04, Newman Keuls) and P7 (1.3-fold, *P=0.05, Newman Keuls) in PAR1$^{-/-}$ (FIGS. 11A and 11B), while the number of CC-1 immunopositive cells was significantly elevated in PAR1$^{-/-}$ at P7 (1.6-fold, *P=0.03, Newman Keuls) (FIGS. 11C and 11D). Scale bar=20 µm.

FIGS. 12A-12F include graphs and a series of photomicrographs showing that PAR1 genetic deletion increases the expression of myelin-associated genes and PLP protein in vitro. After a 72 hour period of differentiation, cultured OPCs significantly down regulated the expression of PAR1 (*P=0.0005, Students unpaired t-test) (FIG. 12A). Immediately after isolation (0 h) by shaking from mixed glial cultures, PAR1$^{+/+}$ and PAR1$^{-/-}$ OPCs expressed similar levels of RNA encoding myelin associated proteins (FIG. 12B). After a 72 hour period of differentiation in vitro, PAR1$^{-/-}$ oligodendroglia expressed higher levels of PLP, MBP and Olig2, but lower levels of NogoA compared to wild type oligodendroglia cultured in parallel (FIG. 12C; ***P≤0.001, Student's unpaired t-test). Treatment of oligodendrocytes (24 hours in culture) with a small molecule inhibitor of PAR1 (SCH79797, 70 nM) for 48 hours promoted a significant increase in the expression of PLP and MBP RNA, and a decrease in NogoA and Olig2 RNA (FIG. 12D). The photomicrographs of FIG. 12E show PLP-immunostained PAR1$^{+/+}$ and PAR1$^{-/-}$ OPCs differentiated for 72 hours in vitro. PAR1-loss-of-function (PAR1$^{-/-}$) was associated with a significant increase in the number of PLP-immunoreactive cells (1.3-fold more, *P=$0.03\times10^{-5}$) as well as the amount of PLP-immunoreactivity (ROD) per somal area (1.9-fold, *P=$0.02\times10^{-5}$) (FIG. 12F). Scale bar=20 µm.

FIG. 13C is a series of electron micrographs within the dorsal column white matter of spinal cords from PAR1$^{+/+}$ and PAR1$^{-/-}$ mice. At P0, the g-ratio of axons 1-1.5 µm was reduced in PAR1$^{-/-}$ mice reflecting increased myelin thickness (*P=0.01, Students unpaired t-test) (FIG. 13D). At P45, g-ratios were significantly lower across most axon diameters examined, and increased myelin thickness was observed across all axon diameters (*P≤0.02, Students unpaired t-test). FIG. 13E is a series of electron micrographs from the spinal cord dorsal column of PAR1$^{+/+}$ or PAR1$^{-/-}$, mice showing representative images demonstrating the relative thickness of myelin wrapping 2, 1.3 or 0.5 µm axons. Scale bar A=10 µm; C=2 µm, E=0.2 µm.

FIGS. 14A-14C are a series of graphs showing that PAR1 genetic-loss-of-function results in increased locomotor activity in adulthood. A comprehensive laboratory animal monitoring system was used to demonstrate that PAR1$^{-/-}$ mice have higher activity under fed day (*P=0.04) or fasted night (*P=0.02) conditions (FIG. 14A), and higher ambulation (FIG. 14B; *P=0.02) and rearing (FIG. 14C; *P=0.04) under fasted night conditions (Students unpaired t-test).

FIGS. 18A and 18B are a pair of photomicrographs showing axon remyelination in slices of dorsal column white matter from adult male PAR1$^{+/+}$ (FIG. 18A) or PAR1$^{-/-}$ (FIG. 18B) mice that were microinjected with LL and then perfused with paraformaldehyde 14 days later. Remyelinated axons (arrows) are recognized by their thin appearance relative to axon diameter compared to intact myelin sheaths. FIG. 18C is a graph plotting counts of remyelinated axons in the slices from PAR1$^{+/+}$ and PAR1$^{-/-}$ mice (P=0.04, Students t-test, n=3 per group).

FIG. 19B is a graph plotting the number of neurospheres formed in vitro by the NPCs (**P=0.0007), while

FIG. 21C; **P=0.009, t-test) in NPCs that were isolated from the SVZ of 8 week-old adult C57BL6/J PAR1$^{-/-}$ and PAR1$^{+/+}$ mice and cultured in suspension for 5 days.

FIG. 22A) and Olig2 (a marker for OPCs and mature oligodendrocytes at early stages of differentiation; FIG. 22B).

(FIG. 23A), and higher ambulation (*P=0.02; FIG. 23B) and rearing (*P=0.04; FIG. 23C) under fasted night conditions (Student's unpaired t-test).

DETAILED DESCRIPTION

Figure 1:
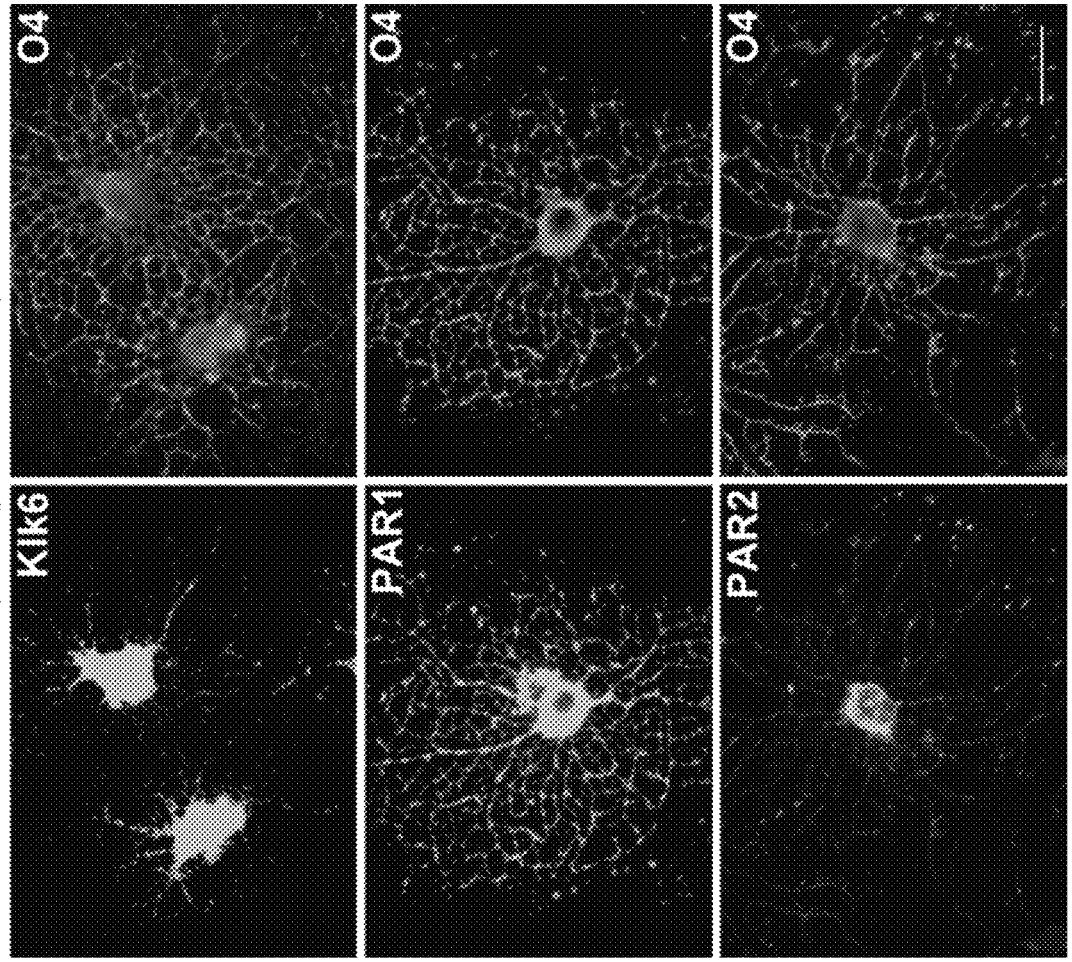
FIG. 1 is a series of photomicrographs showing cellular localization of Klk6, PAR1 and PAR2 in primary oligodendrocytes. Immunocytochemical labeling for Klk6, PAR1 and PAR2 in O4$^+$ mouse oligodendrocyte cultures isolated from PAR1$^{+/+}$ postnatal C57BL6/J mice (3 DIV). Abundant Klk6-immunoreactivity was observed in the cell soma and in some O4$^+$ processes. PAR1 was found in the cell soma and throughout the oligodendrocyte process network. By contrast, PAR2 was localized primarily to process nodules. Scale bar=25 μm.

Demyelinating disease in the central nervous system (CNS) causes deterioration of the myelin sheaths that cover nerve cells in the brain, spinal cord, and optic nerve, preventing the nerves from properly transmitting impulses. Demyelination also can occur in the peripheral nerves.

CNS demyelinating diseases include, for example, multiple sclerosis (MS), which is the most common demyelinating disease of the CNS. A number of demyelinating diseases, such as optic neuritis, neuromyelitis optica, and Leber's hereditary optic neuropathy, affect the optic nerve. Less common CNS demyelinating diseases include Tay-Sachs disease, adrenoleukodystrophy, adrenomyeloneuropathy, and transverse myelitis. Demyelination also can be caused by autoimmune disease, infection, nutritional deficiencies, and low oxygen levels.

The symptoms of CNS demyelinating diseases can affect any part of the CNS, and may include seizures, headaches, delirium, confusion, and/or slurred speech. In some cases, muscle weakness, paralysis, trouble with balance, difficulty walking, tremors, pain, numbness, tingling affect some with the disease, vision and hearing problems, and/or bladder problems can occur. Demyelination disorders tend to progress over time, and some forms of CNS demyelination can lead to early death or disability. For example, while people with MS often have a normal or near-normal life expectancy, hereditary demyelination disorders such Tay-Sachs disease can end in early death.

Demyelination also can occur as a result of injury to the brain or spinal cord. Leakage of blood-derived serine proteases such as thrombin into the CNS is a common component of hemorrhagic, hypoxic, traumatic and infectious injuries (Gingrich and Traynelis, *Trends Neurosci* 23:399-407, 2000). Thrombin can also be generated by CNS endogenous cells, and its elevation has been reported in spinal cord injury (Citron et al., *J Neurotrauma* 17:1191-1203, 2000; Yoon et al., *J Neurochem* 127:283-298, 2013), ischemia (Riek-Burchardt et al., *Neurosci Lett* 329:181-184, 2002; Chen et al., *J Neurosci* 32:7622-7631, 2012) and Alzheimer's disease (Arai et al., *J Neuropathol Exp Neurol* 65:19-25, 2006). In addition to its roles in thrombostasis, thrombin elevation can serve as a powerful neurotoxic agent (Han et al., *Mol Brain* 4:32, 2011; Yoon et al., supra).

Thrombin's cellular actions are conveyed by N-terminal cleavage of an extracellular, seven transmembrane G-protein coupled receptor, protease activated receptor 1 (PAR1), also referred to as the thrombin receptor (Vu et al., *Nature* 353:674-677, 1991). PAR1 has highest affinity for thrombin, but also can be activated by other secreted serine proteases, including plasmin, activated protein C, granzyme A, MMP-1, and select kallikreins (Oikonomopoulou et al., *J Blot Chem* 281:32095-32112, 2006; Oikonomopoulou et al., *Biol Chem* 387:677-685, 2006; Vandell et al., *J Neurochem* 107:855-870, 2008; Adams et al., *Pharmacol Ther* 130:248-282, 2011; Burda et al., *Glia* 61:1456-1470, 2013; Yoon et al., supra). PAR1 activation also plays a role in suppressing myelin gene transcription, in limiting oligodendrocyte progenitor (OPC) process elaboration, and in exacerbating the impact of neurotoxic agents in vitro, and PAR1 can mediate protease-elicited demyelination in vivo in the adult murine spinal cord (Burda et al., supra). A common feature of pre-term birth is intraventricular or intraparenchymal hemorrhage, which can excessively engage the thrombin receptor and lead to a functional blockade of normal myelination.

As described in the Examples herein, a murine genetic model was used to functionally evaluate the role of PAR1 in the process of murine spinal cord myelination at cellular, molecular, and ultrastructural levels. The experimental results demonstrated that PAR1 is a key suppressor of developmental myelination, and that its absence results in elevations in extracellular-signal-regulated kinase (ERK1/2) signaling and hypermyelination, including more myelinated axons and higher levels of PLP at term, as well as the attainment of higher levels of MBP, thicker myelin sheaths, and enhanced motor activity in adults.

This document therefore provides materials and methods for modulating myelination in a subject by delivering to the subject an agent that reduces the activity of PAR1. The subject can be, for example, a mammal, such as a mouse, rat, rabbit, dog, cat, monkey, or human, including preterm infants as well as juveniles or adults who are in need of increased myelination. Since PAR1 acts to suppress myelination, reducing PAR1 activity can increase myelination. In some embodiments, therefore, a subject identified as having or as being at risk for having a CNS demyelinating disorder can be given an agent that reduces the level of PAR1 activity. In some cases, an agent can inhibit the action of the PAR1 protein, while in other cases an agent can inhibit expression of the PAR1 gene.

Suitable agents include, for example, drugs, small molecules, antibodies or antibody fragments, such as Fab' fragments, F(ab')$_2$ fragments, or scFv fragments that bind PAR1, antisense oligonucleotides, interfering RNA (RNAi, including short interfering RNA (siRNA) and short hairpin RNA (shRNA)), or combinations thereof. Methods for producing antibodies and antibody fragments are known in the art. Chimeric antibodies and humanized antibodies made from non-human (e.g., mouse, rat, gerbil, or hamster) antibodies also can be useful. Chimeric and humanized monoclonal antibodies can be produced by recombinant DNA techniques known in the art, for example, using methods described in U.S. Pat. Nos. 4,816,567; 5,482,856; 5,565,332; 6,054,297; and 6,808,901.

Antisense oligonucleotides as provided herein are at least 8 nucleotides in length and hybridize to a PAR1 transcript. For example, a nucleic acid can be about 8, 9, 10 to 20 (e.g., 11, 12, 13, 14, 15, 16, 17, 18, 19, or 20 nucleotides in length), 15 to 20, 18 to 25, or 20 to 50 nucleotides in length. In some embodiments, antisense molecules greater than 50 nucleotides in length can be used, including the full-length sequence of a PAR1 mRNA. As used herein, the term "oligonucleotide" refers to an oligomer or polymer of ribonucleic acid (RNA) or deoxyribonucleic acid (DNA) or analogs thereof. Nucleic acid analogs can be modified at the base moiety, sugar moiety, or phosphate backbone to improve, for example, stability, hybridization, or solubility of a nucleic acid. Modifications at the base moiety include substitution of deoxyuridine for deoxythymidine, and 5-methyl-2'-deoxycytidine and 5-bromo-2'-deoxycytidine for deoxycytidine. Other examples of nucleobases that can be substituted for a natural base include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleobases include those disclosed, for example, in U.S. Pat. No. 3,687,808.

Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller, *Antisense Nucleic Acid Drug Dev.* 7:187-195, 1997; and Hyrup et al., *Bioorgan. Med. Chem.* 4:5-23, 1996. In addition, the deoxyphosphate backbone can be replaced with, for example, a phosphorothioate or phosphorodithioate backbone, a phosphoroamidite, or an alkyl phosphotriester backbone. See, for example, U.S. Pat. Nos. 4,469,863; 5,235,033; 5,750,666; and 5,596,086 for methods of preparing oligonucleotides with modified backbones.

Antisense oligonucleotides also can be modified by chemical linkage to one or more moieties or conjugates that enhance the activity, cellular distribution or cellular uptake of the oligonucleotide. Such moieties include but are not limited to lipid moieties (e.g., a cholesterol moiety); cholic acid; a thioether moiety (e.g., hexyl-S-tritylthiol); a thiocholesterol moiety; an aliphatic chain (e.g., dodecandiol or undecyl residues); a phospholipid moiety (e.g., di-hexadecyl-rac-glycerol or triethyl-ammonium 1,2-di-O-hexadecyl-rac-glycero-3-H-phosphonate); a polyamine or a polyethylene glycol chain; adamantane acetic acid; a palmityl moiety; or an octadecylamine or hexylamino-carbonyl-oxycholesterol moiety. The preparation of such oligonucleotide conjugates is disclosed in, for example, U.S. Pat. Nos. 5,218,105 and 5,214,136.

Methods for synthesizing antisense oligonucleotides are known, including solid phase synthesis techniques. Equipment for such synthesis is commercially available from several vendors including, for example, Applied Biosystems (Foster City, CA). Alternatively, expression vectors that contain a regulatory element that directs production of an antisense transcript can be used to produce antisense molecules.

Antisense oligonucleotides can bind to a nucleic acid encoding PAR1, including DNA encoding PAR1 RNA (including pre-mRNA and mRNA) transcribed from such DNA, and also cDNA derived from such RNA, under physiological conditions (i.e., physiological pH and ionic strength).

It is understood in the art that the sequence of an antisense oligonucleotide need not be 100% complementary to that of its target nucleic acid to be hybridizable under physiological conditions. Antisense oligonucleotides hybridize under physiological conditions when binding of the oligonucleotide to the PAR1 nucleic acid interferes with the normal function of the PAR1 nucleic acid, and non-specific binding to non-target sequences is minimal.

Target sites for PAR1 antisense oligonucleotides can include the regions encompassing the translation initiation or termination codon of the open reading frame (ORF) of the gene. In addition, the ORF can be targeted effectively in antisense technology, as have the 5' and 3' untranslated regions. In some embodiments, antisense oligonucleotides can be directed at intron regions and intron-exon junction regions. Further criteria can be applied to the design of antisense oligonucleotides. Such criteria are well known in the art, and are widely used, for example, in the design of oligonucleotide primers. These criteria include the lack of predicted secondary structure of a potential antisense oligonucleotide, an appropriate G and C nucleotide content (e.g., approximately 50%), and the absence of sequence motifs such as single nucleotide repeats (e.g., GGGG runs). The effectiveness of antisense oligonucleotides at modulating expression of a PAR1 nucleic acid can be evaluated by measuring levels of the PAR1 mRNA or polypeptide (e.g., by Northern blotting, RT-PCR, Western blotting, ELISA, or immunohistochemical staining).

Single and double-stranded interfering RNA (RNAi, such as siRNA and shRNA) homologous to PAR1 DNA also can be used to reduce expression of PAR1 and consequently, activity of PAR1. See, e.g., U.S. Pat. No. 6,933,146; Fire et al., *Nature* 391:806-811, 1998; Romano and Masino, *Mol. Microbial.* 6:3343-3353, 1992; Cogoni et al., *EMBO J.* 15:3153-3163, 1996; Cogoni and Masino, *Nature* 399:166-169, 1999; Misquitta and Paterson, *Proc. Natl. Acad. Sci. USA* 96:1451-1456, 1999; and Kennerdell and Carthew, *Cell* 95:1017-1026, 1998.

The sense and anti-sense RNA strands of RNAi can be individually constructed using chemical synthesis and enzymatic ligation reactions using procedures known in the art. For example, each strand can be chemically synthesized using naturally occurring nucleotides or nucleic acid analogs. The sense or anti-sense strand also can be produced biologically using an expression vector into which a target PAR1 sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to the tumor vasculature or to tumor cells.

In some embodiments, a PAR1 agent can be incorporated into a pharmaceutical composition. For example, an agent can be suspended in a pharmaceutically-acceptable carrier (e.g., physiological saline), and can be administered via any suitable route. For example, an agent can be delivered orally or by intravenous infusion, or injected subcutaneously, intramuscularly, intrathecally, intraperitoneally, intrarectally, intravaginally, intranasally, intragastrically, intratracheally, or intrapulmonarily. The agent can, for example, be delivered directly to the affected organ or tissue and/or vasculature of the organ, or a site of an immune response such as a lymph node in the region of an affected tissue or organ or spleen. For treating tissues in the central nervous system, an agent can be administered by injection or infusion into the cerebrospinal fluid, optionally with one or more additional agents that are capable of promoting penetration of the first agent across the blood-brain barrier.

Dosage required depends on the choice of the route of administration, the nature of the formulation, the nature of the patient's illness, the subject's size, weight, surface area, age, and gender, other drugs being administered, and the judgment of the attending physician. Suitable dosages typically are in the range of 0.0001-100.0 mg/kg, although wide variations in the needed dosage are to be expected in view of the variety of compounds available and the differing efficiencies of various routes of administration. Variations in dosage levels can be adjusted using standard empirical routines for optimization as is well understood in the art. Encapsulation of an agent in a suitable delivery vehicle (e.g., polymeric microparticles or an implantable device) may increase the efficiency of delivery, particularly for oral delivery.

In some embodiments, a nucleic acid (e.g., an expression vector containing a regulatory sequence operably linked to a nucleic acid encoding an antisense oligonucleotide, or an expression vector from which sense and anti-sense RNAs can be transcribed under the direction of separate promoters, or a single RNA molecule containing both sense and anti-sense sequences can be transcribed under the direction of a single promoter) can be delivered to appropriate cells in a subject. Suitable expression vectors include, for example, plasmids and viral vectors such as herpes viruses, retroviruses, vaccinia viruses, attenuated vaccinia viruses, canary pox viruses, adenoviruses and adeno-associated viruses, among others.

Expression of a nucleic acid can be directed to any cell in the body of the subject. However, it can be particularly useful to direct expression to cells in, or close to, the CNS. Targeted expression can be achieved by, for example, the use of polymeric, biodegradable microparticle or microcapsule delivery devices known in the art and/or tissue or cell-specific antibodies. Alternatively, tissue specific targeting can be achieved by the use of tissue-specific transcriptional regulatory sequences (i.e., tissue specific promoters) which are known in the art.

Nucleic acids also can be delivered to cells using liposomes, which can be prepared by standard methods. Vectors can be incorporated alone into these delivery vehicles, or can be co-incorporated with tissue-specific antibodies. Alternatively, a molecular conjugate composed of a plasmid or other vector attached to poly-L-lysine by electrostatic or covalent forces can be prepared. Poly-L-lysine binds to a ligand that can bind to a receptor on target cells (Cristiano et al., *J. Mol. Med.* 73:479, 1995). Delivery of "naked DNA" (i.e., without a delivery vehicle) to an intramuscular, intradermal, or subcutaneous site is another means to achieve in vivo expression.

In some embodiments, an agent that reduces PAR1 activity can be incorporated into a pharmaceutical composition, such as by combination with a pharmaceutically acceptable carrier. Pharmaceutically acceptable carriers are biologically compatible vehicles that are suitable for administration to a mammal (e.g., a human), and include, for example, water, physiological saline, and liposomes. Pharmaceutically acceptable carriers can be selected with the planned manner of administration in mind so as to provide for the desired bulk, consistency, and other pertinent transport and chemical properties, when combined with one or more of components of a given pharmaceutical composition.

As discussed above, the dosage for any one patient depends upon many factors, including the patient's size, body surface area, age, the particular compound to be administered, sex, time and route of administration, general health, and other drugs being administered concurrently. Dosages will vary, but a preferred dosage for administration of nucleic acid is from approximately $10^6$ to approximately $10^{12}$ copies of the nucleic acid. This dose can be repeatedly administered, as needed. Routes of administration can be any of those described above.

In addition, a method can be an ex vivo procedure that involves providing a recombinant cell that is, or is a progeny of a cell, obtained from a subject and has been transfected or transformed ex vivo with one or more nucleic acids encoding one or more agents that reduce PAR1 activity (e.g., an siRNA targeted to PAR1), so that the cell expresses the agent(s); and administering the cell to the subject. The cells can be cells obtained from the subject to whom they are to be administered, or from another subject. The donor and recipient of the cells can have identical major histocompatibility complex (MEW; HLA in humans) haplotypes. In some embodiments, the donor and recipient are homozygotic twins or are the same individual (i.e., are autologous). The recombinant cells can also be administered to recipients that have no, or only one, two, three, or four MHC molecules in common with the recombinant cells, e.g., in situations where the recipient is severely immuno-compromised, where only mismatched cells are available, and/or where only short term survival of the recombinant cells is required or desirable.

The efficacy of an agent can be evaluated both in vitro and in vivo. Briefly, an agent can be tested for its ability, for example, to (a) reduce PAR1 activity, (b) increase myelination, or (c) inhibit or slow the progression of demyelination. For in vivo studies, the agent can, for example, be injected into an animal (e.g., a mouse model of CNS demyelination), and its effects then can be assessed. Suitable methods for evaluating the level or progression of myelination/demyelination include, without limitation, imaging, motor evoked potential, visual evoked potentials, sensorimotor, and cognitive functional outcomes. Based on the results, an appropriate dosage range and administration route can be determined.

In some embodiments, the methods provided herein can include identifying a subject as being in need of increased myelination. A subject can be identified on the basis of, for example, having a disorder characterized by demyelination (e.g., demyelination in the CNS). In some cases, the subject can be identified as having a neuroinflammatory disease or a stroke, or as having an injury to the CNS.

In some embodiments of the methods provided herein, an agent that reduces PAR1 activity, or a composition containing such an agent, can be administered to a subject in an amount effective to reduce or prevent demyelination, or to enhance remyelination. For example, an effective amount of an agent or a composition containing an agent can reduce the level or rate of demyelination in a subject by at least 10 percent (e.g., at least 20, 30, 40, 50, 60, 70, 80, 90, 10 to 25, 25 to 50, 50 to 75, or 75 to 100 percent) as compared to the level or rate of demyelination in the subject prior to treatment, or as compared to the level or rate of demyelination in an untreated subject. In some embodiments, an effective amount of an agent or a composition containing an agent can increase the level or rate of remyelination in a subject by at least 10 percent (e.g., at least 20, 30, 40, 50, 60, 70, 80, 90, 10 to 25, 25 to 50, 50 to 75, or 75 to 100 percent) as compared to the level or rate of remyelination in the subject prior to treatment, or as compared to the level or rate of remyelination in an untreated subject.

In some cases, a method as provided herein can include delivering to a subject a population of stem cells that have been modified to have reduced PAR expression as compared to corresponding wild type neural stem cells. For example, the stem cells can be modified in vitro to contain a mutation in the PAR1 gene, such that PAR1 expression is reduced or even knocked out. Suitable types of stem cells include, without limitation, embryonic stem cells, induced pluripotent stem cells, bone marrow derived stem cells, mesenchymal stem cells, and neural stem cells. After delivery to the subject (e.g., a preterm infant, or a juvenile or adult having a CNS injury or demyelinating disorder), the stem cells can differentiate into neuronal cells and, due to their reduced level of PAR1 expression, can facilitate or enhance myelination.

The invention will be further described in the following examples, which do not limit the scope of the invention described in the claims.

EXAMPLES

Example 1—Critical Role for PAR1 in Kallikrein 6-Mediated Oligodendrogliopathy Materials and Methods Animal care and use: Eight- to ten-week-old C57BL6/J mice were obtained from Jackson Laboratories. Mice deficient in PAR1 (PAR1', B6.129S4-F2r$^{tm1Ajc}$/J) or PAR2 (PAR2$^{-/-}$, B6.Cg-F2rl1(tm1Mslb)/J) were obtained from Jackson and backcrossed to C57BL6/J for at least 20 generations, such that PAR1$^{+/+}$ littermates served as controls.

Oligodendrocyte Cultures: Purified cortical oligodendrocyte progenitor cells (OPCs) and differentiated oligodendrocytes were isolated from mixed glial cultures derived from postnatal day 1 mice (McCarthy and de Vellis, *J Cell Blot* 85:890-902, 1980). Glial cultures were grown in media containing DMEM, 2 mM Glutamax, 1 mM sodium pyruvate, 20 mM HEPES, and 10% heat-inactivated fetal calf serum (Atlanta Biologicals, Lawrenceville, GA). OPCs were isolated from 10 days-in-vitro (DIV) mixed glial cultures by overnight shaking and purified by differential adhesion. OPCs were seeded in defined Neurobasal A media containing 1% N2, 50 U/mL penicillin/streptomycin, 2 mM Glutamax, 1 mM sodium pyruvate, 0.45% glucose, and 50 µM β-mercaptoethanol (Sigma Aldrich, USA). OPCs were seeded at $3\times10^4$/cm$^2$ onto tissue culture plastic or 12 mm glass cover slips coated with poly-L-lysine (PLL, 10 µg/mL). After 24 h, cultures were 92-98% immunoreactive (IR) for sulfatide (O4) and by 72 hours at least 80% were also MBP-IR.

Oli-neu oligodendrocytes are derived from mouse primary oligodendrocyte cultures retrovirally transduced to constitutively express the t-neu oncogene (Jung et al., *Eur J Neurosci* 7:1245-1265, 1995). All morphology, signaling, and myelin gene expression studies using Oli-neu oligodendrocytes were performed in media containing DMEM, 1% N2, 2 mM Glutamax, 1 mM sodium pyruvate, 20 mM HEPES buffer, and 50 µM β-mercaptoethanol (Sigma Aldrich. To evaluate PAR and Klk6 gene expression in Oli-neu (Table 2), cells were differentiated by treatment with 1 mM N$^6$, 2'-O-dibutyryladenosine 3', 5'-cyclic monophosphate disodium salt (dbcAMP) for 72 hours prior to harvesting for RNA isolation. All cells were maintained at 37° C. in 95% air and 5% $CO_2$. Cell culture reagents were obtained from Life Technologies (Carlsbad, CA) unless otherwise indicated. All cell culture experiments were performed in triplicate and repeated at least twice.

Recombinant kallikreins and PAR agonists: Recombinant murine Klk6 and Klk1 were expressed using a baculovirus system and purified as described previously (Blaber et al., *Biochemistry* 41:1165-1173, 2002; Scarisbrick et al., *PLoS One* 6:e18376, 2011; and Scarisbrick et al., *Biol Chem* 393:355-367, 2012a). Concentrations of Klk6 used in these studies (30-300 nM (1-10 µg/mL; 15,000-159,000 U/mL)) were based on previous work demonstrating those sufficient to elicit Ca$^{2+}$ signaling and Erk1/2 activation in neural cells (Vandell et al., supra). Klk1 was used at comparable concentrations (300 nM (10 µg/mL; 173,000 U/mL)). An equivalent concentration of Human α-thrombin (270 nM (10 μg/mL; 161,000 U/mL, Enzyme Research Laboratories, South Bend, IN)) was also examined. The specific activity of 1 ng of Klk6, Klk1, or thrombin was measured by analysis of the rate of hydrolysis against 100 μM t-Butyloxycarbonyl-Valine-Proline Arginine-7-Amino-4-methylcoumarin (Boc-VP-AMC) fluorogenic peptide substrate (R&D Systems, Minneapolis, MN). PAR1-activating peptide (PAR1-AP) (TFLLR-amide (SEQ ID NO:21), Peptides International) that mimics the PAR1 tethered ligand was used at 100 μM (100 μg/mL) (Vandell et al., supra).

Expression of oligodendrocyte PARs and Klk6-immunocytochemistry for PARs and Klk6: Oligodendrocyte cultures seeded on glass cover slips were immunostained with the following primary antibodies: rabbit anti-Klk6 (Scarisbrick et al., Brain Pathol 22:709-722, 2012b), goat anti-PAR1 (C-18) or -PAR2 (C-17) (Santa Cruz, Santa Cruz, CA), and mouse anti-sulfatide (O4) (Dr. Ben Barres, Stanford University). Immunostaining involved fixation of cultures with 2% paraformaldehyde (PFA) prior to incubation with primary antibody, with the exception of O4 immunostaining, which was accomplished using live cells at 4° C. followed by fixation with 2% PFA. Cells were then incubated with affinity-purified, species—appropriate fluorochrome-conjugated secondary antibodies (Jackson Immunoresearch Laboratories, Westgrove, PA) and mounted using VECTASHIELD with 4',6-diamidino-2-phenylindole (DAPI) (Vector Laboratories, Burlingame, CA).

Expression of oligodendrocyte PARs and Klk6-real-time quantitative PCR: Total RNA was isolated from cultured cells using RNA STAT-60 (Tel-Test, Friendswood, TX). Klk6, PAR1, or PAR2 RNA expression was determined in 0.5 μg of RNA with the iScript one-step RT-PCR kit with SYBR® Green and the iCycler iQ5 system (BioRad, Hercules, CA). Transcript copy number was determined using a standard curve prepared by parallel amplification of cDNA clones diluted to known copy number (Christophi et al., J Neurochem 91:1439-1449, 2004). Primers used for amplification are listed in Table 1. Amplification of the housekeeping gene glyceraldehyde phosphate 3-dehydrogenase (GAPDH) was used to control for loading. The mean and standard error (SEM) of transcript copy number was determined and data expressed as RNA copy number on a logarithmic scale.

PAR agonist-induced changes in oligodendrocyte morphology: To determine the effects of recombinant Klk6, Klk1, thrombin, or PAR1-AP on oligodendroglia, 3 DIV $PAR1^{+/+}$, $PAR1^{-/-}$, and $PAR2^{-/-}$ oligodendrocytes, $PAR1^{+/+}$ OPCs immediately post purification, or Oli-neu cells were grown on cover slips in the presence of agonists for 24 h. For ATP toxicity assays, oligodendrocytes were incubated with ATP (50 μM, Sigma Aldrich) in the presence of Klk6 or Klk1. Following each treatment, oligodendrocyte and OPC cultures were immunolabeled for O4 to visualize the cell body and processes. Oli-neu processes were visualized by staining the actin cytoskeleton with Cy3-conjugated Phalloidin.

To assess the effects of Klk6 and other PAR1 agonists on oligodendrocyte morphology and process stability, 20× digital micrographs were overlaid with a 780 μm² grid and ImageJ software 1.45r (National Institutes of Health) used to record cell number and the number of processes crossing horizontal grid lines (Scarisbrick et al., Brain 125:1283-1296, 2002). Data are expressed as the mean number of $O4^+$ or Phalloidin⁺ processes per $DAPI^+$ cell (±SEM).

The extent of oligodendrocyte morphological differentiation was determined by scoring $O4^+/DAPI^+$ oligodendrocyte morphology as simple (only primary processes, no secondary branching), incomplete (one or more primary process without secondary branching), complete (all primary processes with secondary branching), or membrane (complete secondary branching with membrane sheets) (Huang et al., Nat Neurosci 14:45-53, 2011). The mean number of cells in each morphology class was determined across treatments and expressed as percent of total $O4^+/DAPI^+$ cells.

Changes in OPC or oligodendrocyte morphology were quantified from five microscopic fields per cover slip with the mean and SEM calculated across three cover slips per experiment. Each experiment was repeated at least twice using independent cultures. Analysis of oligodendrocyte morphology was performed without knowledge of treatment groups.

Regulation of oligodendrocyte myelin gene expression by PAR1 agonists: Primary murine oligodendrocytes (3 DIV) or Oli-neu oligodendrocytes were seeded at $3.5 \times 10^5$ cells/well in six-well tissue culture plates. Cells were then treated with Klk6 (30-300 nM), Klk1 (300 nM), thrombin (270 nM), or PAR1-AP (100 μM) for 24 hours prior to RNA isolation. Expression of myelin-associated genes, PLP, and MBP was examined by real-time quantitative RT-PCR. Expression levels of target genes were normalized to GAPDH and expressed as percent control.

Klk6-PAR signaling assays: To examine the ability of Klk6 to mediate PAR-dependent signaling in oligodendrocytes, Oli-neu oligodendroglia ($3.5 \times 10^5$ cells/well in six-well plates) were treated with Klk6 (150 nM) for 10 min, followed by protein harvest. Cell lysates were analyzed for phosphorylated or nonphosphorylated Erk1/2 by Western blot. In experiments to determine the role of PARs in Klk6 signaling, Oli-neu were preincubated with the PAR1 antagonist, SCH79797 dihydrochloride (50 nM, Tocris Biosciences, Minneapolis, MN) for 30 minutes prior to Klk6 application.

Western blot: Oli-neu lysates were obtained using a buffer containing 1% NP40, 0.5% deoxycholate, 10% glycerol, and 20 mM Tris base and separated on SDS-polyacrylamide gels prior to transfer. Membranes were blocked with 5% milk in TBS-T and incubated overnight with primary antibodies including rabbit anti-phospho-Erk1/2 (1:1,000, Cell Signaling Technology, Danvers, MA), followed with a species-appropriate horseradish peroxidase-conjugated secondary antibody (1:20,000 GE Healthcare Unlimited, UK). Signal was detected using Chemiluminescence Supersignal Pico (Pierce, Rockford, IL). Western blots were repeated three times from independent cultures, scanned, and quantified by densitometry (BioRad Quantity One 1-D Analysis Software, BioRad, Hercules, CA). Erk1/2 signal was normalized to its nonphosphorylated form. Equal loading was verified by reprobing blots for 3-Actin (Novus Biologicals, Littleton, CO).

In vivo effects of excess Klk6 or PAR1-AP in spinal cord white matter: All mice were administered Buprenorphine preoperatively (Buprenex, 0.03 mg/kg, intraperitoneal (i.p.), Reckitt Benckise, Slough, UK) and every 12 hours for the first 48 hours following surgery. Surgical anesthesia was induced in age-matched male C57BL6/J or PAR12/2 mice using Ketamine (Ketaset, 80 mg/kg, Fort Dodge Animal Health, Fort Dodge, IA) and Xylazine i.p. (Anased, 10 mg/kg, Lloyd Laboratories, Shenendoah, IA). A thoracic (T11-T12) laminectomy was performed and a 30-40 μm glass capillary needle inserted into a 10 μL gas-tight Hamilton Syringe (Hamilton Company, Reno, NV) used to deliver 2 μL of Klk6 (0.01 μg/μL (300 nM)), PAR1-AP (0.01 μg/μL (100 μM)), or vehicle (physiologic saline) alone (n=3 for each treatment group) using a stereotaxic injection system (Stoelting, Wood Dale, IL). Under micromanipulator control (MyNeurolab, Richmond, IL), the needle was inserted 350 µm into the dorsal column, infusion carried out over 5 minutes and the needle left in place for 3 minutes to avoid backflow. All mice received 0.5 mL of sterile saline and Baytril (2.5 mg/kg, Bayer Healthcare, Shawnee Mission, KS) i.p. postoperatively.

Seventy-two hours after microinjection of PAR1 agonists, mice were deeply anesthetized with Nembutal (50 mg/kg, i.p., Lundbeck, Deerfield, IL) and perfused transcardially with 4% PFA. Two millimeter transverse spinal cord segments encompassing the microinjection epicenter as well as 2 mm rostral and caudal were embedded in paraffin. Six micrometer sections were cut and slide mounted serially. Every sixth slide was stained with hematoxylin and eosin (H&E). Adjacent sections were immunostained for oligodendroglia using an antibody specific for CC-1/APC (ab16794, AbCam, Cambridge, MA), myelin using an antibody recognizing MBP (MAB386, Millipore, Bedford, MA), and standard avidin-biotin immunoperoxidase techniques (Scarisbrick et al., *J Comp Neurol* 431:347-361, 2001; and Scarisbrick et al. 2012b, supra). Stained sections were cover slipped with Permount (Fisher Scientific, Pittsburgh, PA) containing 2 mg/mL bisbenzamide to visualize nuclei (Sigma Aldrich).

Measurements of white matter lesion area were based on signs of pathology (vacuolation, tissue destruction, hemorrhage) in 20× digital images of H&E stained sections. The largest lesion area in each animal was used to determine mean maximal lesion area and expressed in $\mu m^2$. The integrity of MBP immunoreactivity was assessed in sections for 2,000 µm rostrocaudal to the microinjection site. The number of dorsal column CC-1$^+$/DAPI$^+$ cells was quantified in sections across 300 mm of spinal cord extending rostrocaudal to the epicenter. The mean area of dorsal column white matter in the intact spinal cord was approximately $1.5 \times 10^5$ mm$^2$. To put the number of CC-1$^+$ oligodendrocytes into context, the mean number CC-1V cells per mm$^2$ was evaluated as the mean number per $1.5 \times 10^5$ mm$^2$. Sections stained for CC-1 were also stained for GFAP (Sigma Aldrich), allowing for the exclusion of CC-1$^+$ astrocytes; however, no examples of double labeled cells were observed.

Statistical analysis: Student's t-test was used to determine the significance of differences between two treatment groups and the Mann-Whitney U test was used when data were not normally distributed. For comparisons between multiple groups, one-way analysis of variance (ANOVA) and the Student-Newman-Keuls (SNK) post-hoc test, or the Kruskal-Wallis ANOVA on Ranks with Dunn's method for pairwise comparisons were applied in the case of normally or not normally distributed data, respectively. Statistical significance was set at P<0.05.

Results

Expression of Klk6, PAR1, and PAR2 in oligodendrocytes and OPCs: Kallikrein 6 is known to be highly expressed by oligodendroglia of the rodent spinal cord, in vivo and in vitro (Scarisbrick et al., *J Neurosci* 17:8156-8168, 1997; and Scarisbrick et al., *Glia* 30:219-230, 2000). Here, Klk6 was shown to be densely expressed throughout the cytoplasm and processes of purified, O4$^+$ murine primary oligodendrocytes (3 DIV) (FIG. 1). O4$^+$ oligodendrocytes were also immunoreactive for PAR1 and PAR2. PAR1-immunorectivity was observed throughout the cell body and process network. PAR2-immunoreactivity was also dense in the cell body, but showed more limited staining in processes being most dense at nodule branch points (FIG. 1). A parallel pattern of Klk6, PAR1, and PAR2 immunoreactivity was observed in the Oli-neu oligodendrocytes (data not shown).

Quantitative real-time PCR was used to determine RNA expression levels of Klk6, PAR1, and PAR2 in primary cultures of OPCs and differentiated oligodendrocytes (3 DIV) (Table 2). Equivalent levels of Klk6 RNA were observed at both stages of oligodendrocyte differentiation. High levels of PAR1 RNA were detected in both OPC and oligodendrocyte cultures, though expression significantly declined with differentiation (Student's t-test, P=0.030). PAR2 RNA levels were nearly 4-log values lower than PAR1 and expressed by OPCs and oligodendrocytes at equivalent levels. Klk6, PAR1, and PAR2 RNA levels were also determined for the Oli-neu cell line, under resting and dbcAMP-differentiated conditions (Table 2). Levels of Klk6 RNA were similar for resting and differentiated Oli-neu oligodendrocytes. PAR1 RNA expression was approximately 3-log values greater than PAR2 in Oli-neu oligodendrocytes, and each was expressed at equivalent levels in resting and differentiated culture conditions.

Figure 2A:
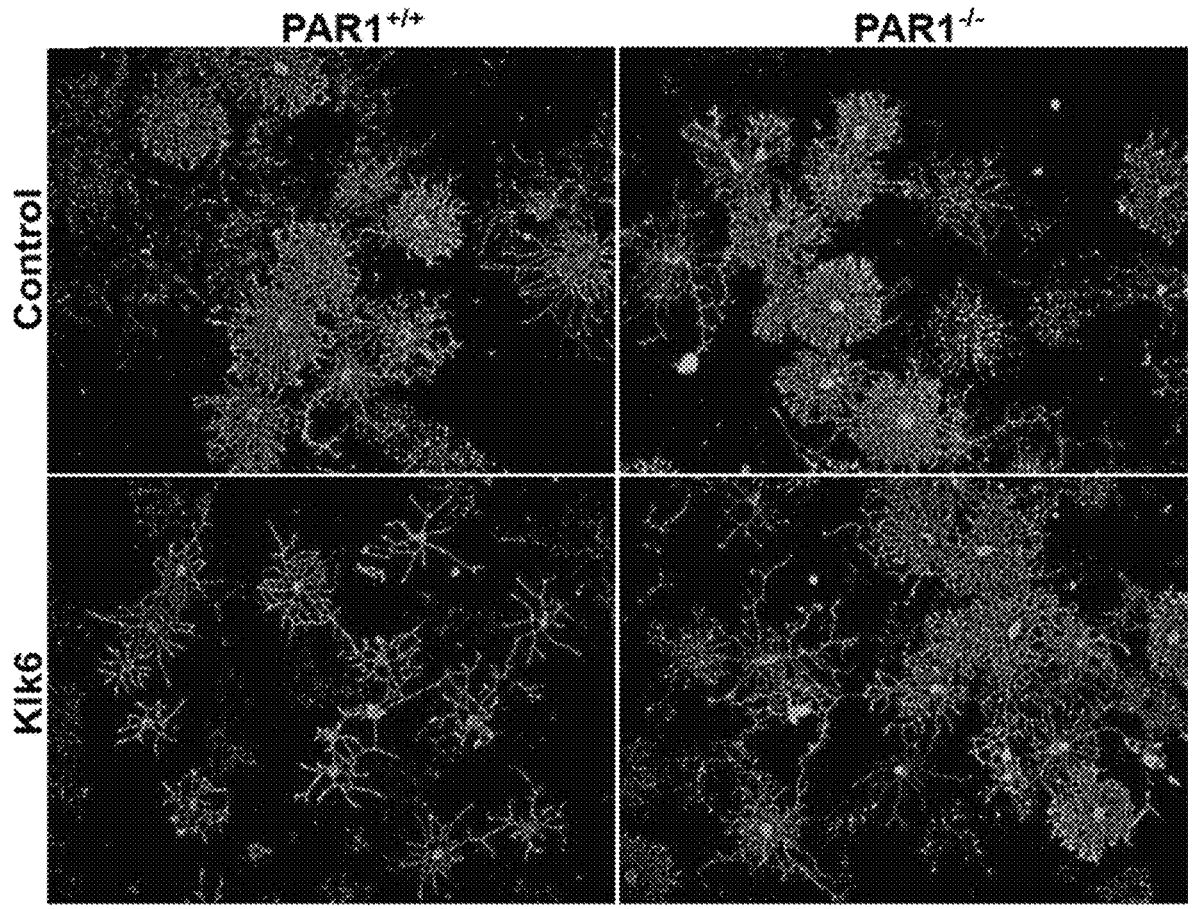
FIG. 2A is a series of photomicrographs and FIGS. 2B and 2C are graphs showing that PAR1 is necessary for Klk6-induced oligodendrogliopathy in primary oligodendrocytes. O4$^+$ oligodendrocyte cultures from PAR1$^{+/+}$, PAR1$^{-/-}$, or PAR2$^{-/-}$ mice were treated with active recombinant Klk6 for 24 h. Klk6 (30 nM) promoted significant process retraction in PAR1$^{+/+}$ (SNK, P=9.0×10$^{-4}$) or PAR2$^{-/-}$ (SNK, P=0.002) oligodendrocytes, but not in the absence of PAR1 (FIGS. 2A and 2B). Klk6 treatment had no effect on oligodendrocyte number in cultures isolated from either PAR1$^{+/+}$, PAR1$^{-/-}$, or PAR2$^{-/-}$ mice. Error bars indicate SEM. *P=<0.005, **P=<0.001, SNK. Scale bar=100 μm.
Figure 2B:
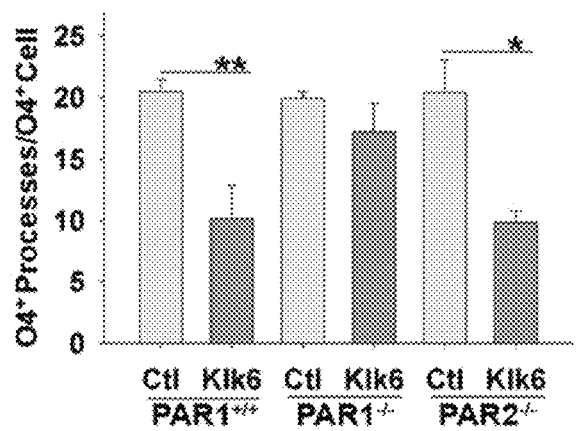
Figure 2C:
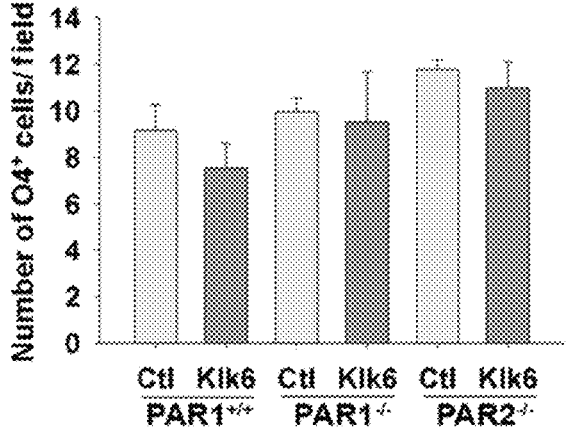

Klk6-mediated injury to mature oligodendroglial processes is PAR1-dependent: In human cerebrospinal fluid (CSF), the concentration of KLK6 is approximately 40 nM, which is likely representative of that in the CNS (Zarghooni et al., *Clin Biochem* 35:225-231, 2002). Klk6 levels are substantially elevated at sites of CNS injury (Scarisbrick et al. 2002, supra; Scarisbrick et al., *Eur J Neurosci* 24:1457-1469, 2006; and Scarisbrick et al. 2012a, supra). Treatment of rat primary oligodendrocytes with 30 or 300 nM recombinant Klk6 for 24 hours resulted in significant process retraction without oligodendrocyte degeneration (Scarisbrick et al. 2002, supra). As described herein, this phenotype is confirmed in PAR1$^{+/+}$ murine oligodendrocyte cultures (3 DIV) (FIGS. 2A-2C). Treatment of oligodendrocytes with either 30 (FIGS. 2A and 2B; SNK, P=$9.0 \times 10^{-4}$) or 300 nM Klk6 (SNK, P=$4.7 \times 10^{-4}$) each produced significant and statistically equivalent oligodendrocyte process retraction compared with controls. To determine the involvement of PARs in Klk6-oligodendrogliopathy, results were compared between primary PAR1$^{+/+}$ oligodendrocyte cultures and those derived from PAR1$^{-/-}$ or PAR2$^{-/-}$ mice. PAR1$^{-/-}$ oligodendrocytes did not exhibit statistically significant process retraction in response to 30 (FIGS. 2A and 2B) or 300 nM Klk6. By contrast, treatment of PAR2$^{-/-}$ oligodendrocytes with Klk6 resulted in process retraction comparable to that seen in PAR1$^{+/+}$ cultures (FIG. 2B; 30 nM Klk6, SNK, P=0.002; 300 nM Klk6, SNK, P=$1.2 \times 10^{-4}$ vs. Control). No significant differences in the number O4$^+$ PAR1$^{+/+}$, PAR1$^{-/-}$, or PAR2$^{-/-}$ cells were observed in response to Klk6 treatment (FIG. 2C).

To further evaluate the effects of excess Klk6 on oligodendroglial processes, primary oligodendrocyte cultures (3 DIV) were treated with recombinant Klk6 (150 nM) for 24 hours and quantified with respect to morphological maturity, albeit simple, incomplete, complete, or membrane morphologies (Huang et al., supra) (FIG. 3A). Klk6 promoted a two-fold increase in the number of simple (SNK, P=0.007) and a greater than four-fold increase in the number of incomplete (SNK, P=$4.7 \times 10^{-4}$) oligodendrocyte morphologies. Additionally, Klk6 promoted a nearly eleven-fold decrease in oligodendrocytes with complete morphology (FIG. 3C; SNK, P=$3.1 \times 10^{-4}$) and the elimination of oligodendroglia with the most mature membrane morphology (SNK, P=0.038). Klk6 treatment also resulted in two-fold fewer processes per cell (FIG. 3E; SNK, P=2.8×10$^{-4}$), but there was no significant effect on oligodendrocyte number (FIG. 3F). By contrast, recombinant Klk1 (300 nM) did not significantly impact oligodendrocyte morphology (FIG. 3C), process (FIG. 3E), or cell number under the conditions of this study (FIG. 3F).

Elevated Klk6 exacerbates ATP toxicity in oligodendrocytes: Aberrant ATP signaling causes oligodendrocyte excitotoxicity and high levels of ATP have been associated with pathophysiology in both SCI and MS (Matute et al., *J Neurosci* 27:9525-9533, 2007; Wang et al., *Nat Med* 10:821-827, 2004). Experiments were conducted to investigate whether elevated levels of Klk6 augment ATP-induced excitotoxicity in oligodendroglia, using loss of morphological differentiation and cell number as measures of pathogenicity. Twenty-four hour treatment of primary oligodendrocyte cultures (3 DIV) with ATP (50 μM) resulted in a significant increase in the percentage of cells with simple morphology (FIG. 3B; SNK, P=0.028). Treatment with ATP alone also resulted in a significant decrease in cells with complete morphology (SNK, P=0.002) and a small, but significant increase in cells with membrane morphology (SNK, P=0.011). Klk6 (150 nM) amplified the gliopathic effects of ATP, further increasing the percentage of oligodendrocytes with "simple" morphology relative to ATP alone (FIG. 3D; SNK, P=0.039). The coapplication of Klk6 and ATP also resulted in greater than 40% increase in the population of oligodendrocytes with incomplete morphologies compared with vehicle (SNK, P=0.003) or ATP alone (SNK, P=0.004). The addition of Klk6 and ATP also exacerbated the reduction in mature cells seen with ATP alone and resulted in the complete loss of oligodendroglia with the mature complete (FIG. 3D; SNK, P=2.0×10$^{-4}$, ATP vs. ATP+Klk6; SNK, P=2.3×10$^{-4}$, vehicle vs. ATP+Klk6) or membrane morphologies (SNK, P=0.001, ATP vs. ATP+Klk6; SNK, P=0.033, vehicle vs. ATP+Klk6). Moreover, treatment with ATP resulted in a two-fold reduction in the number of processes per oligodendrocyte (FIG. 3E; SNK, P=2.3×10$^{-4}$) and this increased to a five-fold reduction with the co-application of Klk6 (FIG. 3E; SNK, P=2.5×10$^{-4}$). The co-application of Klk1 and ATP (FIG. 3D) did cause a significant decrease in the population of oligodendrocytes with membrane morphology (SNK, P=0.022) but did not impact process loss per cell relative to treatment with ATP alone (FIG. 3E).

Treatment of murine oligodendrocytes (3 DIV) with ATP caused a significant decrease in oligodendrocyte number relative to control (FIG. 3F; SNK, P=0.006). Treatment with Klk6 in addition to ATP caused a significant exacerbation of ATP-induced cell loss compared with ATP (FIG. 3F; SNK, P=0.046) or with vehicle alone (SNK, P=9.3×10$^{-4}$). Klk1 did not increase ATP-mediated oligodendrocyte loss (FIG. 3F).

PAR1 agonists mediate process loss in oli-neu oligodendrocytes: To determine the range of PAR1 agonists able to regulate oligodendrocyte process integrity, Oli-neu oligodendrocytes were treated with recombinant Klk6 (30, 150, and 300 nM), thrombin (270 nM), or PAR1-AP (100 μM) for 24 hours. A significant and dose-dependent (FIGS. 4A and 4B; SNK, P=0.018, Klk6 30 vs. 150 nM; SNK, P=0.041, Klk6 30 vs. 300 nM) decrease in the number of processes per cell was observed in response to Klk6 (SNK, P=1.5×10$^{-4}$, Klk6 30-150 nM vs. control). A significant decrease in Oli-neu process number was also observed following treatment with thrombin (FIGS. 4A and 4B; SNK, P=1.1×10$^{-4}$ or PAR1-AP (SNK, P=2.7×10$^{-4}$). A small but significant increase in Oli-neu cell number was also observed following treatment with the lowest concentration of Klk6 examined (FIG. 4C; 30 nM, SNK, P=0.03). A similar increase in cell number was observed in the case of treatment with PAR1-AP (SNK, P=0.003). Klk1 (300 nM) had no effect on Oli-neu process stability (FIGS. 4A and 4B) or cell number.

Klk6 blockade of OPC differentiation is PAR1-dependent: To determine whether elevated levels of Klk6 inhibit process outgrowth from OPCs, purified OPCs were treated with Klk6 (150 nM) just after plating for 24 h. Progenitor cells treated with Klk6 exhibited stunted morphological differentiation, having ~60% fewer processes per cell compared with controls (FIGS. 5A and 5B; SNK, P=2.3×10$^{-4}$). Thrombin also inhibited OPC process extension (FIGS. 5A and 5B; SNK, P=2.0×10$^{-4}$). OPCs treated with Klk1 developed processes comparable to controls (FIGS. 5A and 5B). In the case of progenitors, Klk6 treatment also significantly reduced the number of OPCs (FIG. 5C; SNK, P=0.032), while treatment with thrombin or Klk1 had no effect. To determine the role of PAR1 in mediating these effects, primary OPCs were differentiated in the presence of a selective PAR1 inhibitor, SCH79797 (50 nM), for 3 hours prior to the addition of Klk6. SCH79797 attenuated the ability of Klk6 to reduce OPC process outgrowth by ~34% (FIG. 5D; SNK, P=0.006), while treatment with the SCH79797 alone had no significant effect relative to vehicle controls.

Klk6 suppresses myelin gene expression in a PAR1-dependent fashion: To determine the impact of elevated Klk6 on other key aspects of oligodendrocyte biology, the effects of treatment with Klk6 for 24 hours on the expression of PLP and MBP and the involvement of PAR1 were evaluated. Treatment of PAR1$^{+/+}$ but not PAR$^{-/-}$ oligodendrocyte cultures with recombinant Klk6 (300 nM) for 24 hours resulted in a significant suppression of PLP (FIG. 6A; 636%, Student's t-test, P=5.9×10$^{-4}$) and MBP RNA expression (FIG. 6B; 633%, Student's t-test, P=0.029). Treatment of either PAR1$^{+/+}$ or PAR1$^{-/-}$ cells with Klk6 did not significantly alter GAPDH RNA expression (PAR1$^{+/+}$-control, 1.5×10$^6$±6.9×10$^4$ vs. PAR1$^{+/+}$-Klk6, 1.4×10$^6$±4.4×10$^4$ copies/0.5 μg RNA; PAR1$^{-/-}$-control, 1.4×10$^6$+1.3×10$^4$ vs. PAR1$^{-/-}$Klk6, 1.4×10$^6$±6.5×10$^3$ copies/0.5 μg RNA).

Parallel to the effects of Klk6 observed in primary oligodendrocytes, treatment of Oli-neu oligodendroglia with Klk6 for 24 hours also significantly diminished PLP expression (FIGS. 7A and 7B; SNK, P=8.0×10$^{-4}$), although no significant suppression of MBP RNA was observed at this time point. Notably, Klk6 caused significant and equivalent PLP RNA down regulation at 30, 150, and 300 nM (FIG. 7C; SNK, P=0.002). PLP expression was also significantly decreased by treatment with either thrombin (FIG. 7A; 270 nM; SNK, P=0.003, vs. Control) or PAR1-AP (100 μM; SNK, P=7.4×10$^{-4}$), but not recombinant Klk1 (300 nM) at the time point examined.

Role of Erk1/2 in Klk6 regulation of myelin gene expression: Based on previous data demonstrating the Klk6-mediated MAPK signaling in neurons and astrocytes (Vandell et al., supra), experiments were conducted to examine whether Klk6 triggers similar signaling in Oli-neu oligodendrocytes and the possible role of this signaling in the regulation of myelin gene expression. Treatment of Oli-neu oligodendrocytes with Klk6 for 10 minutes elicited a nearly four-fold increase in Erk1/2 phosphorylation (FIGS. 7E and 7F; SNK, P=0.012). The ability of Klk6 to induce MAPK signaling was blocked by the PAR1 inhibitor, SCH79797 (50 nM) (FIGS. 7E and 7F). No significant changes in Erk1/2 signaling were observed following treatment with SCH79797 alone or Klk1. Linking Klk6-PAR1-mediated down regulation of PLP to Erk1/2 signaling, co-treatment of Oli-neu with Klk6 and a selective MEK1/2 inhibitor (U0126, 10 μM) for 24 h, significantly diminished the ability of Klk6 to suppress PLP RNA expression (FIG. 7D; SNK, P=0.009, Klk6 vs. Klk6+U0126), although suppression was not completely blocked (SNK, P=0.034, Klk6+U0126 vs. Control). No significant change in PLP RNA expression was observed following treatment with U0126 alone.

Klk6 promotes white matter pathology in a PAR1-dependent fashion: To determine whether elevated Klk6 or deregulated PAR1-agonism alone mediate white matter pathology in vivo, and the role of PAR1 in mediating these effects, recombinant Klk6 or PAR1-AP were microinjected unilaterally into the dorsal funiculus of PAR1$^{+/+}$ or PAR1$^{-/-}$ murine spinal cord. Seventy-two hours after microinjection of Klk6 (0.02 μg total) into PAR1$^{+/+}$, over 1,200 μm of white matter surrounding the injection site presented with vacuolating myelinopathy, tissue destruction and hemorrhage in H&E stained sections, effects that were largely absent in PAR1$^{-/-}$ mice (FIG. 8A). Rostrocaudal white matter pathology mediated by Klk6 was two-fold greater than that induced by saline alone (FIG. 8D; saline control=570.0±39.3 μm vs. Klk6=1,242.0±95.3 μm; SNK, P=6.9×10$^{-4}$). Microinjection of PAR1-AP (0.02 μg) also induced significantly greater rostrocaudal white matter pathology relative to saline (FIGS. 8A and 8D; PAR1-AP=1,026.0±105.3 μm, SNK, P=0.01) and these effects were also absent in PAR1$^{-/-}$ mice. In addition, Klk6 and PAR1-AP each caused significant and largely equivalent loss of MBP-immunoreactivity across multiple sections rostrocaudally (~45% loss relative to saline alone) (FIGS. 8B and 8E; SNK, P=4.1×10$^{-4}$ and P=0.001, respectively) in PAR$^{+/+}$ but not in PAR$^{-/-}$ mice, and enhanced the maximal lesion area (FIG. 8F; Klk6, SNK, P=3.3×10$^{-4}$; PAR1-AP, SNK, P=3.2×10$^{-4}$), relative to saline alone, in PAR$^{+/+}$ but not in PAR1$^{-/-}$ mice.

To determine the effect of PAR1 agonists on white matter oligodendroglia, sections were stained for CC-1. Counts of CC-1$^+$/DAPI$^+$ cells in the dorsal columns in tissue sections encompassing the injection epicenter and for 300 μm rostrocaudally (FIGS. 8C and 8G) indicated that Klk6 and PAR1-AP each promoted a significant loss of CC-1$^+$ cells throughout the dorsal column white matter (~15% reduction, SNK, P=0.001 and P=0.002, respectively) in PAR1$^{+/+}$ but not in PAR1$^{-/-}$ mice. In PAR1$^{+/+}$ spinal cord injected with saline alone, approximately 92.4±2.0 CC-1$^+$ oligodendroglia were counted per 1.5×10$^5$, the approximate size of the dorsal column in a given tissue section. The number of CC-1V oligodendroglia after saline microinjection in PAR1$^{-/-}$ was nearly identical (93.4±1.8).

TABLE 1

Primers used for quantitative PCR of murine PAR, Klk6, and myelin genes

| Gene | Entrez accession | Primer sequences | | SEQ ID NO: |
|---|---|---|---|---|
| GAPDH | NM_008084.2 | Forward: | ACCACCATGGAGAAGGC | 1 |
| | | Reverse: | GGCATGGACTGTGGTCATGA | 2 |
| Klk6 | NM_011177.2 | Forward: | CCTACCCTGGCAAGATCAC | 3 |
| | | Reverse: | GGATCCATCTGATATGAGTGC | 4 |
| PAR1 | NM_010169.3 | Forward: | CTTGCTGATCGTCGCCC | 5 |
| | | Reverse: | TTCACCGTAGCATCTGTCCT | 6 |
| PAR2 | NM_007974.4 | Forward: | CCGGACCGAGAACCTTG | 7 |
| | | Reverse: | CGGAAGAAAGACAGTGGTCAG | 8 |
| MBP | NM_001025251 | Forward: | CCAGTAGTCCATTTCTTCAAGAACAT | 9 |
| | | Reverse: | GCCGATTTATAGTCGGAAGCTC | 10 |
| PLP | NM_011123.2 | Forward: | TCTTTGGCGACTACAAGACCAC | 11 |
| | | Reverse: | CACAAACTTGTCGGGATGTCCTA | 12 |

GAPDH, Glyceraldehyde phosphate 3-dehydrogenase; Klk6, kallikrein-related peptidase 6; PAR1, protease-activated receptor 1; PAR2, protease-activated receptor 2; MBP, myelin basic protein; PLP, proteolipid protein.

TABLE 2

Quantitative PCR Analysis Demonstrates Robust Expression of Klk6, PAR1, and PAR2 by Murine Primary and Oli-neu Oligodendroglia

| | RNA copy number | | | |
|---|---|---|---|---|
| Gene | Primary oligodendrocyte progenitor cell | Primary differentiated oligodendrocyte | Oli-neu | Oli-neu1dbcAMP |
| Klk6 | 6.0E+03 (±2.2E+02) | 5.6E+03 (6 8.7E+01) | 6.4E+04 (±2.2E+04) | 2.0E+04 (±4.0E+03) |
| PAR1 | 1.1E+06 (±5.7E+04) | 8.6E+05 (6 3.6E+04) | 1.5E+06 (±2.2E+05) | 1.3E+06 (±3.3E+05) |
| PAR2 | 2.5E+02 (±2.3E+01) | 2.9E+02 (±2.1E+01) | 3.1E+03 (±1.6E+02) | 3.5E+03 (±2.3E+01) |
| GAPDH | 6.0E+06 (±1.3E+05) | 6.5E+06 (±2.9E+05) | 2.4E+07 (±6.7E+05) | 1.8E+07 (±2.9E+05) |

The mean number of RNA copies encoding for Klk6, PAR1, and PAR2 RNA in 0.5 μg of total RNA isolated from immediately post purification OPCs, mature oligodendrocytes (3DIV), undifferentiated (Oli-neu), or differentiated Oli-neu (Oli-neu + dbcAMP) oligodendrocytes is provided (±SEM). Amplification of GAPDH was carried out to verify equal loading.

Example 2—the Thrombin Receptor is a Critical Extracellular Switch Controlling Myelination Materials and Methods Animal care and use: Mice genetically deficient in PAR1 (PAR1$^{-/-}$, B6.129S4-F2r$^{tm1Ajc}$/J) were obtained from Jackson (Bar Harbor, ME) and backcrossed to C57BL6/J for more than 30 generations (Burda et al., supra; Yoon et al., supra). PAR1$^{+/+}$ littermates served as controls.

Quantification of myelin protein expression using Western blot: Western blots were used to quantify myelin and signaling proteins. Whole spinal cords were harvested from three individual PAR1$^{+/+}$ or PAR1$^{-/-}$ mice on postnatal day (P) 0, 7, 21 or 45 (adulthood). Spinal cords at each time point were collectively homogenized in radio-immunoprecipitation assay buffer and 25 µg of protein resolved on sodium dodecyl sulfate-polyacrylamide gels (Bio-Rad Laboratories, Hercules, CA). Multiple electroblotted membranes were used to sequentially probe for antigens of interest, including myelin proteins PLP (Ab28486, Abcam, Cambridge, MA), MBP (MAB386, Chemicon, Billerica, MA), and CNPase (MAB326, Millipore. Billerica, MA); oligodendrocyte proteins, Olig2 (Ab9610, Millipore); neuron specific proteins, Neurofilament H or L (N4142, N5139, Sigma, St. Louis, MO); or the phosphorylated or total protein forms of select signaling proteins, ERK1/2 (9101S, 9102S, Cell signaling, Boston, MA), protein kinase B (AKT, 4058L, 9272S, Cell signaling) or signal transducer and activator of transcription 3 (STAT3, sc-8059, sc-8019, Santa Cruz, Santa Cruz, CA). Membranes were re-probed for β-actin (NB600-501, Novus Biological, Littleton, CO, USA) and the relative optical density (ROD) of each protein of interest normalized to that of Actin. The mean and standard error (s.e.) of ROD readings across at least 3 independent Westerns was used for statistical comparisons (Yoon et al., supra).

PAR1 expression by oligodendrocytes and quantification of oligodendrocyte number in the developing mouse spinal cord: To evaluate whether the PAR1-regulated changes in myelin proteins and myelin gene expression reflect changes in the number of OPCs or mature oligodendroglia, Olig2 (Ab9610, Millipore) or CC-1/APC 1 (adenomatous polyposis coli, Ab16794, Abcam, Cambridge, MA) immunopositive cells were enumerated in 5 µm paraffin sections through the dorsal columns of P0, 7, 21 or 45 spinal cords. Olig2 is a basic helix-loop-helix transcription factor expressed by OPCs and mature oligodendroglia, whereas CC-1 is associated only with the mature phenotype (Ligon et al., *Glia* 54:1-10, 2006; Funfschilling et al., *Nature* 485:517-521, 2012; Burda et al., supra). Immunoperoxidase stained sections were cover slipped with Hardset containing DAPI (Vector, Burlingame, CA) and digitally imaged (Olympus BX51 microscope, Olympus, Center Valley, PA). Counts were made of either Olig2 or CC1+ cells with a DAPI stained nucleus within the entire dorsal column of at least 3 mice at each time point without knowledge of genotype. The association of PAR1 with spinal cord oligodendrocytes was evaluated by co-immunolabeling for PAR1 (sc-5606, clone H-111, Santa Cruz) and CC-1.

Myelin RNA and protein expression by OPCs and oligodendroglia in vitro: To determine whether the absence of PAR1 directly impacts myelin expression, real time reverse transcription PCR was used to determine the level of oligodendrocyte associated gene transcripts in OPCs freshly shaken from PAR1$^{+/+}$ or PAR1$^{-/-}$ mixed glial cultures or after a 72 hour period of differentiation in vitro. Mixed glial cultures were prepared from the cortices of P1 mice according to a modified McCarthy and de Vellis protocol (Burda et al., supra). Zero hour OPC RNA was obtained from cells immediately after shaking from 10 day-in-vitro mixed glial cultures. Alternatively, OPCs were differentiated for 72 hours prior to RNA isolation by plating at 3×10$^4$/cm$^2$ cells per well on poly-L-lysine (PLL, 10 µg/mL) coated 6-well plates in Neurobasal A media containing 1% N2, 50 U/mL penicillin/streptomycin, 2 mM Glutamax, 1 mM sodium pyruvate and 0.45% glucose. The level of RNA encoding PAR1, MBP, PLP, CNPase, MAG, MOG, NogoA or Olig2 was determined in 0.10 µg of RNA in triplicate using an iCycler iQ5 system (BioRad) with primers described in Table 3 (Burda et al., supra). Results were repeated twice from independent cell preparations with parallel results. The relative amount of RNA at each time point was normalized to the constitutively expressed gene Rn18S. Mean expression levels in cells derived from PAR1$^{-/-}$ mice were expressed as a percent of the level observed in cells derived from wild type mice.

The impact of PAR1 genetic deletion on the expression of PLP protein in vitro was determined by comparing PLP-immunoreactivity (Ab28486, Abcam) in 72 hour differentiated PAR1$^{+/+}$ or PAR1$^{-/-}$ oligodendrocytes plated at 7×10$^4$/cm$^2$ on PLL coated 12 mm glass cover slips. Five 20× fields encompassing the poles and center of each coverslip were captured digitally and Image J software was used to determine the ROD of somal PLP staining as well as somal area. The mean number of PLP$^+$ cells was also enumerated and expressed as a ratio of the number of DAPI cells present in each field.

Analysis of the number of myelinated nerve fibers and myelin thickness: The number of myelinated nerve fibers and the thickness of myelin sheaths were determined by structural and ultrastructural analysis of the spinal cord dorsal column white matter at P0 and P45. Mice were perfused with Trump's fixative (4% formaldehyde with 1% glutaraldehyde, pH 7.4) and a 1 mm segment of the cervical spinal cord was osmicated and embedded in araldite. The number of myelinated nerve fibers was counted in 1 µm semi-thin sections stained with 4% p-phenylenediamine to visualize the myelin sheaths. Digital images capturing the entire dorsal-ventral and lateral-medial axis of the spinal cord dorsal columns were captured at 60×. The number of myelinated nerve fibers and their diameter was automatically quantified from digital images using a batch algorithm generated in Matlab (The Mathworks, Narrick, MA) (Denic et al., *Ann Neurol* 66:559-564, 2009). For P45 spinal cords, the number of myelinated nerve fibers that were <4 µm$^2$, 4-10 µm$^2$ or >10 µm$^2$ was also examined. All myelinated nerve fiber counts for each genotype were averaged across at least 3 independent animals per time point.

Myelin sheath thickness in the dorsal column of the cervical spinal cord at P0 and P45 was quantified in ultrathin (0.1 µm) sections taken from araldite blocks using a JEM-1400 Transmission Electron Microscope (JEOL USA, Inc., Peabody, MA). Images were captured at 8000× without knowledge of genotype and included 5 fields across the dorsal-ventral axis of the dorsal column at P0 and 6 fields at P45. G-ratios were calculated from all myelinated axons in each image. Across 3 animals per time point this resulted in measurement of roughly 60 myelinated fibers at P0 and 2200 at P45 for each genotype. Measurements of axon diameter (d) and myelin fiber diameter (D) were made using Image J software and presented as mean g-ratio (d/D) or myelin thickness±s.e. across axon diameters.

Evaluation of locomotor activity: Potential differences in locomotor activity between PAR1$^{+/+}$ and PAR1$^{-/-}$ mice were evaluated using a Comprehensive Laboratory Animal Monitoring System (Columbus Instruments, Columbus OH). Animals were housed in the system and total activity, ambulatory activity, and rearing data collected for a period of 72 hours that included a 24 hour period of acclimation followed by 24 hour fed and 24 hour fasted periods. The mean activity across genotypes in each case (PAR$^{+/+}$, n=11 or PAR1$^{-/-}$, n=12) was analyzed for light and dark periods under both fed and fasted conditions.

Statistical comparisons: All data were expressed as mean±s.e. Comparisons between multiple groups were made using a One-Way Analysis of Variance (ANOVA) and the Newman Keuls post-hoc test. When multiple comparison data was found to be not normally distributed, the Kruskal-Wallis ANOVA on Ranks was applied with Dunn's method. For pairwise comparisons between two groups the Students unpaired t-test was used. Statistical significance was set at $P<0.05$.

Results

Figures 9A, 9B:
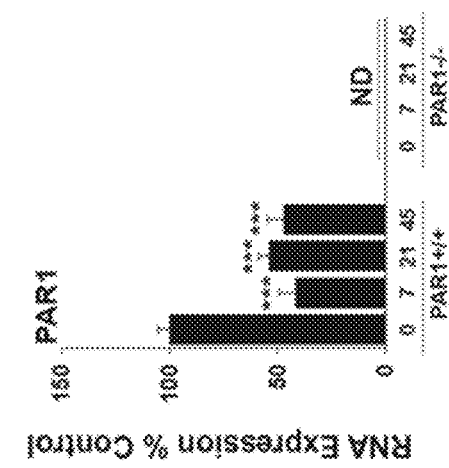
FIGS. 9A and 9B show that PAR1 expression in the spinal cord is developmentally regulated and localized in part to oligodendroglia.
Figure 15:
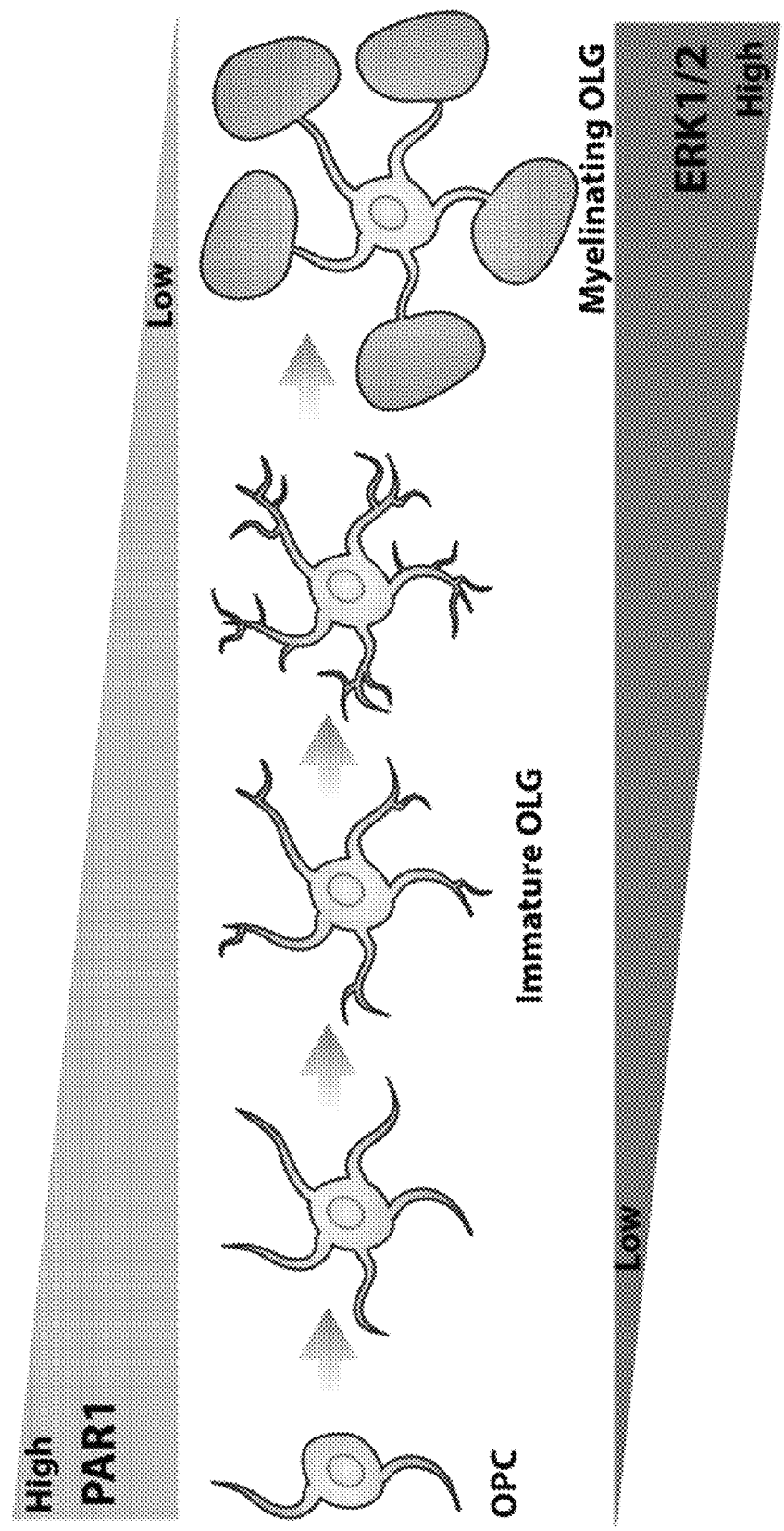
FIG. 15 is a diagram of a model by which PAR1 may suppress oligodendrocyte precursor cell differentiation by limiting ERK1/2 signaling. The findings presented herein suggest that high levels of OPC PAR1 expression limit the capacity of oligodendrocyte precursor cells to differentiate towards a myelinating phenotype. Genetic-loss-of PAR1 function is associated with elevated levels of the ERK1/2 signaling intermediate, an established mediator of myelination (Fyffe-Maricich et al., *J Neurosci* 31:843-850, 2011; Ishii et al., *J Neurosci* 33:175-186, 2013). Taken together, the data presented herein support a model in which PAR1 limits CNS myelination by limiting ERK1/2 signaling.

PAR1 is expressed by oligodendroglia and levels are inversely correlated with the onset of spinal cord myelination: To determine the significance of PAR1 to myelination of the spinal cord, the expression of PAR1 RNA was evaluated using quantitative real time PCR. Two-fold reductions in PAR1 RNA were observed in the spinal cord by P7 and this lower level persisted through adulthood (FIG. 9A, $P<0.001$, Newman Keuls). Perinatal reductions in PAR1 RNA, when the levels of many myelin proteins begin to surge (FIGS. 10A-10G), supports an emerging model in which high levels of PAR1 signaling at birth engage a negative signaling cascade that suppresses myelination (FIG. 15).

PAR1 immunoreactivity was co-localized to CC-1 positive oligodendroglia in the spinal cord white matter at all post-term intervals examined (FIG. 9B). PAR1 has also been functionally linked to neurons (Hamill et al., Exp Neurol 217:136-146, 2009; Yoon et al., supra) and astroglia (Nicole et al., J Neurosci 25:4319-4329, 2005; Vandell et al., supra; Scarisbrick et al. 2012a, supra) and non-CC-1-immunostained cells were also immunoreactive for PAR1 in the perinatal and adult spinal cord.

Figure 10A:
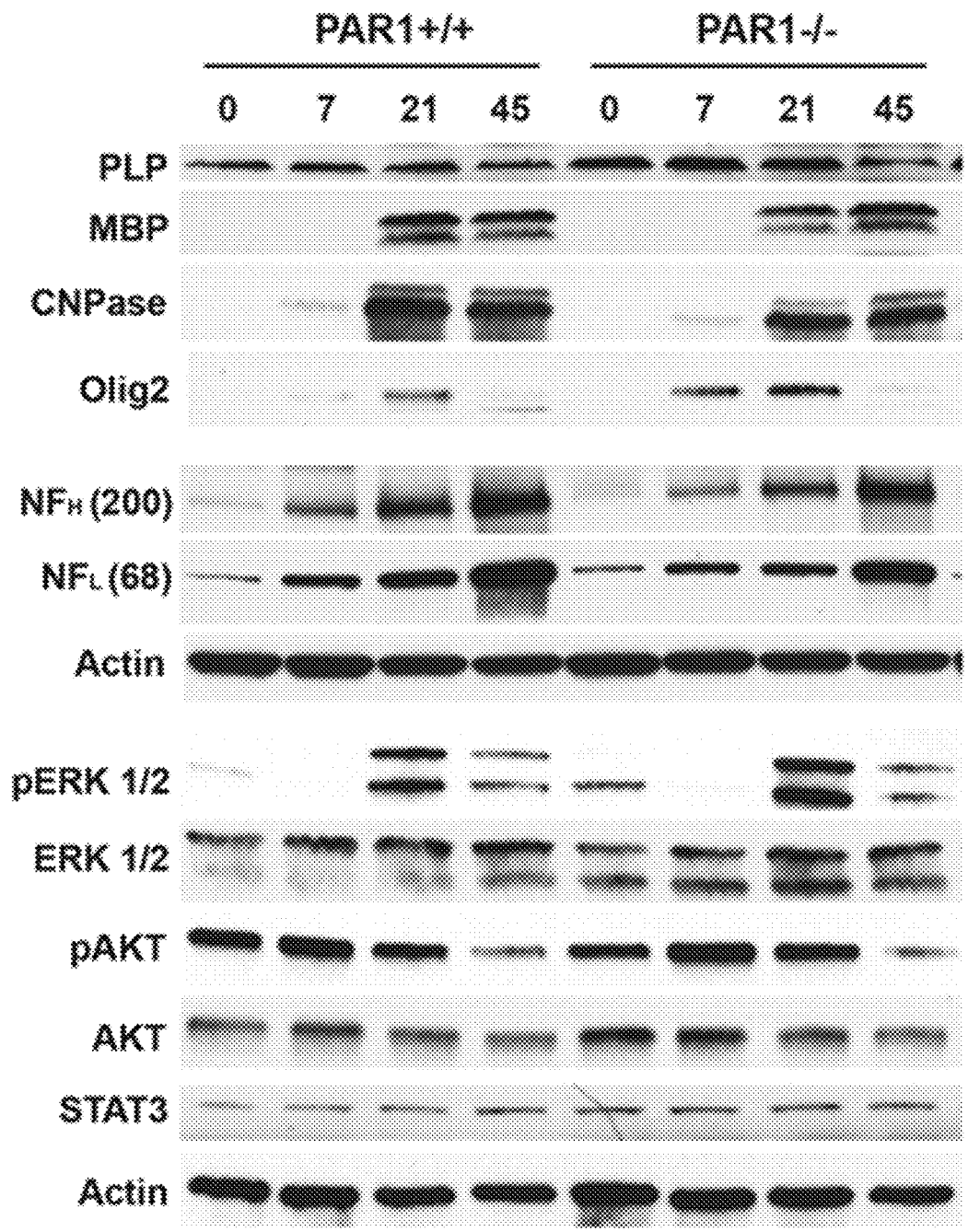

Knockout of PAR1 results in accelerated PLP expression in the perinatal period and higher levels of MBP in adults: To critically evaluate the role of PAR1 in myelin development in vivo, the onset, magnitude, and duration of myelin protein expression, including the two major myelin structural proteins, PLP and MBP, were directly compared in the spinal cord of PAR1$^{+/+}$ and PAR1$^{-/-}$ mice at P0 through P45 (adulthood) (FIGS. 10A-10C). Consistent with a regulatory role for PAR1 in the onset of myelin protein expression, spinal cord PLP levels were 2.4-fold higher at P0 in PAR1$^{-/-}$ mice relative to PAR1$^{+/+}$ mice ($P=0.003$, Neuman Keuls). Also, peak PLP levels were achieved by P7 in the absence of PAR1, 2 weeks ahead of the P21 peak observed in the wild type spinal cord ($P=0.03$, Newman Keuls). Supporting a unique role for PAR1 in regulating the onset of PLP production, despite the earlier commencement of spinal cord PLP protein expression in PAR1$^{-/-}$ mice, by P21, and at P45, levels were identical across genotypes. These data highlight a key role for PAR1 in regulating the early stages of PLP protein production.

The developmental onset of MBP protein detectable by Western blot occurred well after that of PLP, being first observed in spinal cord samples by P21, when levels were comparable between PAR$^{+/+}$ and PAR1$^{-/-}$ mice (FIGS. 10A and 10C). By adulthood, however, MBP protein levels were 1.7-fold higher in PAR1$^{-/-}$ mice ($P=0.02$, Newman Keuls). The manifestation of higher MBP protein levels in adult PAR1$^{-/-}$ mice is consistent with the model that blocking PAR1 signaling creates a microenvironment that enhances myelin production (FIG. 15) (Burda et al., supra). By contrast to the elevated levels of PLP and MBP protein seen in the spinal cord in the absence of PAR1, levels of 2',3'-cyclic-nucleotide 3'-phosphodiesterase (CNPase), were reduced by 1.4-fold on P21 (FIGS. 10A and 10D; $P=0.03$, Newman Keuls). No impact of PAR1 deletion was seen on the heavy or light chains of neurofilament protein (NFH or NFL) at any age examined (FIGS. 10A, 10F, and 10G).

PAR1 is a negative regulator of ERK1/2 signaling in the spinal cord across the lifespan: To determine the likely intracellular signaling cascade(s) impacted by PAR1, extracellular-signal-related kinase (ERK1/2) and AKT (protein kinase B) were evaluated, since each of these signaling intermediates participate in myelin development (Czopka et al., J Neuroscience 30:12310-12322, 2010; Harrington et al., Ann Neurol 68:703-716, 2010; Guardiola-Diaz et al., Glia 60:476-486, 2012; Ishii et al., J Neurosci 32:8855-8864, 2012; Fyffe-Maricich et al., J Neurosci 33:18402-18408, 2013; and Ishii et al. 2013, supra). Levels of the transcription factor signal transducer and activator of transcription 3 (STAT3) which has been both indirectly (see Nobuta et al., Ann Neurol 72:750-765, 2012) and directly (Dell' Albani et al., J Neurosci Res 54:191-205, 1998) linked to oligodendrocyte differentiation was also examined in parallel. Consistent with prior studies demonstrating that elevations in ERK1/2 promote hypermyelination, substantial elevations in ERK1/2 were found in the spinal cords of PAR1$^{-/-}$ mice from P7 through the adult period (FIGS. 10A and 10K; $P=0.03$, Newman Keuls). Peak elevations in ERK1/2 in PAR1$^{-/-}$ spinal cords were seen at P7 and P21 when levels were 1.7-fold higher than those observed in wild type mice. Elevated levels of activated ERK1/2 (1.3-fold) were also detected in PAR1$^{-/-}$ spinal cords on P21 (FIGS. 10A and 10H; $P=0.008$, Newman Keuls). Levels of activated AKT were also elevated in the PAR1$^{-/-}$ spinal cord on P7 relative to the level detected at birth (FIGS. 10A and 10I), an elevation not seen in WT mice. A significant difference in total AKT levels was not observed (FIG. 10L). PAR1-loss-of-function also had little impact on STAT3 signaling pathway (FIGS. 10A, 10J, and 10M).

Knockout of PAR1 increases oligodendrocyte number in the early postnatal period: To determine whether increases in PLP and MBP protein in the spinal cord of PAR1$^{-/-}$ mice reflect increases in myelin protein expression per cell, or alternatively, more myelin producing oligodendroglia, protein levels of oligodendrocyte transcription factor 2 (Olig2) were quantified from P0 through adulthood (FIGS. 10A and 10E). Findings regarding overall levels of Olig2 in the spinal cord were complemented by counts of Olig2- or adenomatous polyposis coli (CC-1)-immunoreactive oligodendrocytes in the dorsal column of parallel sets of mice (FIGS. 11A and 11B). Olig2 protein levels detected by Western blot were higher in spinal cords of PAR1$^{-/-}$ compared to PAR1$^{+/+}$ mice at P7 (2.6 fold, $P=0.04$) and P21 (1.6-fold, $P=0.02$) (FIG. 10E, Newman Keuls), but not in adults. In parallel, counts of Olig2+ cells revealed significantly greater numbers in PAR1$^{-/-}$ at P0 (1.5-fold, $P=0.04$) and P7 (1.3-fold, $P=0.05$), but identical numbers thereafter (FIGS. 11A and 11B, Newman Keuls). Also, counts of CC-1-immunoreactive oligodendrocytes indicated increased numbers in the dorsal columns of PAR1$^{-/-}$ mice on P7 (1.6-fold, $P=0.03$) (FIGS. 11C and 11D, Newman Keuls).

Figure 12A:
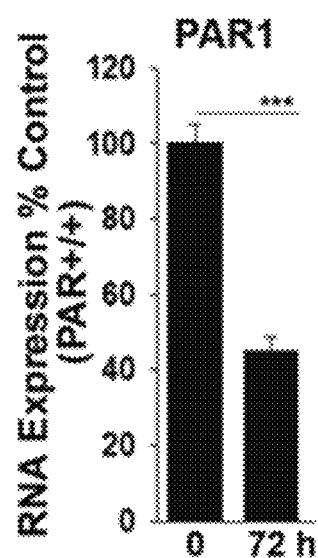
Figure 12B:
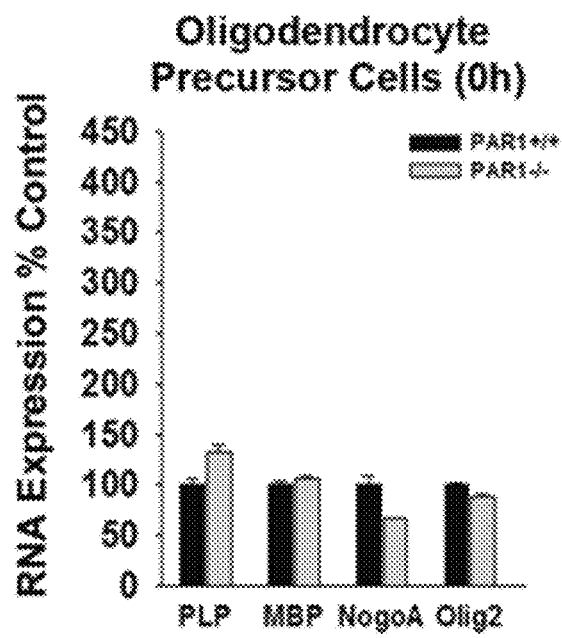
Figure 12C:
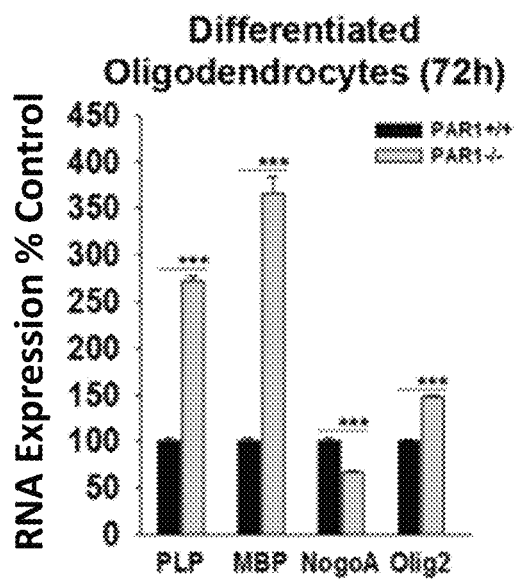

PAR1-loss-of-function enhances myelin expression in purified OPCs and differentiated oligodendroglia in vitro: To determine whether reductions in PAR1 at the level of the oligodendrocyte directly impact myelin expression, the appearance of RNA encoding myelin proteins were evaluated in freshly isolated PAR1$^{+/+}$ or PAR1$^{-/-}$ OPCs, or after a 72 hour period of differentiation in vitro (FIGS. 12B and 12C). Consistent with a suppressive role of PAR1 in the process of myelination (FIG. 15), CNPase (1.2-fold, P=0.002) and MOG (2.4-fold, P=0.04) RNA transcripts were significantly elevated in OPCs lacking PAR1 (Newman Keuls). Moreover, PLP (2.7 fold, P=0.00001), MBP (3.7-fold, P=0.0001), CNPase (1.4-fold, P=0.009), myelin oligodendrocyte glycoprotein (MOG) (4.4-fold, P=0.003), myelin associated glycoprotein (MAG) (1.5-fold, P=0.004) and Olig2 (1.5-fold, P=0.00002) RNA transcripts were all elevated in PAR1$^{-/-}$ oligodendroglia after 72 hours in culture (Newman Keuls). By contrast, transcripts encoding NogoA were reduced in PAR1$^{-/-}$ oligodendroglia after differentiation (1.5-fold, P=0.0007, Newman Keuls). These findings were complemented by examination of PLP-immunoreactivity in parallel 72 hours differentiated cultures which showed that PLP-immunoreactivity occurred at a higher level (1.9-fold, P=0.02×10$^{-5}$) and in more oligodendrocytes (1.3-fold more, P=0.03×10$^{-5}$) in cultures derived from PAR1$^{-/-}$ relative to PAR1$^{+/+}$ mice (Newman Keuls). Supporting a model in which reductions in PAR1 promote oligodendrocyte differentiation, PAR1 RNA levels were 2.2-fold higher in freshly shaken OPCs compared to those differentiated for 72 hours in vitro (P=0.0005, Students unpaired t-test, FIG. 12A).

Figure 12D:
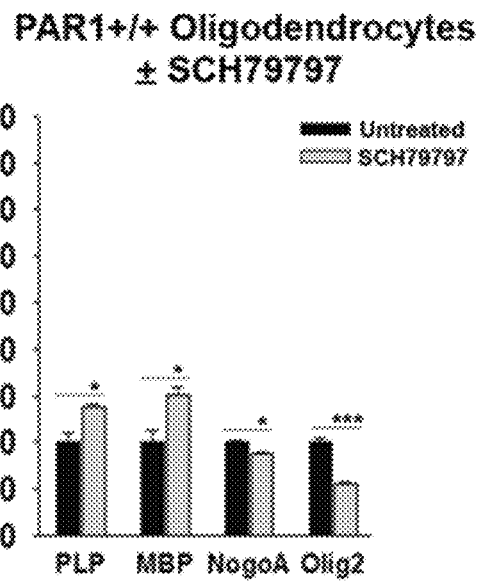

Treatment of oligodendrocytes (24 hours in culture) with 70 nM SCH79797 (a small molecule inhibitor of PAR1) for 48 hours promoted a significant increase in the expression of PLP and MBP RNA, and a decrease in NogoA and Olig2 RNA (FIG. 12D). Immunostaining of PAR1$^{+/+}$ and PAR1$^{-/-}$ OPCs differentiated for 72 hours in vitro revealed that PAR1-loss-of-function (PAR1$^{-/-}$) was associated with a significant increase in the number of PLP-immunoreactive cells (1.3-fold more, *P=0.03×10$^{-5}$) as well as the amount of PLP-immunoreactivity (ROD) per somal area (1.9-fold, *P=0.02×10$^{-5}$) (FIGS. 12E and 12F). Scale bar=20 μm.

Figure 13A:
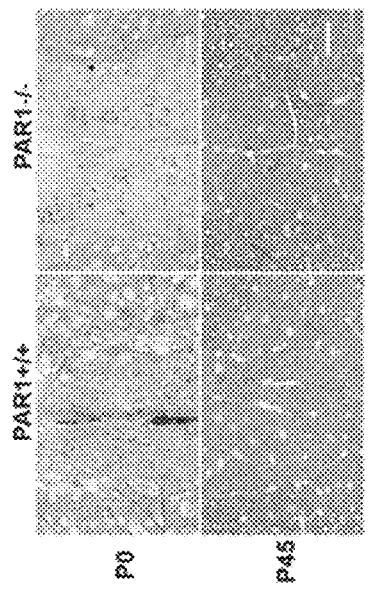
FIGS. 13A-13E include a series of photomicrographs, electron micrographs, and plots showing that myelination occurs earlier and the thickness of the myelin sheath attained is greater in the spinal cord of PAR1$^{-/-}$ mice. The photomicrographs of FIG. 13A show examples of paraphenylenediamine stained myelin sheaths in the dorsal column of P0 and P45 mice. More myelinated axons were counted in the spinal cord dorsal column white matter of PAR1$^{-/-}$ relative to PAR$^{+/+}$ mice on P0 (*P=0.02, Students unpaired t-test) (FIG. 13B). At P45, parallel numbers of myelinated axons were observed in PAR1$^{+/+}$ and PAR1$^{-/-}$ mice, but the number of myelinated fibers with a diameter of 10 µm$^2$ or greater was significantly greater in mice lacking PAR1 (*P=0.02, Students unpaired t-test).
Figure 13B:
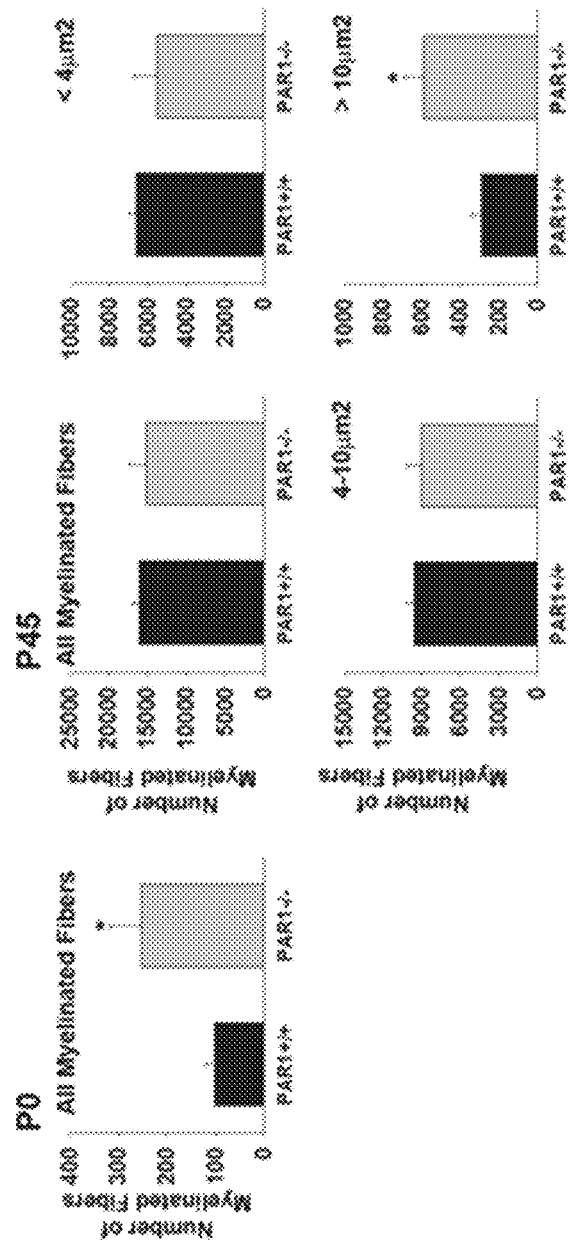
Figure 13C:
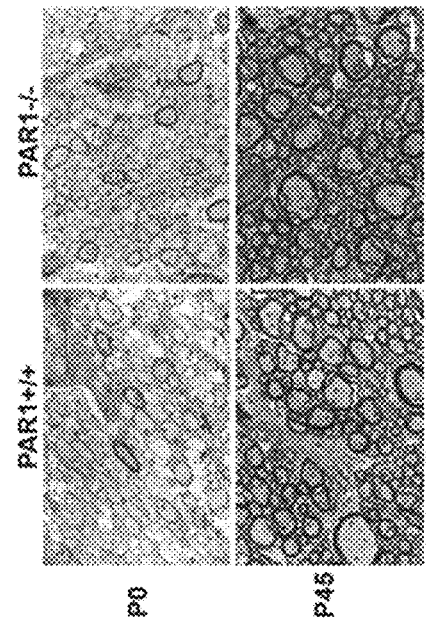
Figure 13D:
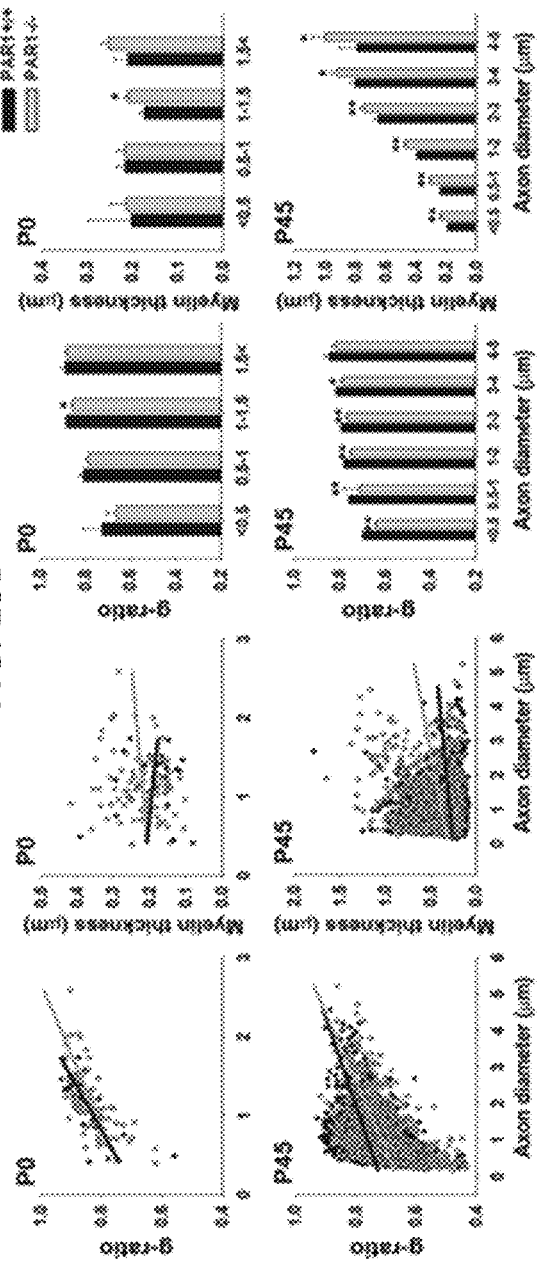
Figure 13E:
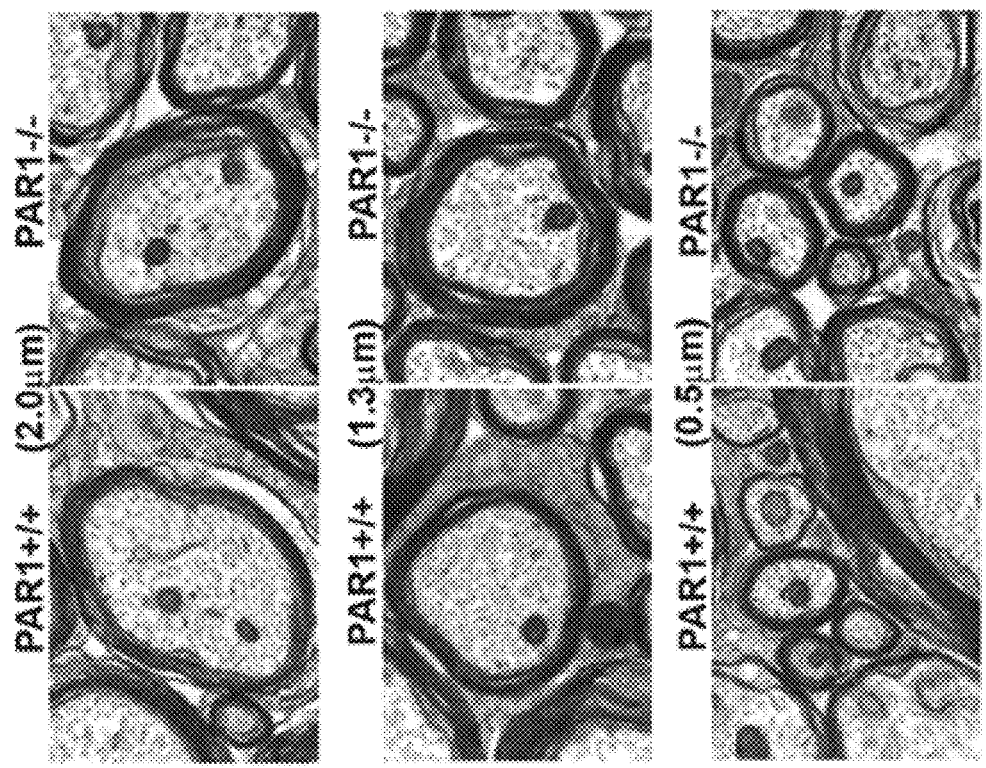

PAR1 regulates the onset of axon ensheathment and myelin thickness in adults: To determine whether the increases observed in PLP and MBP proteins in the spinal cord of PAR1$^{-/-}$ mice were reflected in changes in myelin structure, the impact of PAR1-loss-of-function on the onset of axon ensheathment and myelin thickness in the dorsal funiculi was systematically evaluated (FIGS. 13A-13D). The number of myelinated nerve fibers and their size were determined at P0 and P45 in paraphenylenediamine stained semithin (1 μm) spinal cord sections. There were nearly two-fold more thinly myelinated nerve fibers in the dorsal funiculi of PAR1$^{-/-}$ mice at P0 (252±65) relative to wild type littermates (100±19) (FIGS. 13A and 13B; mean±s.e., P=0.02, Students unpaired t-test). By P45, the number of myelinated nerve fibers was no longer different, however, PAR1$^{-/-}$ mice had significantly more myelinated nerve fibers that were >10 μm$^2$ (P=0.02, Students unpaired t-test). To delineate whether this shift in the size distribution of myelinated nerve fibers reflected an increase in myelin thickness or a shift in the size distribution of axons, the g-ratio of dorsal funiculi myelinated fibers at P0 and P45 in ultrathin (0.1 μm) sections was assessed by electron microscopy. At P0, the g-ratio of axons 1-1.5 μm was reduced in PAR1$^{-/-}$ mice, reflecting increased myelin thickness (FIGS. 13C and 13D; P=0.01, Students unpaired t-test). At P45, the g-ratios of dorsal column axons in PAR1$^{-/-}$ mice were also significantly lower across the majority of axon diameters and absolute increases in myelin thickness occurred across all axon diameters (FIGS. 13C and 13E; P≤0.02, Students unpaired t-test). Thus, not only does axon ensheathment and myelination occur earlier in the spinal cord of mice lacking the thrombin receptor, but the thickness of the myelin sheath ultimately achieved in adults is also enhanced.

Motor Activity in PAR1$^{-/-}$ mice: To link changes in spinal cord myelination observed in PAR1$^{-/-}$ mice to function, overall motor activity, ambulation and rearing were evaluated during diurnal and nocturnal cycles under both fed and fasted conditions (FIG. 14). Overall activity of mice lacking the thrombin receptor was increased during the day under fed conditions (P=0.04) and at night when fasted (P=0.02) (Students unpaired t-test, FIG. 14A). Also, both ambulation (P=0.02) and rearing responses (P=0.04) were increased in thrombin receptor-deficient mice under fasting conditions at night (Students unpaired t-test, FIGS. 14B and 14C).

TABLE 3

Primers used for quantitative real-time PCR

| Gene | Accession number | Primer Sequence Forward/Reverse | SEQ ID NO: |
|---|---|---|---|
| CNPase | NM_001146318.1 | Forward: CAAATTCTGTGACTACGGG | 13 |
| | | Reverse: GGCCTTGCCATACGA | 14 |
| MAG | NM_010758.2 | Applied Biosystems, Assay ID: Mm00487538_m1 | |
| MBP | NM_001025251 | Forward: CCAGTAGTCCATTTCTTCAAGAACAT | 15 |
| | | Reverse: GCCGATTTATAGTCGGAAGCTC | 16 |
| MOG | NM_010814.2 | Applied Biosystems, Assay ID: Mm00447824_m1 | |
| NogoA | NM_024226.4 | Applied Biosystems, Assay ID: Mm00445861.m1 | |
| Olig2 | NM_016967 | Assay ID: Mm.PT.56a.42319010 | |
| PAR1 | NM_010169.3 | Forward: CTTGCTGATCGTCGCCC | 17 |
| | | Reverse: TTCACCGTAGCATCTGTCCT | 18 |

TABLE 3-continued

Primers used for quantitative real-time PCR

| Gene | Accession number | Primer Sequence Forward/Reverse | SEQ ID NO: |
|---|---|---|---|
| PLP | NM_011123.2 | Forward: TCTTTGGCGACTACAAGACCAC | 19 |
|  |  | Reverse: CACAAACTTGTCGGGATGTCCTA | 20 |
| Rn18S | NR_003278.3 | Applied Biosystems, Assay ID: Mm03928990_g1 | |

All primers were obtained from Integrated DNA Technologies (IDT) unless otherwise indicated.

Figure 16:
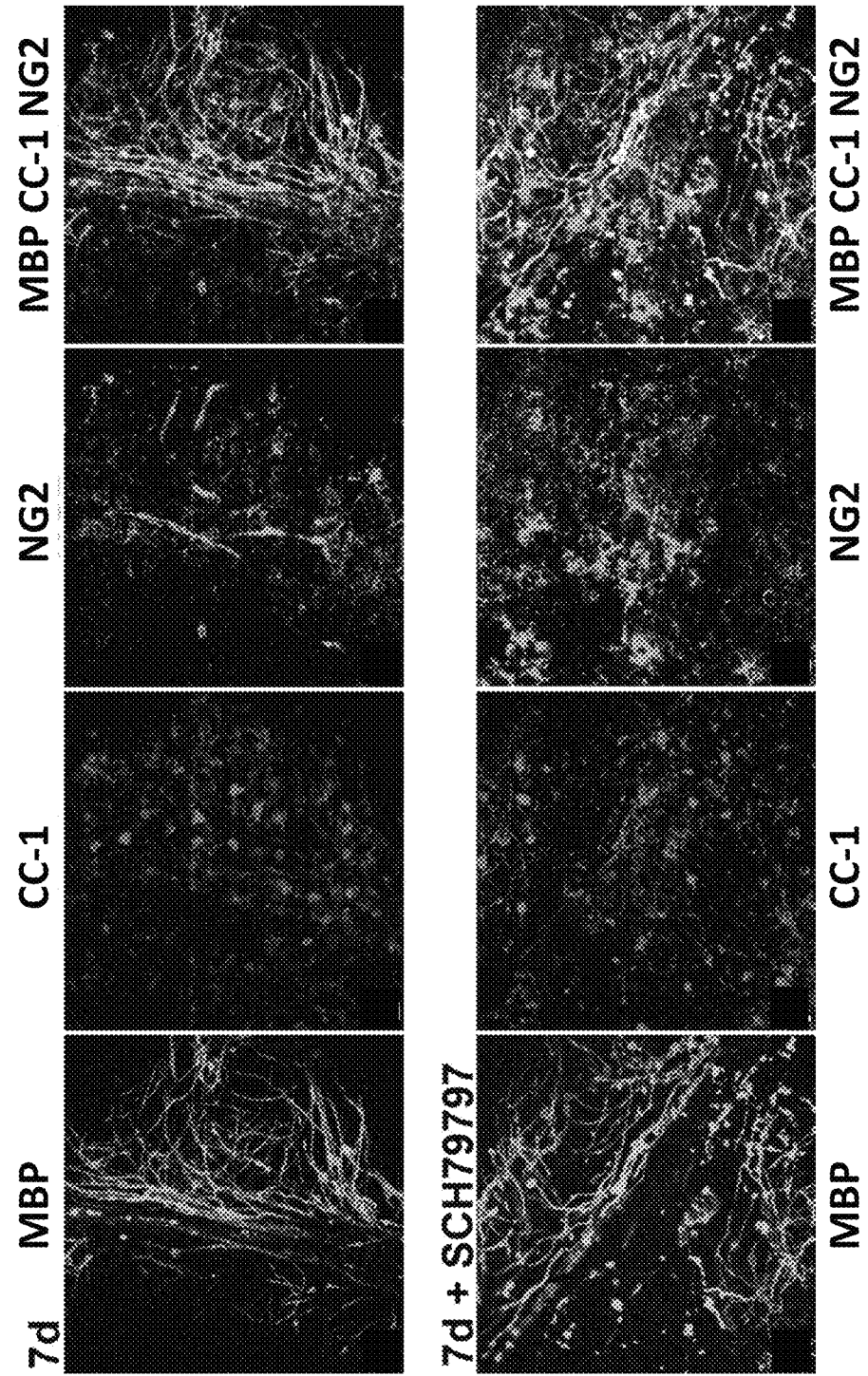
FIG. 16 is a series of photomicrographs showing cerebellar slices from postnatal day 8 mouse brain after they were grown in cell culture for 7 days in the presence (bottom panels) or absence (top panels) of SCH79797, a small molecule inhibitor of PAR1, and then stained using immunofluorescence techniques for myelin associated makers, including MBP, a marker of mature oligodendrocytes (CC-1), and for a marker of oligodendrocyte progenitor cells (NG2), as indicated. Photomicrographs show staining for each individual antigen or for all of the antigens collectively in a single slice (right panels).

Pharmacologic inhibition of PAR1 in an organotypic cerebellar slice culture system: Cerebellar slices (350 μm) from postnatal day 8 mouse brain were grown in cell culture for 7 days in the presence or absence of 70 nM SCH79797, a small molecule inhibitor of PAR1. Cerebellar slices were then fixed with 2% paraformaldehyde and stained using immunofluorescence techniques for myelin associated makers, including MBP, a marker of mature oligodendrocytes (CC-1), and for a marker of oligodendrocyte progenitor cells (NG2). The photomicrographs in FIG. 16 show staining for each individual antigen, or for all of the antigens collectively in a single slice, as indicated. Relative to control cerebellar slices (top panels), slices treated with SCH79797 (bottom panels) showed significant increases in the abundance of MBP, in the number of mature oligodendrocytes (CC-1), and the number of progenitor cells positive for the NG2 antigen. These findings suggested that inhibition of PAR1 promotes myelination in an organotypic cerebellar slice culture system.

Figure 17:
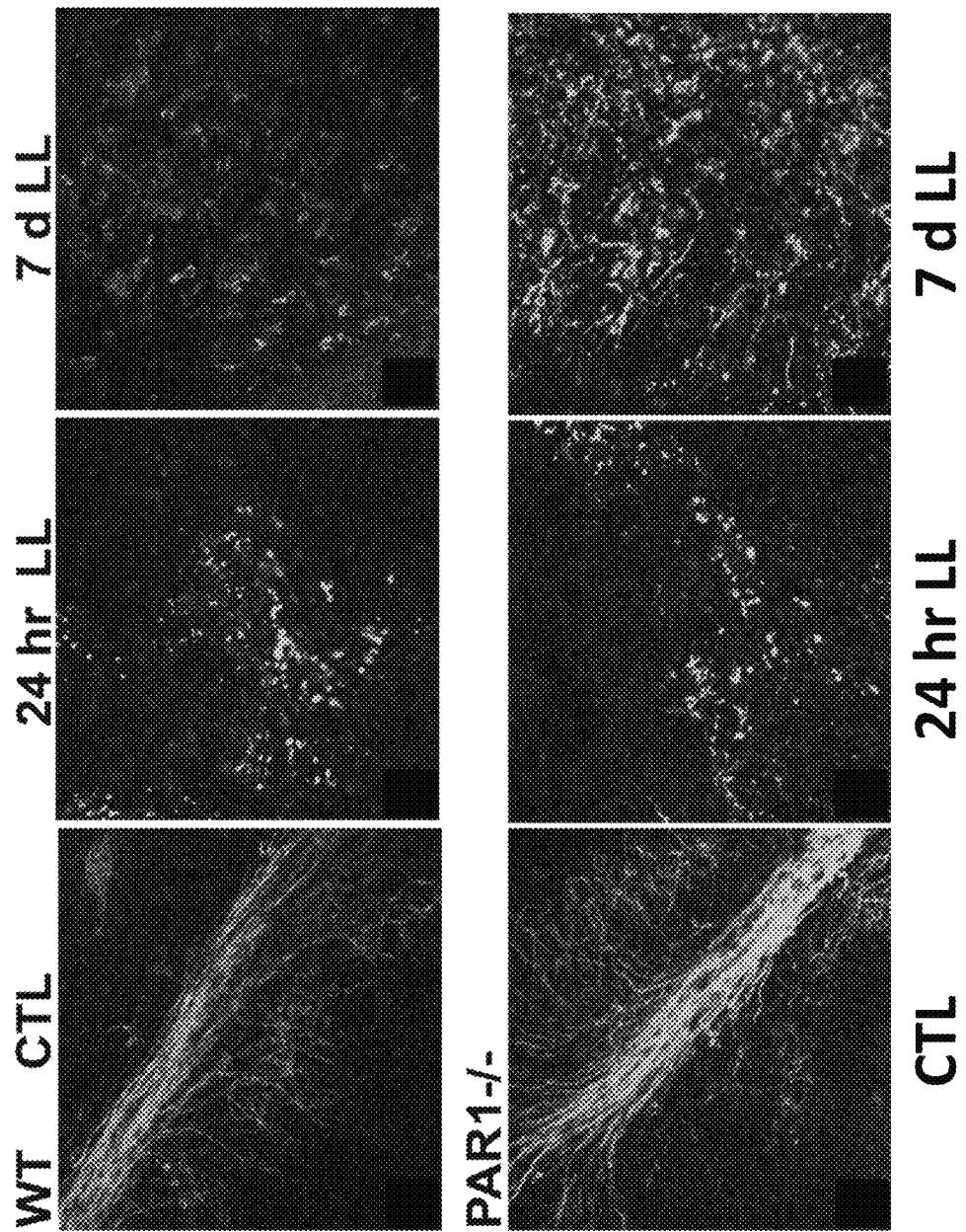
FIG. 17 is a series of photomicrographs showing cerebellar slices that were prepared from the brains of postnatal day 8 mice, grown in culture for 72 hours, treated with a demyelinating agent (Lysolecithin; LL) for 24 hours, cultured for 7 days, fixed, and stained using immunofluorescence techniques for MBP to gauge myelin regeneration.

Myelin regeneration after demyelinating injury in vitro: Cerebellar slices (350 m) were prepared from the brains of postnatal day 8 mice and grown in culture for 72 hours. Slices were then treated with a demyelinating agent (Lysolecithin; LL) for 24 hours, followed by an additional seven day culture period to visualize the process of myelin regeneration. All cerebellar slices were fixed with 2% paraformaldehyde and stained using immunofluorescence techniques for MBP to gauge myelin abundance. Cerebellar slices cultured from PAR1 gene deficient mice were associated with significantly more myelin repair (immunofluorescence for MBP; FIG. 17, bottom panels) relative to PAR1$^{+/+}$ slices (FIG. 17, top panels) seven days after a demyelinating lesion. These results suggested that blocking PAR1 can improve myelin regeneration in the central nervous system.

Remyelination in PAR1$^{-/-}$ mice: A demyelinating agent (Lysolecithin, 2 μl of a 1% solution) was microinjected into the dorsal column white matter of adult male PAR1$^{+/+}$ or PAR1$^{-/-}$ mice. Mice were perfused with 4% paraformaldehyde 14 days later to examine the extent of axon remyelination in semithin 1 μm paraphenylenediamine stained plastic sections. Remyelinated axons (arrows in FIGS. 18A and 18B) were evident by their thin appearance relative to axon diameter, as compared to intact myelin sheaths. Counts of remyelinated axons demonstrated significantly higher numbers in PAR1 gene deficient (PAR1$^{-/-}$) mice relative to their PAR1$^{+/+}$ wild type counterparts (FIG. 18C). Thus, remyelination was enhanced in the PAR1$^{-/-}$ mice.

Figure 19A:
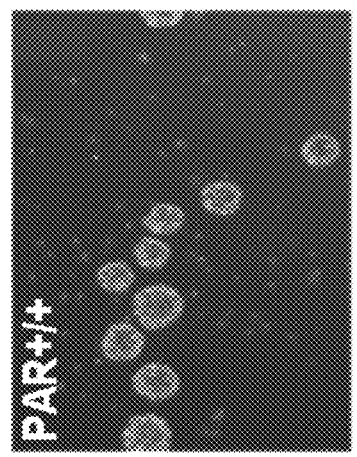
FIG. 19A is a graph plotting proliferation of neural precursor cells (NPCs) isolated from the subventricular zone (SVZ) of 8 week-old adult C57BL6/J mice and cultured in suspension. NPCs from PAR1$^{-/-}$ and PAR1$^{+/+}$ mice, determined based on incorporation of bromodeoxyuridine (BrdU; *P=0.009).
Figure 19B:
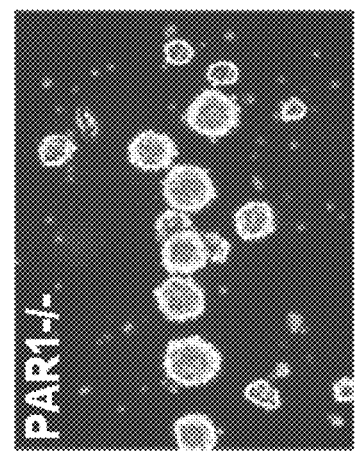
Figure 19C:
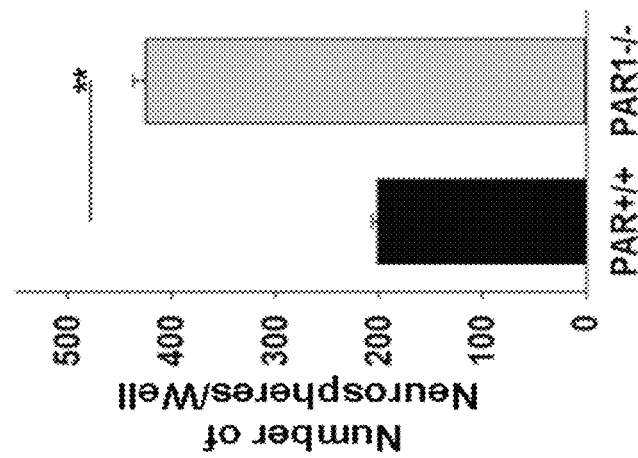
FIGS. 19C and 19D are photomicrographs showing representative images of cultures of neurospheres derived from PAR1$^{+/+}$ (FIG. 19C) and PAR1$^{-/-}$ (FIG. 19D) mice.
Figure 19D:
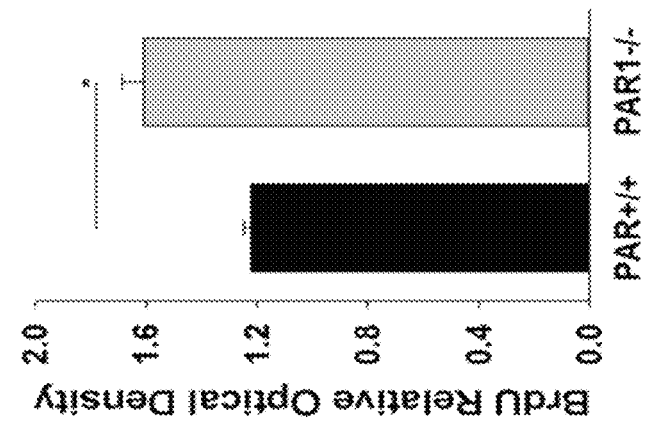

Effects of PAR1 gene deletion on neural precursor cell proliferation in vitro: Neural precursor cells (NPCs) were isolated from the subventricular zone (SVZ) of 8 week-old adult C57BL6/J mice and cultured in suspension. NPCs from PAR1$^{-/-}$ mice incorporated greater levels of bromodeoxyuridine (BrdU, an indicator of proliferation) (FIG. 19A, *P=0.009) and formed more neurospheres in vitro (FIGS. 19B-19D, **P=0.0007). The photomicrographs in FIGS. 19C and 19D are representative images of cultures of neurospheres derived from PAR1$^{+/+}$ or PAR1$^{-/-}$ mice, with those lacking the PAR1 gene demonstrating a significant increase in the number of neurospheres. These results suggested that deletion of the PAR1 receptor results in improved proliferation and expansion of NPCs derived from the adult forebrain.

Figure 20:
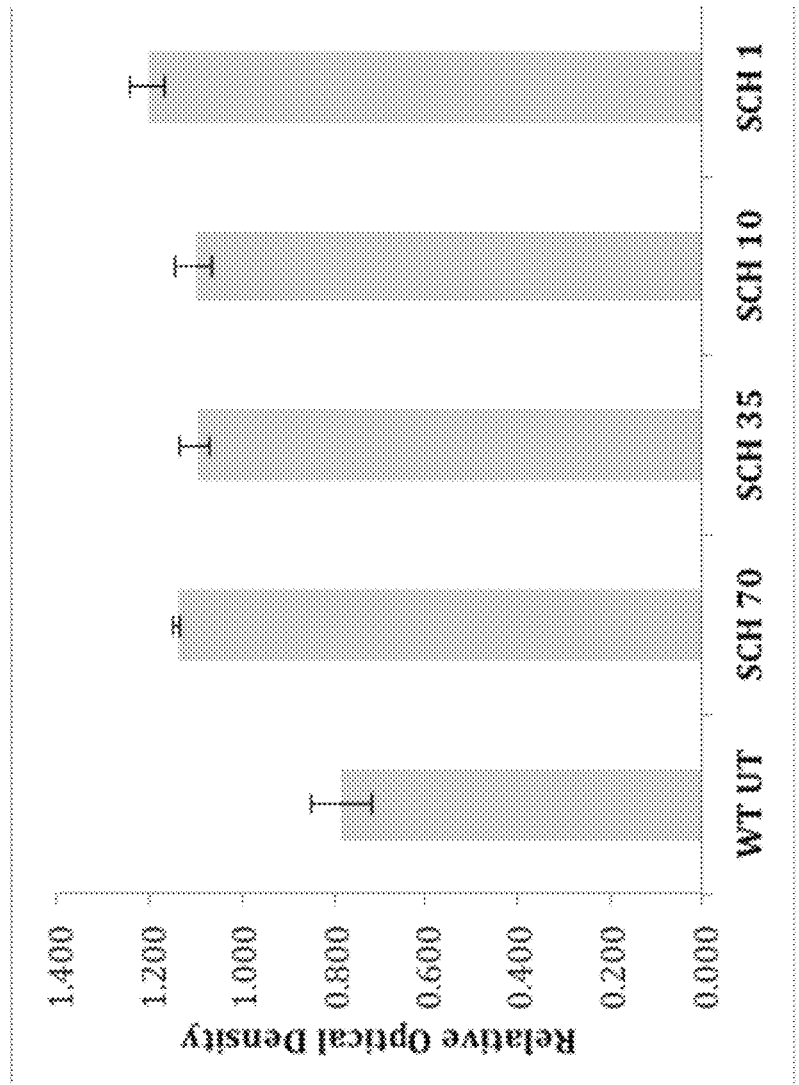
FIG. 20 is a graph plotting relative optical density of NPCs that were isolated from the SVZ of 8 week-old adult C57BL6/J mice, cultured in suspension, and treated with 70, 35, 10 or 1 nM SCH79797 (SCH). Proliferation is indicated by the levels of BrdU incorporation, measured as relative optical density.

Effects of pharmacologic inhibition of PAR1 on NPC proliferation in vitro: NPCs were isolated from the SVZ of 8 week-old adult C57BL6/J mice, cultured in suspension, and treated with 70, 35, 10, or 1 nM of SCH79797, a small molecule inhibitor of PAR1. Cells treated with SCH79797 incorporated greater levels of BrdU (FIG. 20), indicating that PAR1 can be targeted pharmacologically to promote expansion of NPCs.

Figure 21A:
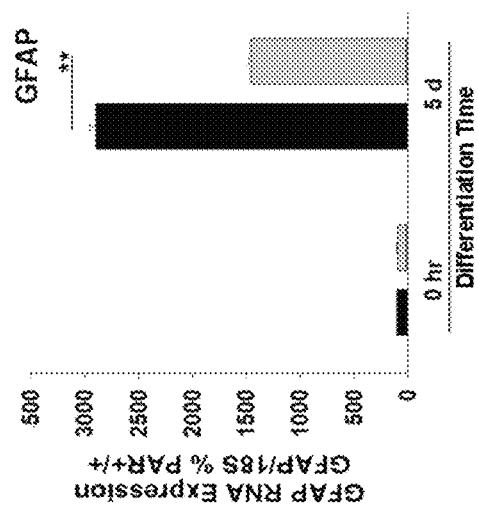
FIGS. 21A-21C are a series of graphs plotting expression of nestin (FIG. 21A; P=0.0002), Olig2 (FIG. 21B; P=0.0001), and glial fibrillary acidic protein (GFAP.
Figure 21B:
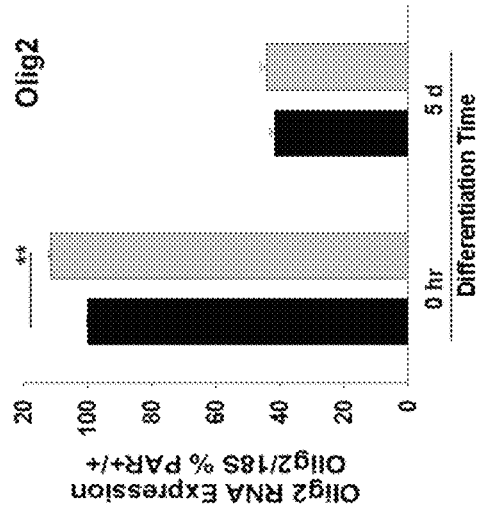
Figure 21C:
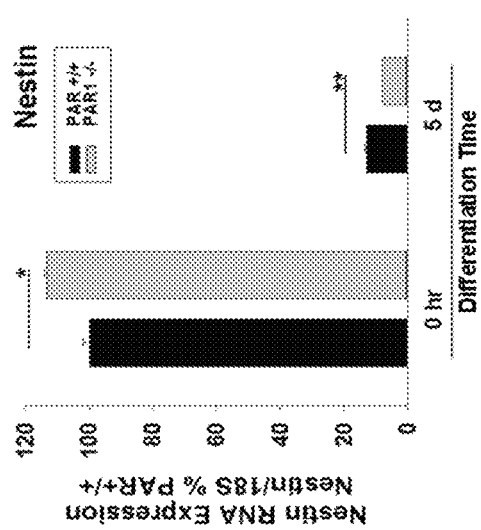

Effects of PAR1 gene deletion on differentiation of NPCs: NPCs were isolated from the SVZ of 8 week-old adult C57BL6/J PAR1$^{-/-}$ and PAR1$^{+/+}$ mice and cultured in suspension, and levels of differentiation markers were measured. PAR1 gene deletion enhanced NPC differentiation, as suggested by reduced levels of Nestin RNA in PAR1$^{-/-}$ NPCs after 5 days of cell culture in differentiation media (FIG. 21A; P=0.0002). The PAR1$^{-/-}$ NPCs also showed increased RNA levels for the oligodendrocyte marker Olig2 (FIG. 21B; P=0.0001) and reduced levels of RNA for a marker of astrocyte differentiation (glial fibrillary acidic protein (GFAP); FIG. 21C; **P=0.009, t-test).

Figure 22B:
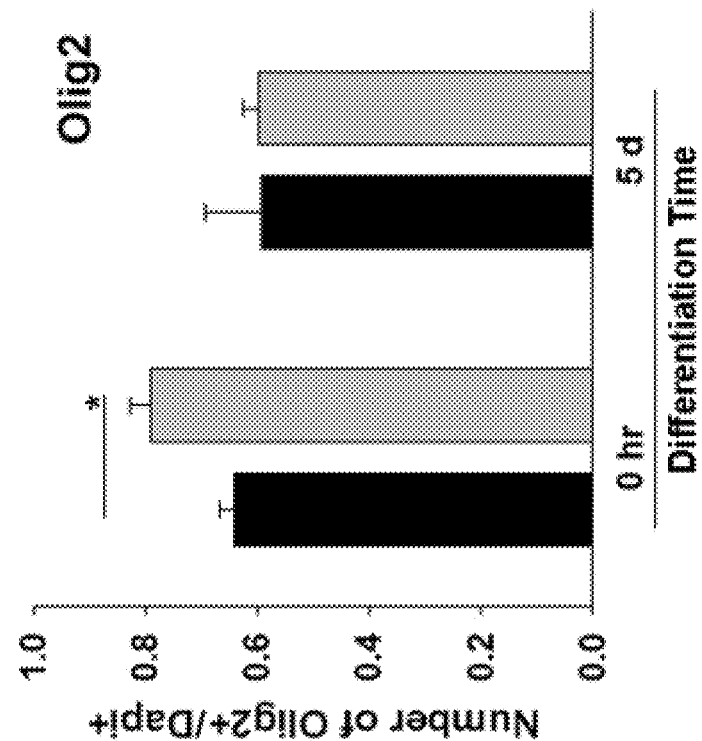
FIGS. 22A and 22B are a pair of graphs plotting the number of NPCs (isolated from the SVZ of 8 week-old adult C57BL6/J PAR1$^{-/-}$ and PAR1$^{+/+}$ mice) that were immunopositive for NG2 (a marker for oligodendrocyte progenitor cells.
Figure 22A:
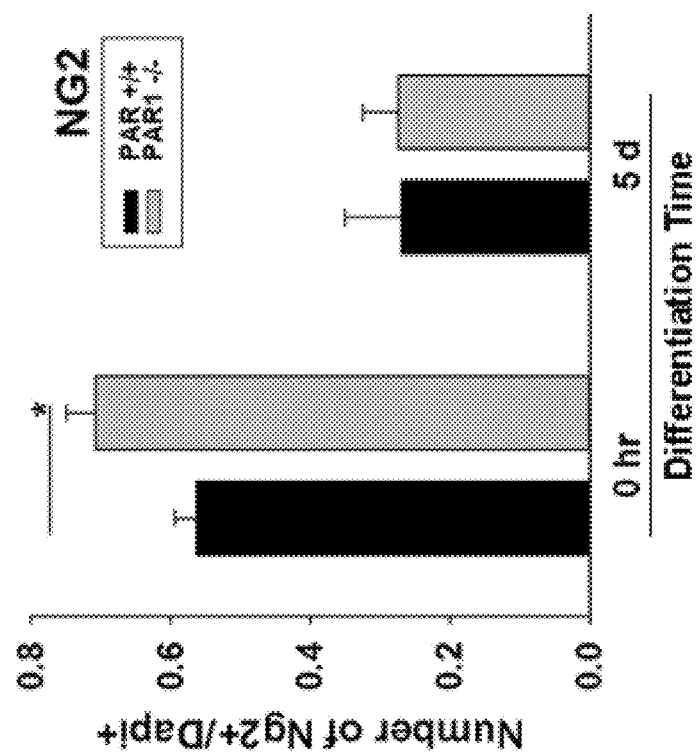

In further experiments, NPCs isolated from the SVZ of 8 week-old adult C57BL6/J PAR1$^{-/-}$ and PAR1$^{+/+}$ mice and cultured in suspension, and immunostained for NG2, a marker for oligodendrocyte progenitor cells, and Olig2, a marker for OPCs and mature oligodendrocytes at early stages of differentiation. These studies showed that the PAR1$^{-/-}$ cells exhibited an increase in the number of NPCs immunopositive for both NG2 (FIG. 22A) and Olig2 (FIG. 22B), suggesting that loss of PAR1 enhances early differentiation of NPCs toward an oligodendrocyte lineage.

Figure 23A:
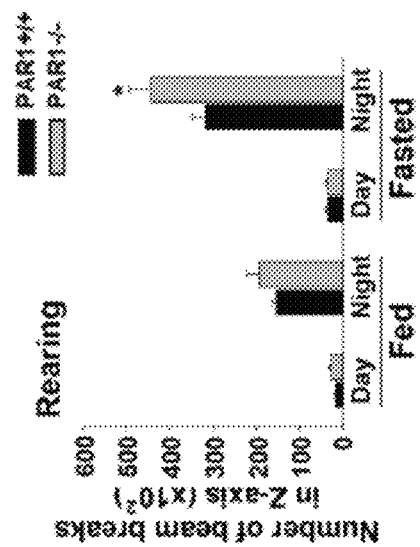
FIGS. 23A-23C are a series of graphs plotting the effects of PAR1 gene deletion on locomotor activity in adult mice. A comprehensive laboratory animal monitoring system was used to demonstrate that PAR1$^{-/-}$ mice had higher total activity under fed day (*P=0.04) or fasted night conditions (*P=0.02.
Figure 23B:
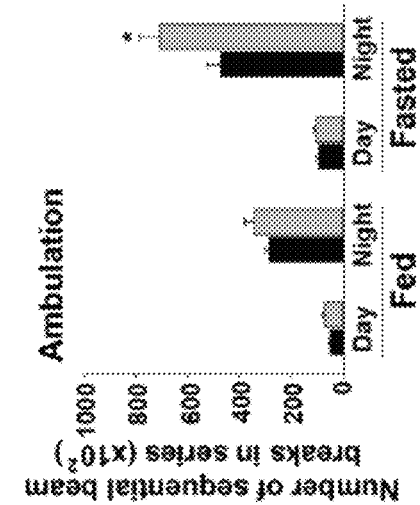
Figure 23C:
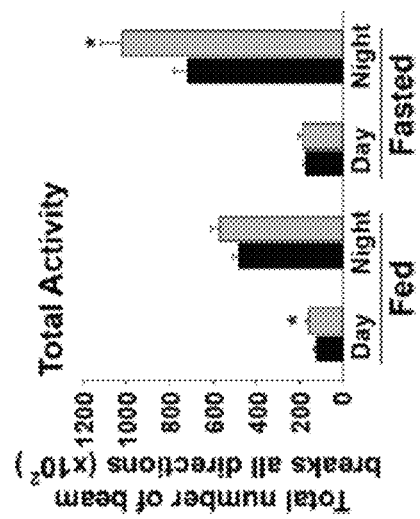

Motor activity in PAR1$^{-/-}$ mice: To link changes in spinal cord myelination observed in PAR1$^{-/-}$ mice to functional outcomes, overall motor activity, ambulation, and rearing during diurnal and nocturnal cycles under both fed and fasted conditions were evaluated. The overall activity of mice lacking the thrombin receptor was increased during the day under fed conditions (P=0.04), and also at night when fasted (P=0.02) (Student's unpaired t-test, FIG. 23A). In addition, both ambulation (P=0.02) and rearing responses (P=0.04) were increased in the PAR1-deficient mice under fasting conditions at night (Student's unpaired t-test, FIGS. 23B and 23C).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for modulating myelination in a subject, comprising delivering to the subject a plurality of PAR1$^{-/-}$ neural stem cells.

2. The method of claim 1, wherein the subject is a human.

3. The method of claim 2, wherein the human is an adult with a demyelinating disorder.

4. The method of claim 2, wherein the human is a preterm infant.

5. The method of claim 2, wherein the human is a juvenile with a demyelinating disorder.

6. The method of claim 2, wherein the human is a perinatal infant.

7. A method for providing a subject having a demyelinating disorder with modified stem cells, said method comprising delivering to the subject a plurality of PAR1$^{-/-}$ stem cells.

8. The method of claim 7, wherein the subject is a human.

9. The method of claim 8, wherein the human is an adult having said demyelinating disorder.

10. The method of claim 8, wherein the human is a preterm infant having said demyelinating disorder.

11. The method of claim 8, wherein the human is a juvenile having said demyelinating disorder.

12. The method of claim 8, wherein the human is a perinatal infant having said demyelinating disorder.

13. The method of claim 7, wherein the stem cells are neural stem cells.

* * * * *